United States Patent
Reynolds et al.

(10) Patent No.: US 11,180,774 B2
(45) Date of Patent: Nov. 23, 2021

(54) INSECTICIDAL PROTEINS

(71) Applicant: Syngenta Participations AG, Basel (CH)

(72) Inventors: Clarence Michael Reynolds, Research Triangle Park, NC (US); Christopher Fleming, Research Triangle Park, NC (US); Mark Greer Montgomery, Bracknell (GB)

(73) Assignee: Syngenta Participations AG, Basel (CH)

( * ) Notice: Subject to any disclaimer, the term of this patent is extended or adjusted under 35 U.S.C. 154(b) by 181 days.

(21) Appl. No.: 16/474,127

(22) PCT Filed: Jan. 8, 2018

(86) PCT No.: PCT/US2018/012730
§ 371 (c)(1),
(2) Date: Jun. 27, 2019

(87) PCT Pub. No.: WO2018/132325
PCT Pub. Date: Jul. 19, 2018

(65) Prior Publication Data
US 2019/0316148 A1    Oct. 17, 2019

Related U.S. Application Data

(60) Provisional application No. 62/445,429, filed on Jan. 12, 2017.

(51) Int. Cl.
*C12N 15/82* (2006.01)
*C07K 14/195* (2006.01)
*A01H 6/46* (2018.01)

(52) U.S. Cl.
CPC ........ *C12N 15/8286* (2013.01); *C07K 14/195* (2013.01); *A01H 6/4684* (2018.05); *Y02A 40/146* (2018.01)

(58) Field of Classification Search
None
See application file for complete search history.

(56) References Cited

U.S. PATENT DOCUMENTS

2011/0023184 A1   1/2011   Desai et al.

FOREIGN PATENT DOCUMENTS

WO   WO 2017/192560       * 11/2017
WO   WO 2017/192560 A1  * 11/2017

OTHER PUBLICATIONS

Rosado et al., A common fold mediates vertebrate defense and bacterial attack. Science 2007, 317 (5844): 1548-51; Abstract: Supplementary materials, p. 2.
GenBank CP009678.1. Pectobacterium cartovorum subsp. odoriferum strain BC S7, complete genome. Oct. 28, 2014 [Retrieved from the Internet Apr. 4, 2018: <https://www.ncbi.nim.nih.gov/nuccore/CP009678>]; in entirety, nucleotides: 1936981-1934569, 16. 1% identity to SEQ ID No. 2.
GenBank AM711867.1. Clavibacter michiganensis subsp. michiganensis NCPPB 382 complete genome. Feb. 27, 2015 [Retrieved from the Internet Apr. 4, 2018: <https://www.ncbi.nim.nih.gov/nuccore/AM711867>]; p. 897, gene 2685035. 2686447, 18.3% identify to SEQ ID No. 99.
UniProtKB/TrEMBL A0A0F4QUD9_9GAMM. Dec. 9, 2015. [Retreived from the Internet: Mar. 27, 2018. <http://www.uniprot.org/uniprot/AoA0F-4QUD9.txt?version=4]; in entirety.
GenBank NP_928713.1. hypothetical protein plu 1415 [*Photorhabdus luminescens* subsp. laumondi TT01] (2014) [Retrieved from the Internet Apr. 11, 2018: <https://www.ncbi.nim.nih.gov/protein/NP_928713.1?report=genpept>]; in entirety.
Reboul et al.. Giant MACPF/CDC pore forming toxins: A class of their own. Biochim Biophys Acta 2016, 1858(3) 475-86; AbstractL p. 477, Fig. 2 and its legend.
UniProtKB/TrEMBL A8GEE9_SERP5. Membrane attack complex component/perforin/complement C9 (Nov. 2, 2016) [Retreived from the Internet: Apr. 4, 2018. <http://www.uniprot.org/uniprot/A8GEE9.text?version=38>]; amino acids 312-486, 42.4% identity to SEQ ID No. 71.
International Search Report dated Apr. 25, 2018 for International Application No. PCT/US2018/012730.

* cited by examiner

*Primary Examiner* — Russell T Boggs
(74) *Attorney, Agent, or Firm* — Amy Krom

(57) ABSTRACT

Compositions and methods for controlling plant pests are disclosed. In particular, novel insecticidal proteins having toxicity against Coleopteran and/or Lepidopteran insect pests are provided. Nucleic acid molecules encoding the novel insecticidal proteins are also provided. Methods of making the insecticidal proteins and methods of using the insecticidal proteins and nucleic acids encoding the insecticidal proteins of the invention, for example in transgenic plants to confer protection from insect damage, are also disclosed.

10 Claims, No Drawings

Specification includes a Sequence Listing.

SEQUENCE LISTING

```
<160> NUMBER OF SEQ ID NOS: 100

<210> SEQ ID NO 1
<211> LENGTH: 490
<212> TYPE: PRT
<213> ORGANISM: Woodsholea maritima

<400> SEQUENCE: 1

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255
```

Gln Asn Ser Asp Ile His Lys Ile Val Val Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 2
<211> LENGTH: 1473
<212> TYPE: DNA
<213> ORGANISM: artificial sequence
<220> FEATURE:
<223> OTHER INFORMATION: Woodsholea maritima

<400> SEQUENCE: 2
atgaaaagct tggatcacgt tgctcatcag aacttactga atgaaccgac tcaccataaa      60
agcaatacca aggcggcgct gatgcgtcat caggaaaaacc tggttgaacg ctatctgccg    120
ggtgtggagg tgattggggc aggttacaac cctttcggcg tatacgcgtc cactgactca    180
gttactgtgc aacttttttga ttggcaaagc gcgccatcag aaccggtcat ttttaacccc    240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg cgtcttcgaa ccaataaagt acaggtggac    660
cacacatacg agaatgaaac cattgccaag gccagctacg aagccttaac tgggcagatc    720

```
tctgctgaga ctgcggctaa atatcgccaa agcatgtcgt cgttctccca gaactccgat      780
attcacaaaa ttgtggtcgg cggagacgga gtcgcgggcg cgaaagtgta tagcggtgac      840
aaggcggatt tcgatgcttg ggctgacacc gtggggacgt ctccagattt tgtggacttt      900
gttagcagcg ttcctatgtt gggaatttgg gaactgtgca agatgacgc gcaggcgaaa       960 aagatggaag attactataa taatacgtgg gccccgcgga aaagcaaaga ggctcaaatt      1020
tatgctgatt atatcgacgc agtcgaagtg atccagagta attcttcggg ggttcgccct      1080
cccagtggat atacgaaaat tgattacgac ctcaataaag gcgccggtgg ggattatatc      1140
tacctgtgtt atcataaagc ccgttatagc gcttactcag aaaacaaaga ttgcgtttct      1200
gatttaatta ttattaaggg aaacggagca cgcgccccga gcggttatac gaaaattgat      1260
gtggatttga atgaggatgc agtggaaaa tacctgtatt tatgctacaa gaagcaaagt       1320
tacgacaatg tggaagcaat caaggggctg gcggtagttg gtggtgacaa ttcgcatacc      1380
cctgctccgt acggttaccg tcggattgac accgatgtta acgagggggc cggaggtgag      1440
tacatttata tctgttactc caaaggggct taa                                    1473

<210> SEQ ID NO 3
<211> LENGTH: 1473
<212> TYPE: DNA
<213> ORGANISM: Woodsholea maritima

<400> SEQUENCE: 3
atgaaaagct tagatcacgt agctcatcaa aacctttaa atgagcccac ccaccataaa         60
tccaatacca aagccgcttt gatgcgccac caagagaatt tggtggagcg ctatttgcca      120
ggtgttgaag ttatcggtgc gggctataat ccttttggcg tttatgcctc aaccgatagt      180
gtaacggttc aattgtttga ctggcagtca gcaccgagtg aacctgtcat ctttaaccct      240
gattatattg cgccaaaagc tgttagcgtt cagcagaatg acgaagcgcg ctataccaat      300
gtttctggga aaacaatcaa caccttttcaa aagaatttca gcctaaaggt cacccgttgcg    360 ggctcgtaca atttatttttc gggctctgta tcaaatgaat tttcatcttc tgaaacgcgc      420
aatgcggaaa acgagttttc tcgtattcag caatctcattc gcgtatggtc tttgcgcttg     480
gcctatacgg actcgttgcg ggagtatttg aaggcagatg tgcgtgacta tattgattcc      540
attcaatcgg acgcgcagat tgaaattctg ttcgaccgtt atggtagtca cttcttaacc      600
ggtgttgtca tgggtggggc cgcgatcatg gcctcatcga ccaacaaggt ccaagtcgac      660
catacctatg agaatgagac gattgccaag gccagttatg aagccttaac cgggcagatc      720
agcgcggaaa ccgccgcgaa atatcgccaa tccatgtcca gcttctcaca aaactctgac      780
attcataaga tcgtcgtggg cggcgatggt gtcgctgggg ccaaggtcta tagcggtgac      840
aaggctgatt ttgacgcctg gctgatacc gtgggcacat caccggattt tgtagacttc       900
gtttcttctg ttccgatgtt gggcatttgg gaattgtgca agacgatgc ccaagccaaa       960 aaaatggagg attactataa taacacttgg gcgccgcgta agtcaaaaga agctcaaata     1020
tatgctgatt atattgacgc ggttgaggtt attcaaagta acagctctgg tgtccgtcca     1080
ccgtcagggt ataccaaaat tgattatgat ctcaacaaag gcgccggcgg ggattatatc     1140
tatctatgct atcataaagc ccgctatagc gcctatagtg aaaacaaaga ctgcgtatct     1200
gacttgatca taatcaaggg caatggtgca cgcgcgcctt caggctatac caaaatcgat     1260
gttgatttaa atgaagatgc gggtgggaaa tatctctatc tttgttataa aaaacaaagc     1320
tatgataatg ttgaagcaat caaggcttg gcggttgtcg gtggcgataa ttcacataca       1380
```

```
ccggcaccat acggttatag gcgtattgat acagacgtca atgaaggtgc tggtggtgaa    1440
tatatctata tttgctactc aaaaggcgct tga                                 1473

<210> SEQ ID NO 4
<211> LENGTH: 1473
<212> TYPE: DNA
<213> ORGANISM: artificial sequence
<220> FEATURE:
<223> OTHER INFORMATION: Woodsholea maritima

<400> SEQUENCE: 4
atgaaaagct tggatcacgt tgctcatcag aacttactga atgaaccgac tcaccataaa      60
agcaatacca aggcggcgct gatgcgtcat caggaaaacc tggttgaacg ctatctgccg     120
ggtgtggagg tgattggggc aggttacaac cctttcggcg tatacgcgtc cactgactca     180
gttactgtgc aacttttga ttggcaaagc gcgccatcag aaccggtcat ttttaacccc     240
gattacattg ctccgaaagc tgtgtcagta caacaaaatg atgaagcccg gtatacgaac     300
gttagcggca aaacaatcaa cacgtttcaa aaaaacttct ccctgaaagt tactgtcgcg     360
ggatcctata acttatttag cggtagcgtc agcaatgaat tcagcagcag cgaaactcgc     420
aatgcagaaa acgaatttag ccgcatccaa cagagcatcc gcgtctggtc tctgcgcctc     480
gcgtacacgg attccctgcg tgaatattta aagcggacg ttcgcgatta tatcgatagc     540
attcaatcag atgcgcagat tgaaattctg tttgatcgtt acgggtcaca tttccttacc     600
ggcgtggtga tgggtggcgc agcaatcatg gcgtcttcga ccaataaagt acaggtggac     660
cacacatacg agaatgaaac cattgccaag gccagctacg aagccttaac tgggcagatc     720
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt tcgatgcttg gctgacaccg tggggacgt ctccagattt tgtggacttt     900
gttagcagcg ttcctatgtt gggaatttgg gaactgtgca agatgacgc gcaggcgaaa     960 aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga ttgcgttttct   1200 gatttaatta ttattaaggg aaacggagca cgcgccccga gcggttatac gaaaattgat    1260 gtggattttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgaggggc cggaggtgag    1440 tacatttata tctcttactc aaaggggct taa                                  1473

<210> SEQ ID NO 5
<211> LENGTH: 1472
<212> TYPE: DNA
<213> ORGANISM: artificial sequence
<220> FEATURE:
<223> OTHER INFORMATION: Woodsholea maritima

<400> SEQUENCE: 5
atgaaaagct tggatcacgt tgctcatcag aacttactga atgaaccgac tcaccataaa      60
agcaatacca aggcggcgct gatgcgtcat caggaaaacc tggttgaacg ctatctgccg     120
```

```
ggtgtggagg tgattggggc aggttacaac cctttcggcg tatacgcgtc cactgactca    180
gttactgtgc aacttttga ttggcaaagc gcgccatcag aaccggtcat ttttaacccc    240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa    960
aagatggaag attactataa taatacgtgg gccccgcgca aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaaacaaaga ttgcgtttct   1200
gatttaatta ttattaaggg aaacggagca cgcgccccga gcggttatac gaaaattgat   1260
gtggatttga atgaggatgc aggtggaaaa tacctgtatt tatcttacaa gaagcaaagt   1320
tacgacaatg tggaagcaat caaggggctg gcggtagttg gtggtgacaa ttcgcatacc   1380
cctgctccgt acggttaccg tcggattgac accgatgtta acgagggggc cggaggtgag   1440
tacatttata tctgttactc caaaggggct ta                                 1472
```

<210> SEQ ID NO 6
<211> LENGTH: 1473
<212> TYPE: DNA
<213> ORGANISM: artificial sequence
<220> FEATURE:
<223> OTHER INFORMATION: Woodsholea maritima

<400> SEQUENCE: 6

```
atgaaaagct tggatcacgt tgctcatcag aacttactga tgaaccgac tcaccataaa     60
agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aacttttga ttggcaaagc gcgccatcag aaccggtcat ttttaacccc    240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
```

```
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt tcgatgcttg ggctgacacc gtggggacgt ctccagattt tgtggacttt     900
gttagcagcg ttcctatgtt gggaatttgg gaactgtgca agatgacgc gcaggcgaaa     960 aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga ttctgtttct    1200
gatttaatta ttattaaggg aaacggagca cgcgccccga gcggttatac gaaaattgat    1260
gtggatttga atgaggatgc agttggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgaggggc cggaggtgag    1440 tacattata tctgttactc caaaggggct taa                                 1473

<210> SEQ ID NO 7
<211> LENGTH: 1473
<212> TYPE: DNA
<213> ORGANISM: artificial sequence
<220> FEATURE:
<223> OTHER INFORMATION: Woodsholea maritima

<400> SEQUENCE: 7
atgaaaagct tggatcacgt tgctcatcag aacttactga atgaaccgac tcaccataaa      60
agcaatacca aggcggcgct gatgcgtcat caggaaaaacc tggttgaacg ctatctgccg    120
ggtgtggagg tgattggggc aggttacaac cctttcggcg tatacgcgtc cactgactca    180
gttactgtgc aactttttga ttggcaaagc gcgccatcag aaccggtcat ttttaacccc    240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attcctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa    960 aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtctt atcataaagc ccgttatagc gcttactcag aaaacaaaga ttgcgtttct   1200
gatttaatta ttattaaggg aaacggagca cgcgccccga gcggttatac gaaaattgat   1260
```

| | |
|---|---|
| gtggatttga atgaggatgc aggtggaaaa tacctgtatt tatgctacaa gaagcaaagt | 1320 |
| tacgacaatg tggaagcaat caaggggctg gcggtagttg gtggtgacaa ttcgcatacc | 1380 |
| cctgctccgt acggttaccg tcggattgac accgatgtta acgaggggc cggaggtgag | 1440 |
| tacatttata tctgttactc caaagggct taa | 1473 |

<210> SEQ ID NO 8
<211> LENGTH: 1473
<212> TYPE: DNA
<213> ORGANISM: artificial sequence
<220> FEATURE:
<223> OTHER INFORMATION: Woodsholea maritima

<400> SEQUENCE: 8

| | |
|---|---|
| atgaaaagct tggatcacgt tgctcatcag aacttactga atgaaccgac tcaccataaa | 60 |
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aactttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |
| ggatcctata acttatttag cggtagcgtc agcaatgaat tcagcagcag cgaaactcgc | 420 |
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |
| cacacatacg agaatgaaac cattgccaag gccagctacg aagccttaac tgggcagatc | 720 |
| tctgctgaga ctgcggctaa atatcgccaa agcatgtcgt cgttctccca gaactccgat | 780 |
| attcacaaaa ttgtggtcgg cggagacgga gtcgcgggcg cgaaagtgta tagcggtgac | 840 |
| aaggcggatt cgatgcttg ggctgacacc gtggggacgt ctccagattt tgtggacttt | 900 |
| gttagcagcg ttcctatgtt gggaatttgg gaactgtcta agatgacgc gcaggcgaaa | 960 |
| aagatggaag attactataa taatacgtgg gccccgcgga aaagcaaaga ggctcaaatt | 1020 |
| tatgctgatt atatcgacgc agtcgaagtg atccagagta attcttcggg ggttcgccct | 1080 |
| cccagtggat atacgaaaat tgattacgac ctcaataaag gcgccggtgg ggattatatc | 1140 |
| tacctgtgtt atcataaagc ccgttatagc gcttactcag aaaacaaaga ttgcgtttct | 1200 |
| gatttaatta ttattaaggg aaacggagca cgcgccccga gcggttatac gaaaattgat | 1260 |
| gtggatttga atgaggatgc aggtggaaaa tacctgtatt tatgctacaa gaagcaaagt | 1320 |
| tacgacaatg tggaagcaat caaggggctg gcggtagttg gtggtgacaa ttcgcatacc | 1380 |
| cctgctccgt acggttaccg tcggattgac accgatgtta acgaggggc cggaggtgag | 1440 |
| tacatttata tctgttactc caaagggct taa | 1473 |

<210> SEQ ID NO 9
<211> LENGTH: 1473
<212> TYPE: DNA
<213> ORGANISM: artificial sequence
<220> FEATURE:
<223> OTHER INFORMATION: Woodsholea maritima

<400> SEQUENCE: 9

| | |
|---|---|
| atgaaaagct tggatcacgt tgctcatcag aacttactga atgaaccgac tcaccataaa | 60 |

```
agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aacttttttga ttggcaaagc gcgccatcag aaccggtcat ttttaacccc   240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacga attccctgcg tgaatattta aaagcggacg ttcgcgatta tatcgatagc    540
attcaatcag atgcgcagat tgaaattctg tttgatcgtt gggggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgc tcccagattt tgtggacttt    900
gttagcagcg ttcctatgtt gggaatttgg gaactgtgca agatgacgc gcaggcgaaa     960 aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag cgccggtgg ggattatatc    1140 tacctgtgtt atcataaagc ccgttatagc gcttactcag aaaacaaaga ttgcgtttct   1200
gatttaatta ttattaaggg aaacggagca cgcgccccga gcggttatac gaaaattgat   1260
gtggatttga atgaggatgc aggtggaaaa tacctgtatt tatgctacaa gaagcaaagt   1320
tacgacaatg tggaagcaat caaggggctg gcggtagttg gtggtgacaa ttcgcatacc   1380
cctgctccgt acggttaccg tcggattgac accgatgtta acgaggggc cggaggtgag    1440 tacatttata tctgttactc caaaggggct taa                                1473
```

<210> SEQ ID NO 10
<211> LENGTH: 1473
<212> TYPE: DNA
<213> ORGANISM: artificial sequence
<220> FEATURE:
<223> OTHER INFORMATION: Woodsholea maritima

<400> SEQUENCE: 10

```
atgaaaagct tggatcacgt tgctcatcag aacttactga atgaaccgac tcaccataaa     60
agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aacttttttga ttggcaaagc gcgccatcag aaccggtcat ttttaacccc   240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt tgggtcaca tttccttacc     600
```

```
ggcgtggtga tgggtggcgc agcaatcatg gcgtcttcga ccaataaagt acaggtggac      660
cacacatacg agaatgaaac cattgccaag gccagctacg aagccttaac tgggcagatc      720
tctgctgaga ctgcggctaa atatcgccaa agcatgtcgt cgttctccca gaactccgat      780
attcacaaaa ttgtggtcgg cggagacgga gtcgcgggcg cgaaagtgta tagcggtgac      840
aaggcggatt cgatgcttg ggctgacacc gtggggacgt ctccagattt tgtggacttt       900
gttagcagcg ttcctatgtt gggaatttgg gaactgtgca agatgacgc gcaggcgaaa       960 aagatggaag attactataa taatacgtgg gccccgcgga aaagcaaaga ggctcaaatt      1020
tatgctgatt atatcgacgc agtcgaagtg atccagagta attcttcggg ggttcgccct      1080
cccagtggat atacgaaaat tgattacgac ctcaataaag gcgccggtgg ggattatatc      1140
tacctgtgtt atcataaagc ccgttatagc gcttactcag aaaacaaaga ttgcgtttct      1200
gatttaatta ttattaaggg aaacggagca cgcgccccga gcggttatac gaaaattgat      1260
gtggatttga atgaggatgc agtggaaaa tacctgtatt tatgctacaa gaagcaaagt       1320
tacgacaatg tggaagcaat caaggggctg gcggtagttg gtggtgacaa ttcgcatacc      1380
cctgctccgt acggttaccg tcggattgac accgatgtta acgaggggc cggaggtgag       1440 tacatttata tctgttactc caagggggct taa                                   1473

<210> SEQ ID NO 11
<211> LENGTH: 1473
<212> TYPE: DNA
<213> ORGANISM: artificial sequence
<220> FEATURE:
<223> OTHER INFORMATION: Woodsholea maritima

<400> SEQUENCE: 11
atgaaaagct tggatcacgt tgctcatcag aacttactga atgaaccgac tcaccataaa       60
agcaatacca aggcggcgct gatgcgtcat caggaaaacc tggttgaacg ctatctgccg      120
ggtgtggagg tgattgggc aggttacaac ccttcggcg tatacgcgtc cactgactca        180
gttactgtgc aacttttga ttggcaaagc gcgccatcag aaccggtcat ttttaacccc       240
gattacattg ctccgaaagc tgtgtcagta caacaaaatg atgaagcccg gtatacgaac      300
gttagcggca aacaatcaa cacgtttcaa aaaaacttct ccctgaaagt tactgtcgcg       360
ggatcctata acttatttag cggtagcgtc agcaatgaat tcagcagcag cgaaactcgc      420
aatgcagaaa acgaatttag ccgcatccaa cagagcatcc gcgtctggtc tctgcgcctc      480
gcgtacacgg attccctgcg tgaatattta aaagcggacg ttcgcgatta tatcgatagc      540
attcaatcag atgcgcagat tgaaattctg tttgatcgtt acgggtcaca tttccttacc      600
ggcgtggtga tgggtggcgc agcaatcatg gcgtcttcga ccaataaagt acaggtggac     660
cacacatacg agaatgaaac cattgccaag gccagctacg aagccttaac tgggcagatc     720
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt cgatgcttg ggctgacacc gtggggacgt ctccagattt tgtggacttt      900
gttagcagcg ttcctatgtt gggaatttgg gaactgtgca agatgacgc gcaggcgaaa      960 aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtctt atcataaagc ccgttatagc gcttactcag aaaacaaaga ttgcgtttct    1200
```

```
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgaggggc cggaggtgag    1440 tacatttata tctcttactc caaagggct taa                                 1473
```

<210> SEQ ID NO 12
<211> LENGTH: 1473
<212> TYPE: DNA
<213> ORGANISM: artificial sequence
<220> FEATURE:
<223> OTHER INFORMATION: Woodsholea maritima

<400> SEQUENCE: 12

```
atgaaaagct tggatcacgt tgctcatcag aacttactga atgaaccgac tcaccataaa     60
agcaatacca aggcggcgct gatgcgtcat caggaaaaacc tggttgaacg ctatctgccg    120
ggtgtggagg tgattggggc aggttacaac cctttcggcg tatacgcgtc cactgactca    180
gttactgtgc aacttttga ttggcaaagc gcgccatcag aaccggtcat tttttaacccc    240 gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacacacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtgggggacgt ctccagattt tgtggacttt    900
gttagcagcg ttcctatgtt gggaaatttgg gaactgtgca agatgacgc gcaggcgaaa    960 aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaaacaaaga ttgcgtttct   1200
gatttaatta ttattaaggg aaacggagca cgcgccccga gcggttatac gaaaattgat   1260
gtggatttga atgaggatgc aggtggaaaa tacctgtatt tatcttacaa gaagcaaagt   1320
tacgacaatg tggaagcaat caaggggctg gcggtagttg gtggtgacaa ttcgcatacc   1380
cctgctccgt acggttaccg tcggattgac accgatgtta acgaggggc cggaggtgag   1440 tacatttata tctcttactc caaagggct taa                                 1473
```

<210> SEQ ID NO 13
<211> LENGTH: 1473
<212> TYPE: DNA
<213> ORGANISM: artificial sequence
<220> FEATURE:
<223> OTHER INFORMATION: Woodsholea maritima

<400> SEQUENCE: 13

```
atgaaaagct tggatcacgt tgctcatcag aacttactga atgaaccgac tcaccataaa    60
agcaatacca aggcggcgct gatgcgtcat caggaaaacc tggttgaacg ctatctgccg   120
ggtgtggagg tgattggggc aggttacaac cctttcggcg tatacgcgtc cactgactca   180
gttactgtgc aacttttga ttggcaaagc gcgccatcag aaccggtcat ttttaacccc   240
gattacattg ctccgaaagc tgtgtcagta caacaaaatg atgaagcccg gtatacgaac   300
gttagcggca aacaatcaa cacgtttcaa aaaaacttct ccctgaaagt tactgtcgcg   360
ggatcctata acttatttag cggtagcgtc agcaatgaat tcagcagcag cgaaactcgc   420
aatgcagaaa acgaatttag ccgcatccaa cagagcatcc gcgtctggtc tctgcgcctc   480
gcgtacacgg attccctgcg tgaatattta aaagcggacg ttcgcgatta tatcgatagc   540
attcaatcag atgcgcagat tgaaattctg tttgatcgtt acgggtcaca tttccttacc   600
ggcgtggtga tgggtggcgc agcaatcatg gcgtcttcga ccaataaagt acaggtggac   660
cacacatacg agaatgaaac cattgccaag gccagctacg aagccttaac tgggcagatc   720
tctgctgaga ctgcggctaa atatcgccaa agcatgtcgt cgttctccca gaactccgat   780
attcacaaaa ttgtggtcgg cggagacgga gtcgcgggcg cgaaagtgta tagcggtgac   840
aaggcggatt tcgatgcttg ggctgacacc gtggggacgt ctccagattt tgtggacttt   900
gttagcagcg ttcctatgtt gggaatttgg gaactgtgca agatgacgc gcaggcgaaa   960
aagatggaag attactataa taatacgtgg gccccgcgga aaagcaaaga ggctcaaatt  1020
tatgctgatt atatcgacgc agtcgaagtg atccagagta attcttcggg ggttcgccct  1080
cccagtggat atacgaaaat tgattacgac ctcaataaag gcgccggtgg ggattatatc  1140
tacctgtgtt atcataaagc ccgttatagc gcttactcag aaaacaaaga ttctgtttct  1200
gatttaatta ttattaaggg aaacggagca cgcgccccga gcggttatac gaaaattgat  1260
gtggatttga atgaggatgc agtgaaaa tacctgtatt tatcttacaa gaagcaaagt  1320
tacgacaatg tggaagcaat caaggggctg gcggtagttg gtggtgacaa ttcgcatacc  1380
cctgctccgt acggttaccg tcggattgac accgatgtta acgagggggc cggaggtgag  1440
tacatttata tctgttactc caaagggggct taa                             1473
```

<210> SEQ ID NO 14
<211> LENGTH: 1473
<212> TYPE: DNA
<213> ORGANISM: artificial sequence
<220> FEATURE:
<223> OTHER INFORMATION: Woodsholea maritima

<400> SEQUENCE: 14

```
atgaaaagct tggatcacgt tgctcatcag aacttactga atgaaccgac tcaccataaa    60
agcaatacca aggcggcgct gatgcgtcat caggaaaacc tggttgaacg ctatctgccg   120
ggtgtggagg tgattggggc aggttacaac cctttcggcg tatacgcgtc cactgactca   180
gttactgtgc aacttttga ttggcaaagc gcgccatcag aaccggtcat ttttaacccc   240
gattacattg ctccgaaagc tgtgtcagta caacaaaatg atgaagcccg gtatacgaac   300
gttagcggca aacaatcaa cacgtttcaa aaaaacttct ccctgaaagt tactgtcgcg   360
ggatcctata acttatttag cggtagcgtc agcaatgaat tcagcagcag cgaaactcgc   420
aatgcagaaa acgaatttag ccgcatccaa cagagcatcc gcgtctggtc tctgcgcctc   480
gcgtacacgg attccctgcg tgaatattta aaagcggacg ttcgcgatta tatcgatagc   540
```

```
attcaatcag atgcgcagat tgaaattctg tttgatcgtt acgggtcaca tttccttacc      600
ggcgtggtga tgggtggcgc agcaatcatg gcgtcttcga ccaataaagt acaggtggac      660
cacacatacg agaatgaaac cattgccaag gccagctacg aagccttaac tgggcagatc      720
tctgctgaga ctgcggctaa atatcgccaa agcatgtcgt cgttctccca gaactccgat      780
attcacaaaa ttgtggtcgg cggagacgga gtcgcgggcg cgaaagtgta tagcggtgac      840
aaggcggatt tcgatgcttg ggctgacacc gtggggacgt ctccagattt tgtggacttt      900
gttagcagcg ttcctatgtt gggaatttgg gaactgtgca agatgacgc gcaggcgaaa      960 aagatggaag attactataa taatacgtgg gccccgcgga aaagcaaaga ggctcaaatt     1020
tatgctgatt atatcgacgc agtcgaagtg atccagagta attcttcggg ggttcgccct     1080
cccagtggat atacgaaaat tgattacgac ctcaataaag cgccggtgg ggattatatc     1140 tacctgtgtt atcataaagc ccgttatagc gcttactcag aaaacaaaga ttctgtttct     1200
gatttaatta ttattaaggg aaacggagca cgcgccccga gcggttatac gaaaattgat     1260
gtggatttga atgaggatgc aggtggaaaa tacctgtatt tatgctacaa gaagcaaagt     1320
tacgacaatg tggaagcaat caaggggctg gcggtagttg gtggtgacaa ttcgcatacc     1380
cctgctccgt acggttaccg tcggattgac accgatgtta acgaggggc cggaggtgag     1440 tacatttata tctcttactc caaaggggct taa                                  1473

<210> SEQ ID NO 15
<211> LENGTH: 1473
<212> TYPE: DNA
<213> ORGANISM: artificial sequence
<220> FEATURE:
<223> OTHER INFORMATION: Woodsholea maritima

<400> SEQUENCE: 15
atgaaaagct tggatcacgt tgctcatcag aacttactga atgaaccgac tcaccataaa       60
agcaatacca aggcggcgct gatgcgtcat caggaaaacc tggttgaacg ctatctgccg      120
ggtgtggagg tgattggggc aggttacaac cctttcggcg tatacgcgtc cactgactca      180
gttactgtgc aacttttga ttggcaaagc gcgccatcag aaccggtcat ttttaacccc      240
gattacattg ctccgaaagc tgtgtcagta caacaaaatg atgaagcccg gtatacgaac      300
gttagcggca aaacaatcaa cacgtttcaa aaaaacttct ccctgaaagt tactgtcgcg      360
ggatcctata acttatttag cggtagcgtc agcaatgaat tcagcagcag cgaaactcgc      420
aatgcagaaa acgaatttag ccgcatccaa cagagcatcc gcgtctggtc tctgcgcctc      480
gcgtacacgg attccctgcg tgaatattta aaagcggacg ttcgcgatta tatcgatagc      540
attcaatcag atgcgcagat tgaaattctg tttgatcgtt acgggtcaca tttccttacc      600
ggcgtggtga tgggtggcgc agcaatcatg gcgtcttcga ccaataaagt acaggtggac      660
cacacatacg agaatgaaac cattgccaag gccagctacg aagccttaac tgggcagatc      720
tctgctgaga ctgcggctaa atatcgccaa agcatgtcgt cgttctccca gaactccgat      780
attcacaaaa ttgtggtcgg cggagacgga gtcgcgggcg cgaaagtgta tagcggtgac      840
aaggcggatt tcgatgcttg ggctgacacc gtggggacgt ctccagattt tgtggacttt      900
gttagcagcg ttcctatgtt gggaatttgg gaactgtgca agatgacgc gcaggcgaaa      960 aagatggaag attactataa taatacgtgg gccccgcgga aaagcaaaga ggctcaaatt     1020
tatgctgatt atatcgacgc agtcgaagtg atccagagta attcttcggg ggttcgccct     1080
```

-continued

```
cccagtggat atacgaaaat tgattacgac ctcaataaag gcgccggtgg ggattatatc      1140
tacctgtctt atcataaagc ccgttatagc gcttactcag aaaacaaaga ttgcgtttct      1200
gatttaatta ttattaaggg aaacggagca cgcgccccga gcggttatac gaaaattgat      1260
gtggatttga atgaggatgc aggtggaaaa tacctgtatt tatcctacaa gaagcaaagt      1320
tacgacaatg tggaagcaat caaggggctg gcggtagttg gtggtgacaa ttcgcatacc      1380
cctgctccgt acggttaccg tcggattgac accgatgtta acgagggggc cggaggtgag      1440
tacatttata tctcttactc caaagggggct taa                                  1473
```

<210> SEQ ID NO 16
<211> LENGTH: 1473
<212> TYPE: DNA
<213> ORGANISM: artificial sequence
<220> FEATURE:
<223> OTHER INFORMATION: Woodsholea maritima

<400> SEQUENCE: 16

```
atgaaaagct tggatcacgt tgctcatcag aacttactga atgaaccgac tcaccataaa        60
agcaatacca aggcggcgct gatgcgtcat caggaaaaacc tggttgaacg ctatctgccg       120
ggtgtggagg tgattggggc aggttacaac cctttcggcg tatacgcgtc cactgactca       180
gttactgtgc aacttttttga ttggcaaagc gcgccatcag aaccggtcat ttttaacccc      240
gattacattg ctccgaaagc tgtgtcagta caacaaaatg atgaagcccg gtatacgaac       300
gttagcggca aaacaatcaa cacgtttcaa aaaaacttct ccctgaaagt tactgtcgcg       360
ggatcctata acttatttag cggtagcgtc agcaatgaat tcagcagcag cgaaactcgc       420
aatgcagaaa acgaatttag ccgcatccaa cagagcatcc gcgtctggtc tctgcgcctc       480
gcgtacacgg attccctgcg tgaatattta aaagcggacg ttcgcgatta tatcgatagc       540
attcaatcag atgcgcagat tgaaattctg tttgatcgtt acgggtcaca tttccttacc       600
ggcgtggtga tgggtggcgc agcaatcatg gcgtcttcga ccaataaagt acaggtggac       660
cacacatacg agaatgaaac cattgccaag gccagctacg aagccttaac tgggcagatc       720
tctgctgaga ctgcggctaa atatcgccaa agcatgtcgt cgttctccca gaactccgat       780
attcacaaaa ttgtggtcgg cggagacgga gtcgcgggcg cgaaagtgta tagcggtgac       840
aaggcggatt cgatgcttg ggctgacacc gtggggacgt ctccagattt tgtgactttt        900
gttagcagcg ttcctatgtt gggaatttgg gaactgtcta agatgacgc gcaggcgaaa        960 aagatggaag attactataa taatacgtgg gccccgcgga aaagcaaaga ggctcaaatt      1020
tatgctgatt atatcgacgc agtcgaagtg atccagagta attcttcggg ggttcgccct      1080
cccagtggat atacgaaaat tgattacgac ctcaataaag gcgccggtgg ggattatatc      1140
tacctgtctt atcataaagc ccgttatagc gcttactcag aaaacaaaga ttctgtttct      1200
gatttaatta ttattaaggg aaacggagca cgcgccccga gcggttatac gaaaattgat      1260
gtggatttga atgaggatgc aggtggaaaa tacctgtatt tatcttacaa gaagcaaagt      1320
tacgacaatg tggaagcaat caaggggctg gcggtagttg gtggtgacaa ttcgcatacc      1380
cctgctccgt acggttaccg tcggattgac accgatgtta acgagggggc cggaggtgag      1440
tacatttata tctcttactc caaagggggct taa                                  1473
```

<210> SEQ ID NO 17
<211> LENGTH: 1473
<212> TYPE: DNA
<213> ORGANISM: artificial sequence
<220> FEATURE:
<223> OTHER INFORMATION: Woodsholea maritima

<400> SEQUENCE: 17

```
atgaaaagct tggatcacgt tgctcatcag aacttactga atgaaccgac tcaccataaa    60
agcaatacca aggcggcgct gatgcgtcat caggaaaacc tggttgaacg ctatctgccg   120
ggtgtggagg tgattggggc aggttacaac cctttcggcg tatacgcgtc cactgactca   180
gttactgtgc aacttttttga ttggcaaagc gcgccatcag aaccggtcat ttttaacccc   240
gattacattg ctccgaaagc tgtgtcagta caacaaaatg atgaagcccg gtatacgaac   300
gttagcggca aaacaatcaa cacgtttcaa aaaaacttct ccctgaaagt tactgtcgcg   360
ggatcctata acttatttag cggtagcgtc agcaatgaat tcagcagcag cgaaactcgc   420
aatgcagaaa acgaatttag ccgcatccaa cagagcatcc gcgtctggtc tctgcgcctc   480
gcgtacacgg attccctgcg tgaatattta aaagcggacg ttcgcgatta tatcgatagc   540
attcaatcag atgcgcagat tgaaattctg tttgatcgtt acgggtcaca tttccttacc   600
ggcgtggtga tgggtggcgc agcaatcatg gcgtcttcga ccaataaagt acaggtggac   660
cacacatacg agaatgaaac cattgccaag gccagctacg aagccttaac tgggcagatc   720
tctgctgaga ctgcggctaa atatcgccaa agcatgtcgt cgttctccca gaactccgat   780
attcacaaaa ttgtggtcgg cggagacgga gtcgcgggcg cgaaagtgta tagcggtgac   840
aaggcggatt tcgatgcttg gcctgacacc gtggggacgt ctccagattt tgtggacttt   900
gttagcagcg ttcctatgtt gggaatttgg gaactgtgca agatgacgc gcaggcgaaa   960
aagatggaag attactataa taatacgtgg gccccgcgga aaagcaaaga ggctcaaatt  1020
tatgctgatt atatcgacgc agtcgaagtg atccagagta attcttcggg ggttcgccct  1080
cccagtggat atacgaaaat tgattacgac ctcaataaag gcgccggtgg ggattatatc  1140
tacctgtgtt atcataaagc ccgttatagc gcttactcag aaaacctcga ttgcgtttct  1200
gatttaatta ttattaaggg aaacggagca cgcgccccga gcggttatac gaaaattgat  1260
gtggatttga atgaggatgc agtggaaaa tacctgtatt tatgctacaa gaagcaaagt  1320
tacgacaatg tggaagcaat caaggggctg gcggtagttg gtggtgacaa ttcgcatacc  1380
cctgctccgt acggttaccg tcggattgac accgatgtta acgagggggc cggaggtgag  1440
tacatttata tctgttactc caaagggggct taa                               1473
```

<210> SEQ ID NO 18
<211> LENGTH: 1473
<212> TYPE: DNA
<213> ORGANISM: artificial sequence
<220> FEATURE:
<223> OTHER INFORMATION: Woodsholea maritima

<400> SEQUENCE: 18

```
atgaaaagct tggatcacgt tgctcatcag aacttactga atgaaccgac tcaccataaa    60
agcaatacca aggcggcgct gatgcgtcat caggaaaacc tggttgaacg ctatctgccg   120
ggtgtggagg tgattggggc aggttacaac cctttcggcg tatacgcgtc cactgactca   180
gttactgtgc aacttttttga ttggcaaagc gcgccatcag aaccggtcat ttttaacccc   240
gattacattg ctccgaaagc tgtgtcagta caacaaaatg atgaagcccg gtatacgaac   300
gttagcggca aaacaatcaa cacgtttcaa aaaaacttct ccctgaaagt tactgtcgcg   360
ggatcctata acttatttag cggtagcgtc agcaatgaat tcagcagcag cgaaactcgc   420
```

| | |
|---|---:|
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |
| cacacatacg agaatgaaac cattgccaag gccagctacg aagccttaac tgggcagatc | 720 |
| tctgctgaga ctgcggctaa atatcgccaa agcatgtcgt cgttctccca gaactccgat | 780 |
| attcacaaaa ttgtggtcgg cggagacgga gtcgcgggcg cgaaagtgta tagcggtgac | 840 |
| aaggcggatt tcgatgcttg ggctgacacc gtggggactc tccagatttt tgtggacttt | 900 |
| gttagcagcg ttcctatgtt gggaatttgg gaactgtgca agatgacgc gcaggcgaaa | 960 |
| aagatggaag attactataa taatacgtgg gccccgcgga aaagcaaaga ggctcaaatt | 1020 |
| tatgctgatt atatcgacgc agtcgaagtg atccagagta attcttcggg ggttcgccct | 1080 |
| cccagtggat atacgaaaat tgattacgac ctcaataaag gcgccggtgg ggattatatc | 1140 |
| tacctgtgtt atcataaagc ccgttatagc gcttactcag aaaacaaaga ttgcgtttct | 1200 |
| gatttaatta ttattctcgg aaacggagca cgcgccccga gcggttatac gaaaattgat | 1260 |
| gtggatttga atgaggatgc agtggaaaa tacctgtatt tatgctacaa gaagcaaagt | 1320 |
| tacgacaatg tggaagcaat caaggggctg gcggtagttg gtggtgacaa ttcgcatacc | 1380 |
| cctgctccgt acgttaccg tcggattgac accgatgtta acgaggggc cggaggtgag | 1440 |
| tacattata tctgttactc caaagggct taa | 1473 |

<210> SEQ ID NO 19
<211> LENGTH: 1473
<212> TYPE: DNA
<213> ORGANISM: artificial sequence
<220> FEATURE:
<223> OTHER INFORMATION: Woodsholea maritima

<400> SEQUENCE: 19

| | |
|---|---:|
| atgaaaagct tggatcacgt tgctcatcag aacttactga atgaaccgac tcaccataaa | 60 |
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aactttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |
| ggatcctata acttatttag cggtagcgtc agcaatgaat tcagcagcag cgaaactcgc | 420 |
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |
| cacacatacg agaatgaaac cattgccaag gccagctacg aagccttaac tgggcagatc | 720 |
| tctgctgaga ctgcggctaa atatcgccaa agcatgtcgt cgttctccca gaactccgat | 780 |
| attcacaaaa ttgtggtcgg cggagacgga gtcgcgggcg cgaaagtgta tagcggtgac | 840 |
| aaggcggatt tcgatgcttg ggctgacacc gtggggacgt tccagatttt tgtggacttt | 900 |
| gttagcagcg ttcctatgtt gggaatttgg gaactgtgca agatgacgc gcaggcgaaa | 960 |
| aagatggaag attactataa taatacgtgg gccccgcgga aaagcaaaga ggctcaaatt | 1020 |

```
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctggcat atcataaagc ccgttatagc gcttactcag aaaacaaaga ttgcgtttct    1200
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgagggggc cggaggtgag    1440
tacatttata tcgcatactc caaaggggct taa                                 1473

<210> SEQ ID NO 20
<211> LENGTH: 1473
<212> TYPE: DNA
<213> ORGANISM: artificial sequence
<220> FEATURE:
<223> OTHER INFORMATION: Woodsholea maritima

<400> SEQUENCE: 20
atgaaaagct tggatcacgt tgctcatcag aacttactga atgaaccgac tcaccataaa     60
agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aacttttga ttggcaaagc gcgccatcag aaccggtcat ttttaacccc     240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa     960 aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga tgcagtttct    1200
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgagggggc cggaggtgag    1440
tacatttata tcgcatactc caaaggggct taa                                 1473

<210> SEQ ID NO 21
```

<211> LENGTH: 1473
<212> TYPE: DNA
<213> ORGANISM: artificial sequence
<220> FEATURE:
<223> OTHER INFORMATION: Woodsholea maritima

<400> SEQUENCE: 21

| | |
|---|---|
| atgaaaagct tggatcacgt tgctcatcag aacttactga atgaaccgac tcaccataaa | 60 |
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aacttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |
| ggatcctata acttatttag cggtagcgtc agcaatgaat tcagcagcag cgaaactcgc | 420 |
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |
| cacacatacg agaatgaaac cattgccaag gccagctacg aagccttaac tgggcagatc | 720 |
| tctgctgaga ctgcggctaa atatcgccaa agcatgtcgt cgttctccca gaactccgat | 780 |
| attcacaaaa ttgtggtcgg cggagacgga gtcgcgggcg cgaaagtgta tagcggtgac | 840 |
| aaggcggatt tcgatgcttg gctgacaccc gtggggacgt ctccagatct tgtgactttt | 900 |
| gttagcagcg ttcctatgtt gggaatttgg gaactgtgca agatgacgc gcaggcgaaa | 960 |
| aagatggaag attactataa taatacgtgg gccccgcgga aaagcaaaga ggctcaaatt | 1020 |
| tatgctgatt atatcgacgc agtcgaagtg atccagagta attcttcggg ggttcgccct | 1080 |
| cccagtggat atacgaaaat tgattacgac ctcaataaag gcgccggtgg ggattatatc | 1140 |
| tacctgttat atcataaagc ccgttatagc gcttactcag aaaacaaaga ttgcgtttct | 1200 |
| gatttaatta ttattaaggg aaacggagca cgcgccccga gcggttatac gaaaattgat | 1260 |
| gtggatttga atgaggatgc aggtggaaaa tacctgtatt tatgctacaa gaagcaaagt | 1320 |
| tacgacaatg tggaagcaat caaggggctg gcggtagttg gtggtgacaa ttcgcatacc | 1380 |
| cctgctccgt acggttaccg tcggattgac accgatgtta acgaggggc cggaggtgag | 1440 |
| tacatttata tctgttactc caaaggggct taa | 1473 |

<210> SEQ ID NO 22
<211> LENGTH: 1473
<212> TYPE: DNA
<213> ORGANISM: artificial sequence
<220> FEATURE:
<223> OTHER INFORMATION: Woodsholea maritima

<400> SEQUENCE: 22

| | |
|---|---|
| atgaaaagct tggatcacgt tgctcatcag aacttactga atgaaccgac tcaccataaa | 60 |
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aacttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |

```
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa    960 aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga tttagtttct    1200
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgagggggc cggaggtgag    1440
tacatttata tctgttactc caaaggggct taa                                 1473

<210> SEQ ID NO 23
<211> LENGTH: 1473
<212> TYPE: DNA
<213> ORGANISM: artificial sequence
<220> FEATURE:
<223> OTHER INFORMATION: Woodsholea maritima

<400> SEQUENCE: 23
atgaaaagct tggatcacgt tgctcatcag aacttactga tgaaccgac tcaccataaa      60 agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aacttttttga ttggcaaagc gcgccatcag aaccggtcct ctttaacccc    240
gattacctcg ctccgaaagc tgtgtcagta caacaaaatg atgaagcccg gtttacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
```

```
gttagcagcg ttcctatgtt gggaatttgg gaactgtgca agatgacgc gcaggcgaaa       960 aagatggaag attactataa taatacgtgg gccccgcgga aaagcaaaga ggctcaaatt      1020
tatgctgatt atatcgacgc agtcgaagtg atccagagta attcttcggg ggttcgccct      1080
cccagtggat atacgaaaat tgattacgac ctcaataaag gcgccggtgg ggattatatc      1140
tacctgtgtt atcataaagc ccgttatagc gcttactcag aaaacaaaga ttgcgtttct      1200
gatttaatta ttattaaggg aaacggagca cgcgccccga gcggttatac gaaaattgat      1260
gtggatttga atgaggatgc aggtggaaaa tacctgtatt tatgctacaa gaagcaaagt      1320
tacgacaatg tggaagcaat caggggctg gcggtagttg gtggtgacaa ttcgcatacc       1380
cctgctccgt acggttaccg tcggattgac accgatgtta acgagggggc cggaggtgag      1440
tacatttata tctgttactc caaaggggct taa                                   1473
```

<210> SEQ ID NO 24
<211> LENGTH: 1473
<212> TYPE: DNA
<213> ORGANISM: artificial sequence
<220> FEATURE:
<223> OTHER INFORMATION: Woodsholea maritima

<400> SEQUENCE: 24

```
atgaaaagct tggatcacgt tgctcatcag aacttactga atgaaccgac tcaccataaa       60
agcaatacca aggcggcgct gatgcgtcat caggaaaacc tggttgaacg ctatctgccg      120
ggtgtggagg tgattggggc aggttacaac cctttcggcg tatacgcgtc cactgactca      180
gttactgtgc aactttttga ttggcaaagc gcgccatcag aaccggtcat ttttaaccc       240 gattacattg ctccgaaagc tgtgtcagta caacaaaatg atgaagcccg gtatacgaac      300
gttagcggca aaacaatcaa cacgtttcaa aaaaacttct ccctgaaagt tactgtcgcg      360
ggatcctata acttatttag cggtagcgtc agcaatgaat tcagcagcag cgaaactcgc      420
aatgcagaaa acgaatttag ccgcatccaa cagagcatcc gcgtctggtc tctgcgcctc      480
gcgtacacgg attccctgcg tgaatattta aaagcggacg ttcgcgatta tatcgatagc      540
attcaatcag atgcgcagat tgaaattctg tttgatcgtt acgggtcaca tttccttacc      600
ggcgtggtga tgggtggcgc agcaatcatg gcgtcttcga ccaataaagt acaggtggac      660
cacacatacg agaatgaaac cattgccaag gccagctacg aagccttaac tgggcagatc      720
tctgctgaga ctgcggctaa atttcgccaa agcatgtcgt cgttctccca gaactccgat      780
attcacaaac tcgtggtcgg cggagacgga gtcgcgggcg cgaaagtgtt tagcggtgac      840
aaggcggatt cgatgcttg ggctgacacc gtggggacgt ctccagattt tgtggacttt      900
gttagcagcg ttcctatgtt gggaatttgg gaactgtgca agatgacgc gcaggcgaaa      960 aagatggaag attactataa taatacgtgg gccccgcgga aaagcaaaga ggctcaaatt     1020
tatgctgatt atatcgacgc agtcgaagtg atccagagta attcttcggg ggttcgccct     1080
cccagtggat atacgaaaat tgattacgac ctcaataaag gcgccggtgg ggattatatc     1140
tacctgtgtt atcataaagc ccgttatagc gcttactcag aaaacaaaga ttgcgtttct     1200
gatttaatta ttattaaggg aaacggagca cgcgccccga gcggttatac gaaaattgat     1260
gtggatttga atgaggatgc aggtggaaaa tacctgtatt tatgctacaa gaagcaaagt     1320
tacgacaatg tggaagcaat caggggctg gcggtagttg gtggtgacaa ttcgcatacc      1380
cctgctccgt acggttaccg tcggattgac accgatgtta acgagggggc cggaggtgag     1440
tacatttata tctgttactc caaaggggct taa                                  1473
```

<210> SEQ ID NO 25
<211> LENGTH: 1473
<212> TYPE: DNA
<213> ORGANISM: artificial sequence
<220> FEATURE:
<223> OTHER INFORMATION: Woodsholea maritima

<400> SEQUENCE: 25

| | | | | |
|---|---|---|---|---|
| atgaaaagct | tggatcacgt | tgctcatcag | aacttactga | atgaaccgac tcaccataaa | 60 |
| agcaatacca | aggcggcgct | gatgcgtcat | caggaaaacc | tggttgaacg ctatctgccg | 120 |
| ggtgtggagg | tgattggggc | aggttacaac | cctttcggcg | tatacgcgtc cactgactca | 180 |
| gttactgtgc | aacttttga | ttggcaaagc | gcgccatcag | aaccggtcat ttttaacccc | 240 |
| gattacattg | ctccgaaagc | tgtgtcagta | caacaaaatg | atgaagcccg gtatacgaac | 300 |
| gttagcggca | aaacaatcaa | cacgtttcaa | aaaaacttct | ccctgaaagt tactgtcgcg | 360 |
| ggatcctata | acttatttag | cggtagcgtc | agcaatgaat | tcagcagcag cgaaactcgc | 420 |
| aatgcagaaa | acgaatttag | ccgcatccaa | cagagcatcc | gcgtctggtc tctgcgcctc | 480 |
| gcgtacacgg | attccctgcg | tgaatattta | aaagcggacg | ttcgcgatta tatcgatagc | 540 |
| attcaatcag | atgcgcagat | tgaaattctg | tttgatcgtt | acgggtcaca tttccttacc | 600 |
| ggcgtggtga | tgggtggcgc | agcaatcatg | gcgtcttcga | ccaataaagt acaggtggac | 660 |
| cacacatacg | agaatgaaac | cattgccaag | gccagctacg | aagccttaac tgggcagatc | 720 |
| tctgctgaga | ctgcggctaa | atatcgccaa | agcatgtcgt | cgttctccca gaactccgat | 780 |
| attcacaaaa | ttgtggtcgg | cggagacgga | gtcgcgggcg | cgaaagtgta tagcggtgac | 840 |
| aaggcggatt | tcgatgcttg | ggctgacacc | gtggggacgt | ctccagattt tgtggacttt | 900 |
| gttagcagcg | ttcctatgtt | gggaatttgg | gaactgtgca | agatgacgc gcaggcgaaa | 960 |
| aagatggaag | attactttaa | taatacgtgg | gccccgcgga | aaagcaaaga ggctcaactc | 1020 |
| tatgctgatt | atatcgacgc | agtcgaagtg | ctccagagta | attcttcggg ggttcgccct | 1080 |
| cccagtggat | atacgaaaat | tgattacgac | ctcaataaag | cgccggtgg ggattatatc | 1140 |
| tacctgtgtt | atcataaagc | ccgttatagc | gcttactcag | aaaacaaaga ttgcgtttct | 1200 |
| gatttaatta | ttattaaggg | aaacggagca | cgcgcccga gcggttatac gaaaattgat | 1260 |
| gtggatttga | atgaggatgc | aggtggaaaa | tacctgtatt | tatgctacaa gaagcaaagt | 1320 |
| tacgacaatg | tggaagcaat | caaggggctg | gcggtagttg | gtggtgacaa ttcgcatacc | 1380 |
| cctgctccgt | acggttaccg | tcggattgac | accgatgtta | acgaggggc cggaggtgag | 1440 |
| tacatttata | tctgttactc | caaaggggct | taa | | 1473 |

<210> SEQ ID NO 26
<211> LENGTH: 1473
<212> TYPE: DNA
<213> ORGANISM: artificial sequence
<220> FEATURE:
<223> OTHER INFORMATION: Woodsholea maritima

<400> SEQUENCE: 26

| | | | | |
|---|---|---|---|---|
| atgaaaagct | tggatcacgt | tgctcatcag | aacttactga | atgaaccgac tcaccataaa | 60 |
| agcaatacca | aggcggcgct | gatgcgtcat | caggaaaacc | tggttgaacg ctatctgccg | 120 |
| ggtgtggagg | tgattggggc | aggttacaac | cctttcggcg | tatacgcgtc cactgactca | 180 |
| gttactgtgc | aacttttga | ttggcaaagc | gcgccatcag | aaccggtcat ttttaacccc | 240 |

```
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcactcatg gcgtcttcga ccaataaagt acaggtggac    660
cacacatttg agaatgaaac cctcgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa    960 aagatggaag attactataa taatcgtggg cccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga ttgcgtttct    1200
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgaggggggc cggaggtgag    1440 tacatttata tctgttactc caaaggggct taa                                 1473

<210> SEQ ID NO 27
<211> LENGTH: 1473
<212> TYPE: DNA
<213> ORGANISM: artificial sequence
<220> FEATURE:
<223> OTHER INFORMATION: Woodsholea maritima

<400> SEQUENCE: 27
atgaaaagct tggatcacgt tgctcatcag aacttactga atgaaccgac tcaccataaa     60
agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aactttttga ttggcaaagc gcgccatcag aaccggtcat ttttaacccc    240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
```

```
aaggcggatt tcgatgcttg ggctgacacc gtggggacgt ctccagattt tgtggactttt      900 gttagcagcg ttcctatgtt gggaatttgg gaactgtgca aagatgacgc gcaggcgaaa      960
aagatggaag attactataa taatacgtgg gccccgcgga aaagcaaaga ggctcaaatt     1020
tatgctgatt atatcgacgc agtcgaagtg atccagagta attcttcggg ggttcgccct     1080
cccagtggat atacgaaaat tgattacgac ctcaataaag gcgccggtgg ggattatatc     1140
tacctgtgtt atcataaagc ccgttatagc gcttactcag aaaacaaaga ttgcgtttct     1200
gatttaatta ttattaaggg aaacggagca cgcgccccga gcggttatac gaaaattgat     1260
gtggatttga atgaggatgc aggtggaaaa tacctgtatt tatgctacaa gaagcaaagt     1320
tacgacaatg tggaagcact caaggggctg gcggtagttg gtggtgacaa ttcgcatacc     1380
cctgctccgt ttggttaccg tcggctcgac accgatgtta acgagggggc cggaggtgag     1440
tacatttata tctgttactc caaagggggct taa                                 1473
```

<210> SEQ ID NO 28
<211> LENGTH: 1473
<212> TYPE: DNA
<213> ORGANISM: artificial sequence
<220> FEATURE:
<223> OTHER INFORMATION: Woodsholea maritima

<400> SEQUENCE: 28

```
atgaaaagct tggatcacgt tgctcatcag aacttactga atgaaccgac tcaccataaa       60
agcaatacca aggcggcgct gatgcgtcat caggaaaaacc tggttgaacg ctatctgccg      120
ggtgtggagg tgattggggc aggttacaac cctttcggcg tatacgcgtc cactgactca      180
gttactgtgc aacttttttga ttggcaaagc gcgccatcag aaccggtcat ttttaacccc     240
gattacattg ctccgaaagc tgtgtcagta caacaaaatg atgaagcccg gtatacgaac     300
gttagcggca aaacaatcaa cacgtttcaa aaaaacttct ccctgaaagt tactgtcgcg     360
ggatcctata acttatttag cggtagcgtc agcaatgaat tcagcagcag cgaaactcgc     420
aatgcagaaa acgaatttag ccgcatccaa cagagcatcc gcgtctggtc tctgcgcctc     480
gcgtacacgg attccctgcg tgaatattta aaagcggacg ttcgcgatta tatcgatagc     540
attcaatcag atgcgcagat tgaaattctg tttgatcgtt acgggtcaca tttccttacc     600
ggcgtggtga tgggtggcgc agcaatcatg gcgtcttcga ccaataaagt acaggtggac     660
cacacatacg agaatgaaac cattgccaag gccagctacg aagccttaac tgggcagatc     720
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt tcgatgcttg ggctgacacc gtggggacgt ctccagattt tgtggactttt     900 gttagcagcg ttcctatgtt gggaatttgg gaactgtgca aagatgacgc gcaggcgaaa     960
aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga ttgcgtttct    1200
gatttaatta ttattaaggg aaacggagca cgcgccccga gcggttatac gaaaattgat    1260
gtggatttga atgaggatgc aggtggaaaa tacctgtatt tactgtacaa gaagcaaagt    1320
tacgacaatg tggaagcaat caaggggctg gcggtagttg gtggtgacaa ttcgcatacc    1380
```

```
cctgctccgt acggttaccg tcggattgac accgatgtta acgagggggc cggaggtgag    1440
tacatttata tctgttactc caaaggggct taa                                 1473

<210> SEQ ID NO 29
<211> LENGTH: 1473
<212> TYPE: DNA
<213> ORGANISM: artificial sequence
<220> FEATURE:
<223> OTHER INFORMATION: Woodsholea maritima

<400> SEQUENCE: 29
atgaaaagct tggatcacgt tgctcatcag aacttactga atgaaccgac tcaccataaa      60
agcaatacca aggcggcgct gatgcgtcat caggaaaacc tggttgaacg ctatctgccg     120
ggtgtggagg tgattggggc aggttacaac cctttcggcg tatacgcgtc cactgactca     180
gttactgtgc aacttttga ttggcaaagc gcgccatcag aaccggtcat ttttaacccc      240
gattacattg ctccgaaagc tgtgtcagta caacaaaatg atgaagcccg gtatacgaac     300
gttagcggca aacaatcaa cacgtttcaa aaaaacttct ccctgaaagt tactgtcgcg     360
ggatcctata acttatttag cggtagcgtc agcaatgaat tcagcagcag cgaaactcgc     420
aatgcagaaa acgaatttag ccgcatccaa cagagcatcc gcgtctggtc tctgcgcctc     480
gcgtacacgg attccctgcg tgaatattta aaagcggacg ttcgcgatta tatcgatagc     540
attcaatcag atgcgcagat tgaaattctg tttgatcgtt acgggtcaca tttccttacc     600
ggcgtggtga tgggtggcgc agcaatcatg gcgtcttcga ccaataaagt acaggtggac     660
cacacatacg agaatgaaac cattgccaag gccagctacg aagccttaac tgggcagatc     720
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt tcgatgcttg ggctgacacc gtggggacgt ctccagattt tgtggacttt     900
gttagcagcg ttcctatgtt gggaatttgg gaactgtgca agatgacgc gcaggcgaaa      960 aagatggaag attactataa taatacgtgg gccccgcgga aaagcaaaga ggctcaaatt    1020
tatgctgatt atatcgacgc agtcgaagtg atccagagta attcttcggg ggttcgcct     1080 cccagtggat atacgaaaat tgattacgac ctcaataaag gcgccggtgg ggattatatc    1140
tacctgtgtt atcataaagc ccgttatagc gcttactcag aaaacaaaga ttgcgtttct    1200
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgagggggc cggaggtgag    1440
tacatttata tcttatactc caaaggggct taa                                 1473

<210> SEQ ID NO 30
<211> LENGTH: 1473
<212> TYPE: DNA
<213> ORGANISM: artificial sequence
<220> FEATURE:
<223> OTHER INFORMATION: Woodsholea maritima

<400> SEQUENCE: 30
atgaaaagct tggatcacgt tgctcatcag aacttactga atgaaccgac tcaccataaa      60
agcaatacca aggcggcgct gatgcgtcat caggaaaacc tggttgaacg ctatctgccg     120
ggtgtggagg tgattggggc aggttacaac cctttcggcg tatacgcgtc cactgactca     180
```

```
gttactgtgc aacttttgga ttggcaaagc gcgccatcag aaccggtcat ttttaacccc      240
gattacattg ctccgaaagc tgtgtcagta caacaaaatg atgaagcccg gtatacgaac      300
gttagcggca aaacaatcaa cacgtttcaa aaaaacttct ccctgaaagt tactgtcgcg      360
ggatcctata acttatttag cggtagcgtc agcaatgaat tcagcagcag cgaaactcgc      420
aatgcagaaa acgaatttag ccgcatccaa cagagcatcc gcgtctggtc tctgcgcctc      480
gcgtacacgg attccctgcg tgaatattta aaagcggacg ttcgcgatta tatcgatagc      540
attcaatcag atgcgcagat tgaaattctg tttgatcgtt acgggtcaca tttccttacc      600
ggcgtggtga tgggtggcgc agcaatcatg gcgtcttcga ccaataaagt acaggtggac      660
cacacatacg agaatgaaac cattgccaag gccagctacg aagccttaac tgggcagatc      720
tctgctgaga ctgcggctaa atatcgccaa agcatgtcgt cgttctccca gaactccgat      780
attcacaaaa ttgtggtcgg cggagacgga gtcgcgggcg cgaaagtgta tagcggtgac      840
aaggcggatt tcgatgcttg ggctgacacc gtggggacgc tccagatttt tgtggacttt      900
gttagcagcg ttcctatgtt gggaatttgg gaactgtgca aagatgacgc gcaggcgaaa      960
aagatggaag attactataa taatacgtgg gccccgcgga aaagcaaaga ggctcaaatt     1020
tatgctgatt atatcgacgc agtcgaagtg atccagagta attcttcggg ggttcgccct     1080
cccagtggat atacgaaaat tgattacgac ctcaataaag cgccggtgg ggattatatc      1140
tacctgtgtt atcataaagc ccgttatagc gcttactcag aaaacaaaga ttgcgtttct     1200
gatttactgt taattaaggg aaacggagca cgcgccccga gcggttatac gaaaattgat     1260
gtggatttga atgaggatgc aggtggaaaa tacctgtatt tatgctacaa gaagcaaagt     1320
tacgacaatg tggaagcaat caaggggctg gcggtagttg gtggtgacaa ttcgcatacc     1380
cctgctccgt acggttaccg tcggattgac accgatgtta acgagggggc cggaggtgag     1440
tacatttata tctgttactc caaaggggct taa                                  1473
```

<210> SEQ ID NO 31
<211> LENGTH: 1473
<212> TYPE: DNA
<213> ORGANISM: artificial sequence
<220> FEATURE:
<223> OTHER INFORMATION: Woodsholea maritima

<400> SEQUENCE: 31

```
atgaaaagct tggatcacgt tgctcatcag aacttactga atgaaccgac tcaccataaa       60
agcaatacca aggcggcgct gatgcgtcat caggaaaaacc tggttgaacg ctatctgccg      120
ggtgtggagg tgattggggc aggttacaac cctttcggcg tatacgcgtc cactgactca      180
gttactgtgc aacttttgga ttggcaaagc gcgccatcag aaccggtcat ttttaacccc      240
gattacattg ctccgaaagc tgtgtcagta caacaaaatg atgaagcccg gtatacgaac      300
gttagcggca aaacaatcaa cacgtttcaa aaaaacttct ccctgaaagt tactgtcgcg      360
ggatcctata acttatttag cggtagcgtc agcaatgaat tcagcagcag cgaaactcgc      420
aatgcagaaa acgaatttag ccgcatccaa cagagcatcc gcgtctggtc tctgcgcctc      480
gcgtacacgg attccctgcg tgaatattta aaagcggacg ttcgcgatta tatcgatagc      540
attcaatcag atgcgcagat tgaaattctg tttgatcgtt acgggtcaca tttccttacc      600
ggcgtggtga tgggtggcgc agcaatcatg gcgtcttcga ccaataaagt acaggtggac      660
cacacatacg agaatgaaac cattgccaag gccagctacg aagccttaac tgggcagatc      720
```

```
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa     960
aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaaacaaaga ttgcttatct   1200
gatttaatta ttattaaggg aaacggagca cgcgccccga gcggttatac gaaaattgat   1260
gtggatttga atgaggatgc aggtggaaaa tacctgtatt tatgctacaa gaagcaaagt   1320
tacgacaatg tggaagcaat caaggggctg gcggtagttg gtggtgacaa ttcgcatacc   1380
cctgctccgt acggttaccg tcggattgac accgatgtta acgaggggc cggaggtgag   1440
tacatttata tctgttactc caaaggggct taa                               1473

<210> SEQ ID NO 32
<211> LENGTH: 1473
<212> TYPE: DNA
<213> ORGANISM: artificial sequence
<220> FEATURE:
<223> OTHER INFORMATION: Woodsholea maritima

<400> SEQUENCE: 32
atgaaaagct tggatcacgt tgctcatcag aacttactga tgaaccgac tcaccataaa     60
agcaatacca aggcggcgct gatgcgtcat caggaaaacc tggttgaacg ctatctgccg    120
ggtgtggagg tgattgggc aggttacaac ccttcggcg tatacgcgtc cactgactca     180
gttactgtgc aactttttga ttggcaaagc gcgccatcag aaccggtcat ttttaacccc    240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa     960
aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaaacaaaga ttgcttttct   1200
gatttaatta ttattaaggg aaacggagca cgcgccccga gcggttatac gaaaattgat   1260
gtggatttga atgaggatgc aggtggaaaa tacctgtatt tatgctacaa gaagcaaagt   1320
```

```
tacgacaatg tggaagcaat caaggggctg gcggtagttg gtggtgacaa ttcgcatacc    1380
cctgctccgt acggttaccg tcggattgac accgatgtta acgaggggggc cggaggtgag    1440 tacatttata tctgttactc caaaggggct taa                                 1473

<210> SEQ ID NO 33
<211> LENGTH: 1473
<212> TYPE: DNA
<213> ORGANISM: artificial sequence
<220> FEATURE:
<223> OTHER INFORMATION: Woodsholea maritima

<400> SEQUENCE: 33
atgaaaagct tggatcacgt tgctcatcag aacttactga atgaaccgac tcaccataaa      60
agcaatacca aggcggcgct gatgcgtcat caggaaaacc tggttgaacg ctatctgccg     120
ggtgtggagg tgattggggc aggttacaac cctttcggcg tatacgcgtc cactgactca     180
gttactgtgc aactttttga ttggcaaagc gcgccatcag aaccggtcat ttttaacccc     240
gattacattg ctccgaaagc tgtgtcagta caacaaaatg atgaagcccg gtatacgaac     300
gttagcggca aaacaatcaa cacgtttcaa aaaaacttct ccctgaaagt tactgtcgcg     360
ggatcctata acttatttag cggtagcgtc agcaatgaat tcagcagcag cgaaactcgc     420
aatgcagaaa acgaatttag ccgcatccaa cagagcatcc gcgtctggtc tctgcgcctc     480
gcgtacacgg attccctgcg tgaatattta aaagcggacg ttcgcgatta tatcgatagc     540
attcaatcag atgcgcagat tgaaattctg tttgatcgtt acgggtcaca tttccttacc     600
ggcgtggtga tgggtggcgc agcaatcatg gcgtcttcga ccaataaagt acaggtggac     660
cacacatacg agaatgaaac cattgccaag gccagctacg aagccttaac tgggcagatc     720
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt tcgatgcttg gctgacaccc gtggggacgt ctccagattt tgtggacttt     900
gttagcagcg ttcctatgtt gggaatttgg gaactgtgca agatgacgc gcaggcgaaa     960 aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga ttttgtttct    1200
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgaggggggc cggaggtgag    1440 tacatttata tctgttactc caaaggggct taa                                 1473

<210> SEQ ID NO 34
<211> LENGTH: 1473
<212> TYPE: DNA
<213> ORGANISM: artificial sequence
<220> FEATURE:
<223> OTHER INFORMATION: Woodsholea maritima

<400> SEQUENCE: 34
atgaaaagct tggatcacgt tgctcatcag aacttactga atgaaccgac tcaccataaa      60
```

| | |
|---|---|
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aacttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |
| ggatcctata acttatttag cggtagcgtc agcaatgaat tcagcagcag cgaaactcgc | 420 |
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |
| cacacatacg agaatgaaac cattgccaag gccagctacg aagccttaac tgggcagatc | 720 |
| tctgctgaga ctgcggctaa atatcgccaa agcatgtcgt cgttctccca gaactccgat | 780 |
| attcacaaaa ttgtggtcgg cggagacgga gtcgcgggcg cgaaagtgta tagcggtgac | 840 |
| aaggcggatt tcgatgcttg ggctgacacc gtggggacgt ctccagattt tgtggacttt | 900 |
| gttagcagcg ttcctatgtt gggaatttgg gaactgtgca agatgacgc gcaggcgaaa | 960 |
| aagatggaag attactataa taatacgtgg gccccgcgga aaagcaaaga ggctcaaatt | 1020 |
| tatgctgatt atatcgacgc agtcgaagtg atccagagta attcttcggg ggttcgccct | 1080 |
| cccagtggat atacgaaaat tgattacgac ctcaataaag gcgccggtgg ggattatatc | 1140 |
| tacctgtgtt atcataaagc ccgttatagc gcttactcag aaaacaaaga ttacgtttct | 1200 |
| gatttaatta ttattaaggg aaacggagca cgcgccccga gcggttatac gaaaattgat | 1260 |
| gtggatttga atgaggatgc agtgaaaaa tacctgtatt tatgctacaa gaagcaaagt | 1320 |
| tacgacaatg tggaagcaat caggggctg gcggtagttg gtggtgacaa ttcgcatacc | 1380 |
| cctgctccgt acggttaccg tcggattgac accgatgtta acgagggggc cggaggtgag | 1440 |
| tacatttata tctgttactc caaagggggct taa | 1473 |

<210> SEQ ID NO 35
<211> LENGTH: 1473
<212> TYPE: DNA
<213> ORGANISM: artificial sequence
<220> FEATURE:
<223> OTHER INFORMATION: Woodsholea maritima

<400> SEQUENCE: 35

| | |
|---|---|
| atgaaaagct tggatcacgt tgctcatcag aacttactga atgaaccgac tcaccataaa | 60 |
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aacttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |
| ggatcctata acttatttag cggtagcgtc agcaatgaat tcagcagcag cgaaactcgc | 420 |
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |

```
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa     960 aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaaacaaaga tattgttcct   1200
gatttaatta ttattaaggg aaacggagca cgcgccccga gcggttatac gaaaattgat   1260
gtggatttga atgaggatgc aggtggaaaa tacctgtatt tatgctacaa gaagcaaagt   1320
tacgacaatg tggaagcaat caaggggctg gcggtagttg gtggtgacaa ttcgcatacc   1380
cctgctccgt acggttaccg tcggattgac accgatgtta acgagggggc cggaggtgag   1440
tacatttata tctgttactc caaagggggct taa                                 1473

<210> SEQ ID NO 36
<211> LENGTH: 1473
<212> TYPE: DNA
<213> ORGANISM: artificial sequence
<220> FEATURE:
<223> OTHER INFORMATION: Woodsholea maritima

<400> SEQUENCE: 36
atgaaaagct tggatcacgt tgctcatcag aacttactga tgaaccgac tcaccataaa      60 agcaatacca aggcggcgct gatgcgtcat caggaaaacc tggttgaacg ctatctgccg    120
ggtgtggagg tgattggggc aggttacaac ccttttcggcg tatacgcgtc cactgactca    180
gttactgtgc aacttttttga ttggcaaagc gcgccatcag aaccggtcat ttttaacccc    240
gattacattg ctccgaaagc tgtgtcagta caacaaaatg atgaagcccg gtatacgaac     300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa     960 aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaaacaaaga tattgttcct   1200
```

-continued

```
gatttaatta ttattaaggg aaacggagca cgcgccccga gcggttatac gaaaattgat    1260
gtggatttga atgaggatgc aggtggaaaa tacctgtatt tatgctacaa gaagcaaagt    1320
tacgacaatg tggaagcaat caaggggctg gcggtagttg gtggtgacaa ttcgcatacc    1380
cctgctccgt acggttaccg tcggattgac accgatgtta acgagggggc cggaggtgag    1440
tacatttata tctgttactc caaaggggct taa                                 1473
```

<210> SEQ ID NO 37
<211> LENGTH: 490
<212> TYPE: PRT
<213> ORGANISM: artificial sequence
<220> FEATURE:
<223> OTHER INFORMATION: Woodsholea maritima

<400> SEQUENCE: 37

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Phe Val Ser Ser Val
    290                 295                 300

Pro Met Leu Gly Ile Trp Glu Leu Cys Lys Asp Asp Ala Gln Ala Lys
305                 310                 315                 320
```

```
Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Ser Tyr Ser Lys Gly Ala
                485                 490

<210> SEQ ID NO 38
<211> LENGTH: 490
<212> TYPE: PRT
<213> ORGANISM: artificial sequence
<220> FEATURE:
<223> OTHER INFORMATION: Woodsholea maritima

<400> SEQUENCE: 38

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190
```

```
Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
                260                 265                 270

Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
        290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
                340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Asp Tyr Ile Tyr Leu Cys Tyr
        370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
                420                 425                 430

Tyr Leu Ser Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
        450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 39
<211> LENGTH: 490
<212> TYPE: PRT
<213> ORGANISM: artificial sequence
<220> FEATURE:
<223> OTHER INFORMATION: Woodsholea maritima

<400> SEQUENCE: 39

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
50                  55                  60
```

```
Leu Phe Asp Trp Gln Ser Ala Pro Ser Glu Pro Val Ile Phe Asn Pro
 65                  70                  75                  80

Asp Tyr Ile Ala Pro Lys Ala Val Ser Gln Gln Asn Asp Glu Ala
                 85                  90                  95

Arg Tyr Thr Asn Val Ser Gly Lys Thr Ile Asn Thr Phe Gln Lys Asn
                100                 105                 110

Phe Ser Leu Lys Val Thr Val Ala Gly Ser Tyr Asn Leu Phe Ser Gly
            115                 120                 125

Ser Val Ser Asn Glu Phe Ser Ser Glu Thr Arg Asn Ala Glu Asn
        130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
                180                 185                 190

Arg Tyr Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Ser Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480
```

```
Tyr Ile Tyr Ile Cys Tyr Ser Lys Gly Ala
                485                 490

<210> SEQ ID NO 40
<211> LENGTH: 490
<212> TYPE: PRT
<213> ORGANISM: artificial sequence
<220> FEATURE:
<223> OTHER INFORMATION: Woodsholea maritima

<400> SEQUENCE: 40

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
        50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Gly Val Ile Gln
            340                 345                 350
```

```
Ser Asn Ser Ser Gly Val Arg Pro Ser Gly Tyr Thr Lys Ile Asp
        355                 360                 365

Tyr Asp Leu Asn Lys Gly Ala Gly Gly Asp Tyr Ile Tyr Leu Ser Tyr
370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Lys Tyr Leu
                420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 41
<211> LENGTH: 490
<212> TYPE: PRT
<213> ORGANISM: artificial sequence
<220> FEATURE:
<223> OTHER INFORMATION: Woodsholea maritima

<400> SEQUENCE: 41

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220
```

```
Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
            245                 250                 255

Gln Asn Ser Asp Ile His Lys Ile Val Val Gly Gly Asp Gly Val Ala
        260                 265                 270

Gly Ala Lys Val Tyr Ser Gly Asp Lys Ala Asp Phe Asp Ala Trp Ala
    275                 280                 285

Asp Thr Val Gly Thr Ser Pro Asp Phe Val Asp Phe Val Ser Ser Val
290                 295                 300

Pro Met Leu Gly Ile Trp Glu Leu Ser Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
        355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 42
<211> LENGTH: 490
<212> TYPE: PRT
<213> ORGANISM: artificial sequence
<220> FEATURE:
<223> OTHER INFORMATION: Woodsholea maritima

<400> SEQUENCE: 42

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95
```

Arg Tyr Thr Asn Val Ser Gly Lys Thr Ile Asn Thr Phe Gln Lys Asn
                100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Lys Ala Asp Val Arg Asp
                165                 170                 175

Tyr Ile Asp Ser Ile Gln Ser Asp Ala Gln Ile Glu Ile Leu Phe Asp
                180                 185                 190

Arg Trp Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 43
<211> LENGTH: 490
<212> TYPE: PRT

<213> ORGANISM: artificial sequence
<220> FEATURE:
<223> OTHER INFORMATION: Woodsholea maritima

<400> SEQUENCE: 43

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Phe Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
        355                 360                 365

Tyr Asp Leu Asn Lys Gly Ala Gly Gly Asp Tyr Ile Tyr Leu Cys Tyr
370                 375                 380

His Lys Ala Arg Tyr Ser Ala Tyr Ser Glu Asn Lys Asp Cys Val Ser
```

```
                    385                 390                 395                 400
Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
                420                 425                 430

Tyr Leu Cys Tyr Lys Lys Gln Ser Tyr Asp Asn Val Glu Ala Ile Lys
                435                 440                 445

Gly Leu Ala Val Val Gly Gly Asp Asn Ser His Thr Pro Ala Pro Tyr
                450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 44
<211> LENGTH: 490
<212> TYPE: PRT
<213> ORGANISM: artificial sequence
<220> FEATURE:
<223> OTHER INFORMATION: Woodsholea maritima

<400> SEQUENCE: 44

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
        50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
```

-continued

```
            260                 265                 270
Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
            290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                    325                 330                 335

Glu Ala Gln Ile Tyr Ala Asp Tyr Ile Asp Ala Val Glu Val Ile Gln
                340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Gly Asp Tyr Ile Tyr Leu Cys Tyr
            370                 375                 380

His Lys Ala Arg Tyr Ser Ala Tyr Ser Glu Asn Leu Asp Cys Val Ser
385                 390                 395                 400

Asp Leu Ile Ile Ile Lys Gly Asn Gly Ala Arg Ala Pro Ser Gly Tyr
                    405                 410                 415

Thr Lys Ile Asp Val Asp Leu Asn Glu Asp Ala Gly Gly Lys Tyr Leu
                420                 425                 430

Tyr Leu Cys Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                    485                 490

<210> SEQ ID NO 45
<211> LENGTH: 490
<212> TYPE: PRT
<213> ORGANISM: artificial sequence
<220> FEATURE:
<223> OTHER INFORMATION: Woodsholea maritima

<400> SEQUENCE: 45

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
```

```
            130                 135                 140
Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
        355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Leu Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490
```

<210> SEQ ID NO 46
<211> LENGTH: 490
<212> TYPE: PRT
<213> ORGANISM: artificial sequence
<220> FEATURE:
<223> OTHER INFORMATION: Woodsholea maritima

<400> SEQUENCE: 46

Met Lys Ser Leu Asp His Val Ala His Gln Asn Leu Leu Asn Glu Pro

-continued

```
1               5                   10                  15
Thr His His Lys Ser Asn Thr Lys Ala Ala Leu Met Arg His Gln Glu
                20                  25                  30
Asn Leu Val Glu Arg Tyr Leu Pro Gly Val Glu Val Ile Gly Ala Gly
                35                  40                  45
Tyr Asn Pro Phe Gly Val Tyr Ala Ser Thr Asp Ser Val Thr Val Gln
                50                  55                  60
Leu Phe Asp Trp Gln Ser Ala Pro Ser Glu Pro Val Ile Phe Asn Pro
65                  70                  75                  80
Asp Tyr Ile Ala Pro Lys Ala Val Ser Gln Gln Asn Asp Glu Ala
                85                  90                  95
Arg Tyr Thr Asn Val Ser Gly Lys Thr Ile Asn Thr Phe Gln Lys Asn
                100                 105                 110
Phe Ser Leu Lys Val Thr Val Ala Gly Ser Tyr Asn Leu Phe Ser Gly
                115                 120                 125
Ser Val Ser Asn Glu Phe Ser Ser Ser Glu Thr Arg Asn Ala Glu Asn
                130                 135                 140
Glu Phe Ser Arg Ile Gln Gln Ser Ile Arg Val Trp Ser Leu Arg Leu
145                 150                 155                 160
Ala Tyr Thr Asp Ser Leu Arg Glu Tyr Leu Lys Ala Asp Val Arg Asp
                165                 170                 175
Tyr Ile Asp Ser Ile Gln Ser Asp Ala Gln Ile Glu Ile Leu Phe Asp
                180                 185                 190
Arg Tyr Gly Ser His Phe Leu Thr Gly Val Val Met Gly Gly Ala Ala
                195                 200                 205
Ile Met Ala Ser Ser Thr Asn Lys Val Gln Val Asp His Thr Tyr Glu
                210                 215                 220
Asn Glu Thr Ile Ala Lys Ala Ser Tyr Glu Ala Leu Thr Gly Gln Ile
225                 230                 235                 240
Ser Ala Glu Thr Ala Lys Tyr Arg Gln Ser Met Ser Ser Phe Ser
                245                 250                 255
Gln Asn Ser Asp Ile His Lys Ile Val Val Gly Gly Asp Gly Val Ala
                260                 265                 270
Gly Ala Lys Val Tyr Ser Gly Asp Lys Ala Asp Phe Asp Ala Trp Ala
                275                 280                 285
Asp Thr Val Gly Thr Ser Pro Asp Phe Val Asp Phe Val Ser Ser Val
                290                 295                 300
Pro Met Leu Gly Ile Trp Glu Leu Cys Lys Asp Asp Ala Gln Ala Lys
305                 310                 315                 320
Lys Met Glu Asp Tyr Tyr Asn Asn Thr Trp Ala Pro Arg Lys Ser Lys
                325                 330                 335
Glu Ala Gln Ile Tyr Ala Asp Tyr Ile Asp Ala Val Glu Val Ile Gln
                340                 345                 350
Ser Asn Ser Ser Gly Val Arg Pro Pro Ser Gly Tyr Thr Lys Ile Asp
                355                 360                 365
Tyr Asp Leu Asn Lys Gly Ala Gly Asp Tyr Ile Tyr Leu Ser Tyr
                370                 375                 380
His Lys Ala Arg Tyr Ser Ala Tyr Ser Glu Asn Lys Asp Cys Val Ser
385                 390                 395                 400
Asp Leu Ile Ile Ile Lys Gly Asn Gly Ala Arg Ala Pro Ser Gly Tyr
                405                 410                 415
Thr Lys Ile Asp Val Asp Leu Asn Glu Asp Ala Gly Gly Lys Tyr Leu
                420                 425                 430
```

```
Tyr Leu Cys Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Ser Tyr Ser Lys Gly Ala
            485                 490

<210> SEQ ID NO 47
<211> LENGTH: 490
<212> TYPE: PRT
<213> ORGANISM: artificial sequence
<220> FEATURE:
<223> OTHER INFORMATION: Woodsholea maritima

<400> SEQUENCE: 47

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Gln Gln Asn Asp Glu Ala
            85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
            115                 120                 125

Ser Val Ser Asn Glu Phe Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
290                 295                 300
```

```
Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Ser Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Ser Tyr Ser Lys Gly Ala
                485                 490

<210> SEQ ID NO 48
<211> LENGTH: 490
<212> TYPE: PRT
<213> ORGANISM: artificial sequence
<220> FEATURE:
<223> OTHER INFORMATION: Woodsholea maritima

<400> SEQUENCE: 48

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175
```

```
Tyr Ile Asp Ser Ile Gln Ser Asp Ala Gln Ile Glu Ile Leu Phe Asp
                180                 185                 190

Arg Tyr Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
        210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Ser Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Ser Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 49
<211> LENGTH: 490
<212> TYPE: PRT
<213> ORGANISM: artificial sequence
<220> FEATURE:
<223> OTHER INFORMATION: Woodsholea maritima

<400> SEQUENCE: 49

Met Lys Ser Leu Asp His Val Ala His Gln Asn Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45
```

```
Tyr Asn Pro Phe Gly Val Tyr Ala Ser Thr Asp Ser Val Thr Val Gln
     50                  55                  60

Leu Phe Asp Trp Gln Ser Ala Pro Ser Glu Pro Val Ile Phe Asn Pro
 65                  70                  75                  80

Asp Tyr Ile Ala Pro Lys Ala Val Ser Val Gln Gln Asn Asp Glu Ala
                 85                  90                  95

Arg Tyr Thr Asn Val Ser Gly Lys Thr Ile Asn Thr Phe Gln Lys Asn
             100                 105                 110

Phe Ser Leu Lys Val Thr Val Ala Gly Ser Tyr Asn Leu Phe Ser Gly
         115                 120                 125

Ser Val Ser Asn Glu Phe Ser Ser Glu Thr Arg Asn Ala Glu Asn
     130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                 165                 170                 175

Tyr Ile Asp Ser Ile Gln Ser Asp Ala Gln Ile Glu Ile Leu Phe Asp
             180                 185                 190

Arg Tyr Gly Ser His Phe Leu Thr Gly Val Val Met Gly Gly Ala Ala
         195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                 245                 250                 255

Gln Asn Ser Asp Ile His Lys Ile Val Val Gly Gly Asp Gly Val Ala
             260                 265                 270

Gly Ala Lys Val Tyr Ser Gly Asp Lys Ala Asp Phe Asp Ala Trp Ala
         275                 280                 285

Asp Thr Val Gly Thr Ser Pro Asp Phe Val Asp Phe Val Ser Ser Val
     290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                 325                 330                 335

Glu Ala Gln Ile Tyr Ala Asp Tyr Ile Asp Ala Val Glu Val Ile Gln
             340                 345                 350

Ser Asn Ser Ser Gly Val Arg Pro Pro Ser Gly Tyr Thr Lys Ile Asp
         355                 360                 365

Tyr Asp Leu Asn Lys Gly Ala Gly Asp Tyr Ile Tyr Leu Cys Tyr
     370                 375                 380

His Lys Ala Arg Tyr Ser Ala Tyr Ser Glu Asn Lys Asp Ser Val Ser
385                 390                 395                 400

Asp Leu Ile Ile Ile Lys Gly Asn Gly Ala Arg Ala Pro Ser Gly Tyr
                 405                 410                 415

Thr Lys Ile Asp Val Asp Leu Asn Glu Asp Ala Gly Lys Tyr Leu
             420                 425                 430

Tyr Leu Cys Tyr Lys Lys Gln Ser Tyr Asp Asn Val Glu Ala Ile Lys
         435                 440                 445

Gly Leu Ala Val Val Gly Gly Asp Asn Ser His Thr Pro Ala Pro Tyr
     450                 455                 460
```

Gly Tyr Arg Arg Ile Asp Thr Asp Val Asn Glu Ala Gly Gly Glu
465                 470                 475                 480

Tyr Ile Tyr Ile Ser Tyr Ser Lys Gly Ala
            485                 490

<210> SEQ ID NO 50
<211> LENGTH: 490
<212> TYPE: PRT
<213> ORGANISM: artificial sequence
<220> FEATURE:
<223> OTHER INFORMATION: Woodsholea maritima

<400> SEQUENCE: 50

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

```
Glu Ala Gln Ile Tyr Ala Asp Tyr Ile Asp Ala Val Glu Val Ile Gln
                340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Gly Asp Tyr Ile Tyr Leu Ser Tyr
        370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Ser Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Ser Tyr Ser Lys Gly Ala
                485                 490

<210> SEQ ID NO 51
<211> LENGTH: 490
<212> TYPE: PRT
<213> ORGANISM: artificial sequence
<220> FEATURE:
<223> OTHER INFORMATION: Woodsholea maritima

<400> SEQUENCE: 51

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205
```

```
Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Ser Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
        355                 360                 365

Tyr Asp Leu Asn Lys Gly Ala Gly Asp Tyr Ile Tyr Leu Ser Tyr
    370                 375                 380

His Lys Ala Arg Tyr Ser Ala Tyr Ser Glu Asn Lys Asp Ser Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Ser Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Ser Tyr Ser Lys Gly Ala
                485                 490
```

<210> SEQ ID NO 52
<211> LENGTH: 490
<212> TYPE: PRT
<213> ORGANISM: artificial sequence
<220> FEATURE:
<223> OTHER INFORMATION: Woodsholea maritima

<400> SEQUENCE: 52

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80
```

```
Asp Tyr Ile Ala Pro Lys Ala Val Ser Val Gln Gln Asn Asp Glu Ala
                85                  90                  95
Arg Tyr Thr Asn Val Ser Gly Lys Thr Ile Asn Thr Phe Gln Lys Asn
            100                 105                 110
Phe Ser Leu Lys Val Thr Val Ala Gly Ser Tyr Asn Leu Phe Ser Gly
            115                 120                 125
Ser Val Ser Asn Glu Phe Ser Ser Glu Thr Arg Asn Ala Glu Asn
130                 135                 140
Glu Phe Ser Arg Ile Gln Gln Ser Ile Arg Val Trp Ser Leu Arg Leu
145                 150                 155                 160
Ala Tyr Thr Asp Ser Leu Arg Glu Tyr Leu Lys Ala Asp Val Arg Asp
                165                 170                 175
Tyr Ile Asp Ser Ile Gln Ser Asp Ala Gln Ile Glu Ile Leu Phe Asp
                180                 185                 190
Arg Tyr Gly Ser His Phe Leu Thr Gly Val Val Met Gly Gly Ala Ala
                195                 200                 205
Ile Met Ala Ser Ser Thr Asn Lys Val Gln Val Asp His Thr Tyr Glu
            210                 215                 220
Asn Glu Thr Ile Ala Lys Ala Ser Tyr Glu Ala Leu Thr Gly Gln Ile
225                 230                 235                 240
Ser Ala Glu Thr Ala Ala Lys Tyr Arg Gln Ser Met Ser Ser Phe Ser
                245                 250                 255
Gln Asn Ser Asp Ile His Lys Ile Val Val Gly Gly Asp Gly Val Ala
                260                 265                 270
Gly Ala Lys Val Tyr Ser Gly Asp Lys Ala Asp Phe Asp Ala Trp Ala
                275                 280                 285
Asp Thr Val Gly Thr Ser Pro Asp Phe Val Asp Phe Val Ser Ser Val
            290                 295                 300
Pro Met Leu Gly Ile Trp Glu Leu Cys Lys Asp Asp Ala Gln Ala Lys
305                 310                 315                 320
Lys Met Glu Asp Tyr Tyr Asn Asn Thr Trp Ala Pro Arg Lys Ser Lys
                325                 330                 335
Glu Ala Gln Ile Tyr Ala Asp Tyr Ile Asp Ala Val Glu Val Ile Gln
                340                 345                 350
Ser Asn Ser Ser Gly Val Arg Pro Pro Ser Gly Tyr Thr Lys Ile Asp
            355                 360                 365
Tyr Asp Leu Asn Lys Gly Ala Gly Gly Asp Tyr Ile Tyr Leu Ala Tyr
            370                 375                 380
His Lys Ala Arg Tyr Ser Ala Tyr Ser Glu Asn Lys Asp Cys Val Ser
385                 390                 395                 400
Asp Leu Ile Ile Ile Lys Gly Asn Gly Ala Arg Ala Pro Ser Gly Tyr
                405                 410                 415
Thr Lys Ile Asp Val Asp Leu Asn Glu Asp Ala Gly Lys Tyr Leu
            420                 425                 430
Tyr Leu Cys Tyr Lys Gln Ser Tyr Asp Asn Val Glu Ala Ile Lys
                435                 440                 445
Gly Leu Ala Val Val Gly Gly Asp Asn Ser His Thr Pro Ala Pro Tyr
450                 455                 460
Gly Tyr Arg Arg Ile Asp Thr Asp Val Asn Glu Gly Ala Gly Gly Glu
465                 470                 475                 480
Tyr Ile Tyr Ile Ala Tyr Ser Lys Gly Ala
                485                 490
```

```
<210> SEQ ID NO 53
<211> LENGTH: 490
<212> TYPE: PRT
<213> ORGANISM: artificial sequence
<220> FEATURE:
<223> OTHER INFORMATION: Woodsholea maritima

<400> SEQUENCE: 53

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
```

```
            370                 375                 380
His Lys Ala Arg Tyr Ser Ala Tyr Ser Glu Asn Lys Asp Ala Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
                420                 425                 430

Tyr Leu Cys Tyr Lys Lys Gln Ser Tyr Asp Asn Val Glu Ala Ile Lys
                435                 440                 445

Gly Leu Ala Val Val Gly Gly Asp Asn Ser His Thr Pro Ala Pro Tyr
                450                 455                 460

Gly Tyr Arg Arg Ile Asp Thr Asp Val Asn Glu Gly Ala Gly Gly Glu
465                 470                 475                 480

Tyr Ile Tyr Ile Ala Tyr Ser Lys Gly Ala
                485                 490

<210> SEQ ID NO 54
<211> LENGTH: 490
<212> TYPE: PRT
<213> ORGANISM: artificial sequence
<220> FEATURE:
<223> OTHER INFORMATION: Woodsholea maritima

<400> SEQUENCE: 54

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
        50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
                100                 105                 110

Phe Ser Leu Lys Val Thr Val Ala Gly Ser Tyr Asn Leu Phe Ser Gly
                115                 120                 125

Ser Val Ser Asn Glu Phe Ser Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
                180                 185                 190

Arg Tyr Gly Ser His Phe Leu Thr Gly Val Val Met Gly Gly Ala Ala
                195                 200                 205

Ile Met Ala Ser Ser Thr Asn Lys Val Gln Val Asp His Thr Tyr Glu
                210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
```

```
            245                 250                 255
Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
        355                 360                 365

Tyr Asp Leu Asn Lys Gly Ala Gly Asp Tyr Ile Tyr Leu Leu Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 55
<211> LENGTH: 490
<212> TYPE: PRT
<213> ORGANISM: artificial sequence
<220> FEATURE:
<223> OTHER INFORMATION: Woodsholea maritima

<400> SEQUENCE: 55

Met Lys Ser Leu Asp His Val Ala His Gln Asn Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
```

```
            115                 120                 125
Ser Val Ser Asn Glu Phe Ser Ser Glu Thr Arg Asn Ala Glu Asn
    130                 135                 140
Glu Phe Ser Arg Ile Gln Gln Ser Ile Arg Val Trp Ser Leu Arg Leu
145                 150                 155                 160
Ala Tyr Thr Asp Ser Leu Arg Glu Tyr Leu Lys Ala Asp Val Arg Asp
                165                 170                 175
Tyr Ile Asp Ser Ile Gln Ser Asp Ala Gln Ile Glu Ile Leu Phe Asp
                180                 185                 190
Arg Tyr Gly Ser His Phe Leu Thr Gly Val Val Met Gly Gly Ala Ala
                195                 200                 205
Ile Met Ala Ser Ser Thr Asn Lys Val Gln Val Asp His Thr Tyr Glu
210                 215                 220
Asn Glu Thr Ile Ala Lys Ala Ser Tyr Glu Ala Leu Thr Gly Gln Ile
225                 230                 235                 240
Ser Ala Glu Thr Ala Ala Lys Tyr Arg Gln Ser Met Ser Ser Phe Ser
                245                 250                 255
Gln Asn Ser Asp Ile His Lys Ile Val Val Gly Gly Asp Gly Val Ala
                260                 265                 270
Gly Ala Lys Val Tyr Ser Gly Asp Lys Ala Asp Phe Asp Ala Trp Ala
                275                 280                 285
Asp Thr Val Gly Thr Ser Pro Asp Phe Val Asp Phe Val Ser Ser Val
                290                 295                 300
Pro Met Leu Gly Ile Trp Glu Leu Cys Lys Asp Asp Ala Gln Ala Lys
305                 310                 315                 320
Lys Met Glu Asp Tyr Tyr Asn Asn Thr Trp Ala Pro Arg Lys Ser Lys
                325                 330                 335
Glu Ala Gln Ile Tyr Ala Asp Tyr Ile Asp Ala Val Glu Val Ile Gln
                340                 345                 350
Ser Asn Ser Ser Gly Val Arg Pro Pro Ser Gly Tyr Thr Lys Ile Asp
                355                 360                 365
Tyr Asp Leu Asn Lys Gly Ala Gly Gly Asp Tyr Ile Tyr Leu Cys Tyr
                370                 375                 380
His Lys Ala Arg Tyr Ser Ala Tyr Ser Glu Asn Lys Asp Leu Val Ser
385                 390                 395                 400
Asp Leu Ile Ile Ile Lys Gly Asn Gly Ala Arg Ala Pro Ser Gly Tyr
                405                 410                 415
Thr Lys Ile Asp Val Asp Leu Asn Glu Asp Ala Gly Gly Lys Tyr Leu
                420                 425                 430
Tyr Leu Cys Tyr Lys Lys Gln Ser Tyr Asp Asn Val Glu Ala Ile Lys
                435                 440                 445
Gly Leu Ala Val Val Gly Gly Asp Asn Ser His Thr Pro Ala Pro Tyr
                450                 455                 460
Gly Tyr Arg Arg Ile Asp Thr Asp Val Asn Glu Gly Ala Gly Gly Glu
465                 470                 475                 480
Tyr Ile Tyr Ile Cys Tyr Ser Lys Gly Ala
                485                 490

<210> SEQ ID NO 56
<211> LENGTH: 490
<212> TYPE: PRT
<213> ORGANISM: artificial sequence
<220> FEATURE:
<223> OTHER INFORMATION: Woodsholea maritima
```

<400> SEQUENCE: 56

```
Met Lys Ser Leu Asp His Val Ala His Gln Asn Leu Leu Asn Glu Pro
1               5                  10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Leu Phe Asn Pro
65                  70                  75                  80

Asp Tyr Leu Ala Pro Lys Ala Val Ser Gln Gln Asn Asp Glu Ala
                85                  90                  95

Arg Phe Thr Asn Val Ser Gly Lys Thr Ile Asn Thr Phe Gln Lys Asn
                100                 105                 110

Phe Ser Leu Lys Val Thr Val Ala Gly Ser Tyr Asn Leu Phe Ser Gly
            115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415
```

-continued

```
Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
            450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 57
<211> LENGTH: 490
<212> TYPE: PRT
<213> ORGANISM: artificial sequence
<220> FEATURE:
<223> OTHER INFORMATION: Woodsholea maritima

<400> SEQUENCE: 57

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
        50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
            115                 120                 125

Ser Val Ser Asn Glu Phe Ser Ser Glu Thr Arg Asn Ala Glu Asn
        130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
            210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Phe Arg Gln Ser Met Ser Ser Phe Ser
                245                 250                 255

Gln Asn Ser Asp Ile His Lys Leu Val Val Gly Gly Asp Gly Val Ala
            260                 265                 270

Gly Ala Lys Val Phe Ser Gly Asp Lys Ala Asp Phe Asp Ala Trp Ala
            275                 280                 285
```

```
Asp Thr Val Gly Thr Ser Pro Asp Phe Val Asp Phe Val Ser Ser Val
        290                 295                 300

Pro Met Leu Gly Ile Trp Glu Leu Cys Lys Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
                420                 425                 430

Tyr Leu Cys Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 58
<211> LENGTH: 490
<212> TYPE: PRT
<213> ORGANISM: artificial sequence
<220> FEATURE:
<223> OTHER INFORMATION: Woodsholea maritima

<400> SEQUENCE: 58

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160
```

Ala Tyr Thr Asp Ser Leu Arg Glu Tyr Leu Lys Ala Asp Val Arg Asp
            165                 170                 175

Tyr Ile Asp Ser Ile Gln Ser Asp Ala Gln Ile Glu Ile Leu Phe Asp
        180                 185                 190

Arg Tyr Gly Ser His Phe Leu Thr Gly Val Val Met Gly Gly Ala Ala
    195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
            245                 250                 255

Gln Asn Ser Asp Ile His Lys Ile Val Val Gly Gly Asp Gly Val Ala
        260                 265                 270

Gly Ala Lys Val Tyr Ser Gly Asp Lys Ala Asp Phe Asp Ala Trp Ala
    275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Phe Asn Asn Thr Trp Ala Pro Arg Lys Ser Lys
            325                 330                 335

Glu Ala Gln Leu Tyr Ala Asp Tyr Ile Asp Ala Val Glu Val Leu Gln
        340                 345                 350

Ser Asn Ser Ser Gly Val Arg Pro Pro Ser Gly Tyr Thr Lys Ile Asp
    355                 360                 365

Tyr Asp Leu Asn Lys Gly Ala Gly Asp Tyr Ile Tyr Leu Cys Tyr
370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
            405                 410                 415

Thr Lys Ile Asp Val Asp Leu Asn Glu Asp Ala Gly Gly Lys Tyr Leu
        420                 425                 430

Tyr Leu Cys Tyr Lys Lys Gln Ser Tyr Asp Asn Val Glu Ala Ile Lys
    435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
            485                 490

<210> SEQ ID NO 59
<211> LENGTH: 490
<212> TYPE: PRT
<213> ORGANISM: artificial sequence
<220> FEATURE:
<223> OTHER INFORMATION: Woodsholea maritima

<400> SEQUENCE: 59

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

-continued

```
Asn Leu Val Glu Arg Tyr Leu Pro Gly Val Glu Val Ile Gly Ala Gly
         35                  40                  45

Tyr Asn Pro Phe Gly Val Tyr Ala Ser Thr Asp Ser Val Thr Val Gln
 50                  55                  60

Leu Phe Asp Trp Gln Ser Ala Pro Ser Glu Pro Val Ile Phe Asn Pro
 65                  70                  75                  80

Asp Tyr Ile Ala Pro Lys Ala Val Ser Val Gln Gln Asn Asp Glu Ala
                 85                  90                  95

Arg Tyr Thr Asn Val Ser Gly Lys Thr Ile Asn Thr Phe Gln Lys Asn
                100                 105                 110

Phe Ser Leu Lys Val Thr Val Ala Gly Ser Tyr Asn Leu Phe Ser Gly
            115                 120                 125

Ser Val Ser Asn Glu Phe Ser Ser Ser Glu Thr Arg Asn Ala Glu Asn
        130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
                180                 185                 190

Arg Tyr Gly Ser His Phe Leu Thr Gly Val Val Met Gly Gly Ala Ala
            195                 200                 205

Leu Met Ala Ser Ser Thr Asn Lys Val Gln Val Asp His Thr Phe Glu
        210                 215                 220

Asn Glu Thr Leu Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
                260                 265                 270

Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
        290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
                340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Asp Tyr Ile Tyr Leu Cys Tyr
        370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
                420                 425                 430

Tyr Leu Cys Tyr Lys Lys Gln Ser Tyr Asp Asn Val Glu Ala Ile Lys
            435                 440                 445
```

```
Gly Leu Ala Val Val Gly Gly Asp Asn Ser His Thr Pro Ala Pro Tyr
        450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 60
<211> LENGTH: 490
<212> TYPE: PRT
<213> ORGANISM: artificial sequence
<220> FEATURE:
<223> OTHER INFORMATION: Woodsholea maritima

<400> SEQUENCE: 60

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320
```

```
Lys Met Glu Asp Tyr Tyr Asn Asn Thr Trp Ala Pro Arg Lys Ser Lys
            325                 330                 335

Glu Ala Gln Ile Tyr Ala Asp Tyr Ile Asp Ala Val Glu Val Ile Gln
        340                 345                 350

Ser Asn Ser Ser Gly Val Arg Pro Ser Gly Tyr Thr Lys Ile Asp
        355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Leu Lys
        435                 440                 445

Gly Leu Ala Val Val Gly Gly Asp Asn Ser His Thr Pro Ala Pro Phe
    450                 455                 460

Gly Tyr Arg Arg Leu Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 61
<211> LENGTH: 490
<212> TYPE: PRT
<213> ORGANISM: artificial sequence
<220> FEATURE:
<223> OTHER INFORMATION: Woodsholea maritima

<400> SEQUENCE: 61

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190
```

```
Arg Tyr Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Asp Gly Val Ala
            260                 265                 270

Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Gly Asp Tyr Ile Tyr Leu Cys Tyr
            370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Leu Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 62
<211> LENGTH: 490
<212> TYPE: PRT
<213> ORGANISM: artificial sequence
<220> FEATURE:
<223> OTHER INFORMATION: Woodsholea maritima

<400> SEQUENCE: 62

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
50                  55                  60
```

```
Leu Phe Asp Trp Gln Ser Ala Pro Ser Glu Pro Val Ile Phe Asn Pro
 65                  70                  75                  80

Asp Tyr Ile Ala Pro Lys Ala Val Ser Val Gln Gln Asn Asp Glu Ala
                 85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Asp Tyr Ile Tyr Leu Cys Tyr
370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Leu Tyr Ser Lys Gly Ala
```

485     490

<210> SEQ ID NO 63
<211> LENGTH: 490
<212> TYPE: PRT
<213> ORGANISM: artificial sequence
<220> FEATURE:
<223> OTHER INFORMATION: Woodsholea maritima

<400> SEQUENCE: 63

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
```

-continued

```
                355                 360                 365
Tyr Asp Leu Asn Lys Gly Ala Gly Gly Asp Tyr Ile Tyr Leu Cys Tyr
            370                 375                 380

His Lys Ala Arg Tyr Ser Ala Tyr Ser Glu Asn Lys Asp Cys Val Ser
385                 390                 395                 400

Asp Leu Leu Leu Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 64
<211> LENGTH: 490
<212> TYPE: PRT
<213> ORGANISM: artificial sequence
<220> FEATURE:
<223> OTHER INFORMATION: Woodsholea maritima

<400> SEQUENCE: 64

Met Lys Ser Leu Asp His Val Ala His Gln Asn Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
```

```
                225                 230                 235                 240
        Ser Ala Glu Thr Ala Ala Lys Tyr Arg Gln Ser Met Ser Ser Phe Ser
                        245                 250                 255

Gln Asn Ser Asp Ile His Lys Ile Val Val Gly Gly Asp Gly Val Ala
                        260                 265                 270

Gly Ala Lys Val Tyr Ser Gly Asp Lys Ala Asp Phe Asp Ala Trp Ala
                        275                 280                 285

Asp Thr Val Gly Thr Ser Pro Asp Phe Val Asp Phe Val Ser Ser Val
                        290                 295                 300

Pro Met Leu Gly Ile Trp Glu Leu Cys Lys Asp Asp Ala Gln Ala Lys
        305                 310                 315                 320

Lys Met Glu Asp Tyr Tyr Asn Asn Thr Trp Ala Pro Arg Lys Ser Lys
                        325                 330                 335

Glu Ala Gln Ile Tyr Ala Asp Tyr Ile Asp Ala Val Glu Val Ile Gln
                        340                 345                 350

Ser Asn Ser Ser Gly Val Arg Pro Pro Ser Gly Tyr Thr Lys Ile Asp
                        355                 360                 365

Tyr Asp Leu Asn Lys Gly Ala Gly Gly Asp Tyr Ile Tyr Leu Cys Tyr
                        370                 375                 380

His Lys Ala Arg Tyr Ser Ala Tyr Ser Glu Asn Lys Asp Cys Leu Ser
        385                 390                 395                 400

Asp Leu Ile Ile Ile Lys Gly Asn Gly Ala Arg Ala Pro Ser Gly Tyr
                        405                 410                 415

Thr Lys Ile Asp Val Asp Leu Asn Glu Asp Ala Gly Gly Lys Tyr Leu
                        420                 425                 430

Tyr Leu Cys Tyr Lys Lys Gln Ser Tyr Asp Asn Val Glu Ala Ile Lys
                        435                 440                 445

Gly Leu Ala Val Val Gly Gly Asp Asn Ser His Thr Pro Ala Pro Tyr
                        450                 455                 460

Gly Tyr Arg Arg Ile Asp Thr Asp Val Asn Glu Gly Ala Gly Gly Glu
        465                 470                 475                 480

Tyr Ile Tyr Ile Cys Tyr Ser Lys Gly Ala
                        485                 490

<210> SEQ ID NO 65
<211> LENGTH: 490
<212> TYPE: PRT
<213> ORGANISM: artificial sequence
<220> FEATURE:
<223> OTHER INFORMATION: Woodsholea maritima

<400> SEQUENCE: 65

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
                35                  40                  45

Tyr Asn Pro Phe Gly Val Tyr Ala Ser Thr Asp Ser Val Thr Val Gln
                50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
```

```
            100             105             110
Phe Ser Leu Lys Val Thr Val Ala Gly Ser Tyr Asn Leu Phe Ser Gly
            115             120             125

Ser Val Ser Asn Glu Phe Ser Ser Glu Thr Arg Asn Ala Glu Asn
130             135             140

Glu Phe Ser Arg Ile Gln Gln Ser Ile Arg Val Trp Ser Leu Arg Leu
145             150             155             160

Ala Tyr Thr Asp Ser Leu Arg Glu Tyr Leu Lys Ala Asp Val Arg Asp
                165             170             175

Tyr Ile Asp Ser Ile Gln Ser Asp Ala Gln Ile Glu Ile Leu Phe Asp
            180             185             190

Arg Tyr Gly Ser His Phe Leu Thr Gly Val Val Met Gly Gly Ala Ala
            195             200             205

Ile Met Ala Ser Ser Thr Asn Lys Val Gln Val Asp His Thr Tyr Glu
            210             215             220

Asn Glu Thr Ile Ala Lys Ala Ser Tyr Glu Ala Leu Thr Gly Gln Ile
225             230             235             240

Ser Ala Glu Thr Ala Ala Lys Tyr Arg Gln Ser Met Ser Ser Phe Ser
                245             250             255

Gln Asn Ser Asp Ile His Lys Ile Val Val Gly Asp Gly Val Ala
            260             265             270

Gly Ala Lys Val Tyr Ser Gly Asp Lys Ala Asp Phe Asp Ala Trp Ala
            275             280             285

Asp Thr Val Gly Thr Ser Pro Asp Phe Val Asp Phe Val Ser Ser Val
            290             295             300

Pro Met Leu Gly Ile Trp Glu Leu Cys Lys Asp Asp Ala Gln Ala Lys
305             310             315             320

Lys Met Glu Asp Tyr Tyr Asn Asn Thr Trp Ala Pro Arg Lys Ser Lys
                325             330             335

Glu Ala Gln Ile Tyr Ala Asp Tyr Ile Asp Ala Val Glu Val Ile Gln
            340             345             350

Ser Asn Ser Ser Gly Val Arg Pro Pro Ser Gly Tyr Thr Lys Ile Asp
            355             360             365

Tyr Asp Leu Asn Lys Gly Ala Gly Gly Asp Tyr Ile Tyr Leu Cys Tyr
            370             375             380

His Lys Ala Arg Tyr Ser Ala Tyr Ser Glu Asn Lys Asp Cys Phe Ser
385             390             395             400

Asp Leu Ile Ile Ile Lys Gly Asn Gly Ala Arg Ala Pro Ser Gly Tyr
            405             410             415

Thr Lys Ile Asp Val Asp Leu Asn Glu Asp Ala Gly Gly Lys Tyr Leu
            420             425             430

Tyr Leu Cys Tyr Lys Lys Gln Ser Tyr Asp Asn Val Glu Ala Ile Lys
            435             440             445

Gly Leu Ala Val Val Gly Gly Asp Asn Ser His Thr Pro Ala Pro Tyr
            450             455             460

Gly Tyr Arg Arg Ile Asp Thr Asp Val Asn Glu Gly Ala Gly Gly Glu
465             470             475             480

Tyr Ile Tyr Ile Cys Tyr Ser Lys Gly Ala
            485             490

<210> SEQ ID NO 66
<211> LENGTH: 490
<212> TYPE: PRT
<213> ORGANISM: artificial sequence
```

```
<220> FEATURE:
<223> OTHER INFORMATION: Woodsholea maritima

<400> SEQUENCE: 66

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Phe Val Ser
385                 390                 395                 400
```

```
Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
            485                 490

<210> SEQ ID NO 67
<211> LENGTH: 490
<212> TYPE: PRT
<213> ORGANISM: artificial sequence
<220> FEATURE:
<223> OTHER INFORMATION: Woodsholea maritima

<400> SEQUENCE: 67

Met Lys Ser Leu Asp His Val Ala His Gln Asn Leu Leu Asn Glu Pro
1               5                   10                  15

Thr His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270
```

```
Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
            290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
            355                 360                 365

Tyr Asp Leu Asn Lys Gly Ala Gly Asp Tyr Ile Tyr Leu Cys Tyr
            370                 375                 380

His Lys Ala Arg Tyr Ser Ala Tyr Ser Glu Asn Lys Asp Tyr Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
            450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 68
<211> LENGTH: 490
<212> TYPE: PRT
<213> ORGANISM: artificial sequence
<220> FEATURE:
<223> OTHER INFORMATION: Woodsholea maritima

<400> SEQUENCE: 68

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
            115                 120                 125

Ser Val Ser Asn Glu Phe Ser Ser Glu Thr Arg Asn Ala Glu Asn
            130                 135                 140
```

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
            165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
            245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
            325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Ile Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
            485                 490

<210> SEQ ID NO 69
<211> LENGTH: 490
<212> TYPE: PRT
<213> ORGANISM: artificial sequence
<220> FEATURE:
<223> OTHER INFORMATION: Woodsholea maritima

<400> SEQUENCE: 69

Met Lys Ser Leu Asp His Val Ala His Gln Asn Leu Leu Asn Glu Pro
1               5                   10                  15

```
Thr His His Lys Ser Asn Thr Lys Ala Ala Leu Met Arg His Gln Glu
         20                  25                  30

Asn Leu Val Glu Arg Tyr Leu Pro Gly Val Glu Val Ile Gly Ala Gly
             35                  40                  45

Tyr Asn Pro Phe Gly Val Tyr Ala Ser Thr Asp Ser Val Thr Val Gln
 50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Gln Gln Asn Asp Glu Ala
                 85                  90                  95

Arg Tyr Thr Asn Val Ser Gly Lys Thr Ile Asn Thr Phe Gln Lys Asn
             100                 105                 110

Phe Ser Leu Lys Val Thr Val Ala Gly Ser Tyr Asn Leu Phe Ser Gly
         115                 120                 125

Ser Val Ser Asn Glu Phe Ser Ser Glu Thr Arg Asn Ala Glu Asn
     130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                 165                 170                 175

Tyr Ile Asp Ser Ile Gln Ser Asp Ala Gln Ile Glu Ile Leu Phe Asp
             180                 185                 190

Arg Tyr Gly Ser His Phe Leu Thr Gly Val Val Met Gly Gly Ala Ala
         195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                 245                 250                 255

Gln Asn Ser Asp Ile His Lys Ile Val Val Gly Gly Asp Gly Val Ala
             260                 265                 270

Gly Ala Lys Val Tyr Ser Gly Asp Lys Ala Asp Phe Asp Ala Trp Ala
         275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                 325                 330                 335

Glu Ala Gln Ile Tyr Ala Asp Tyr Ile Asp Ala Val Glu Val Ile Gln
             340                 345                 350

Ser Asn Ser Ser Gly Val Arg Pro Pro Ser Gly Tyr Thr Lys Ile Asp
         355                 360                 365

Tyr Asp Leu Asn Lys Gly Ala Gly Gly Asp Tyr Ile Tyr Leu Cys Tyr
370                 375                 380

His Lys Ala Arg Tyr Ser Ala Tyr Ser Glu Asn Lys Asp Met Val Ser
385                 390                 395                 400

Asp Leu Ile Ile Ile Lys Gly Asn Gly Ala Arg Ala Pro Ser Gly Tyr
                 405                 410                 415

Thr Lys Ile Asp Val Asp Leu Asn Glu Asp Ala Gly Gly Lys Tyr Leu
             420                 425                 430
```

```
Tyr Leu Cys Tyr Lys Lys Gln Ser Tyr Asp Asn Val Glu Ala Ile Lys
            435                 440                 445

Gly Leu Ala Val Val Gly Gly Asp Asn Ser His Thr Pro Ala Pro Tyr
        450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 70
<211> LENGTH: 13
<212> TYPE: PRT
<213> ORGANISM: Woodsholea maritima

<400> SEQUENCE: 70

Tyr Gly Ser His Phe Leu Thr Gly Val Val Met Gly Gly
1               5                   10

<210> SEQ ID NO 71
<211> LENGTH: 178
<212> TYPE: PRT
<213> ORGANISM: artificial sequence
<220> FEATURE:
<223> OTHER INFORMATION: Woodsholea maritima

<400> SEQUENCE: 71

Cys Lys Asp Asp Ala Gln Ala Lys Lys Met Glu Asp Tyr Tyr Asn Asn
1               5                   10                  15

Thr Trp Ala Pro Arg Lys Ser Lys Glu Ala Gln Ile Tyr Ala Asp Tyr
            20                  25                  30

Ile Asp Ala Val Glu Val Ile Gln Ser Asn Ser Ser Gly Val Arg Pro
        35                  40                  45

Pro Ser Gly Tyr Thr Lys Ile Asp Tyr Asp Leu Asn Lys Gly Ala Gly
    50                  55                  60

Gly Asp Tyr Ile Tyr Leu Cys Tyr His Lys Ala Arg Tyr Ser Ala Tyr
65                  70                  75                  80

Ser Glu Asn Lys Asp Cys Val Ser Asp Leu Ile Ile Ile Lys Gly Asn
                85                  90                  95

Gly Ala Arg Ala Pro Ser Gly Tyr Thr Lys Ile Asp Val Asp Leu Asn
            100                 105                 110

Glu Asp Ala Gly Gly Lys Tyr Leu Tyr Leu Cys Tyr Lys Lys Gln Ser
        115                 120                 125

Tyr Asp Asn Val Glu Ala Ile Lys Gly Leu Ala Val Val Gly Gly Asp
    130                 135                 140

Asn Ser His Thr Pro Ala Pro Tyr Gly Tyr Arg Arg Ile Asp Thr Asp
145                 150                 155                 160

Val Asn Glu Gly Ala Gly Gly Glu Tyr Ile Tyr Ile Cys Tyr Ser Lys
                165                 170                 175

Gly Ala

<210> SEQ ID NO 72
<211> LENGTH: 490
<212> TYPE: PRT
<213> ORGANISM: artificial sequence
<220> FEATURE:
<223> OTHER INFORMATION: Woodsholea maritima
<220> FEATURE:
<221> NAME/KEY: misc_feature
<222> LOCATION: (77)..(77)
<223> OTHER INFORMATION: Xaa can be any naturally occurring amino acid
```

```
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (340)..(340)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (406)..(406)
<223> OTHER INFORMATION: Xaa can be any naturally occurring amino acid
<220> FEATURE:
<221> NAME/KEY: misc_feature
<222> LOCATION: (435)..(435)
<223> OTHER INFORMATION: Xaa can be any naturally occurring amino acid
<220> FEATURE:
<221> NAME/KEY: misc_feature
<222> LOCATION: (447)..(447)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (469)..(469)
```

<223> OTHER INFORMATION: Xaa can be any naturally occurring amino acid
<220> FEATURE:
<221> NAME/KEY: misc_feature
<222> LOCATION: (485)..(485)
<223> OTHER INFORMATION: Xaa can be any naturally occurring amino acid

<400> SEQUENCE: 72

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
50                  55                  60

Leu Phe Asp Trp Gln Ser Ala Pro Ser Glu Pro Val Xaa Phe Asn Pro
65                  70                  75                  80

Asp Tyr Xaa Ala Pro Lys Ala Val Ser Val Gln Gln Asn Asp Glu Ala
                85                  90                  95

Arg Xaa Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Xaa Gly Ser His Phe Leu Thr Gly Val Val Met Gly Gly Ala Ala
        195                 200                 205

Ile Met Ala Ser Ser Thr Asn Lys Val Gln Val Asp His Thr Xaa Glu
210                 215                 220

Asn Glu Thr Xaa Ala Lys Ala Ser Tyr Glu Ala Leu Thr Gly Gln Ile
225                 230                 235                 240

Ser Ala Glu Thr Ala Ala Lys Xaa Arg Gln Ser Met Ser Ser Phe Ser
                245                 250                 255

Gln Asn Ser Asp Ile His Lys Xaa Val Val Gly Gly Asp Gly Val Ala
            260                 265                 270

Gly Ala Lys Val Xaa Ser Gly Asp Lys Ala Asp Phe Asp Ala Trp Ala
        275                 280                 285

Asp Thr Val Gly Thr Ser Pro Asp Phe Val Asp Phe Ser Ser Val
290                 295                 300

Pro Met Leu Gly Ile Trp Glu Leu Xaa Lys Asp Asp Ala Gln Ala Lys
305                 310                 315                 320

Lys Met Glu Asp Tyr Xaa Asn Asn Thr Trp Ala Pro Arg Lys Ser Lys
                325                 330                 335

Glu Ala Gln Xaa Tyr Ala Asp Tyr Ile Asp Ala Val Glu Val Xaa Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Xaa Tyr
370                 375                 380
```

His Lys Ala Arg Tyr Ser Ala Tyr Ser Glu Asn Xaa Asp Xaa Val Ser
385                 390                 395                 400

Asp Leu Ile Ile Ile Xaa Gly Asn Gly Ala Arg Ala Pro Ser Gly Tyr
            405                 410                 415

Thr Lys Ile Asp Val Asp Leu Asn Glu Asp Ala Gly Gly Lys Tyr Leu
        420                 425                 430

Tyr Leu Xaa Tyr Lys Lys Gln Ser Tyr Asp Asn Val Glu Ala Xaa Lys
            435                 440                 445

Gly Leu Ala Val Val Gly Gly Asp Asn Ser His Thr Pro Ala Pro Xaa
        450                 455                 460

Gly Tyr Arg Arg Xaa Asp Thr Asp Val Asn Glu Gly Ala Gly Gly Glu
465                 470                 475                 480

Tyr Ile Tyr Ile Xaa Tyr Ser Lys Gly Ala
            485                 490

<210> SEQ ID NO 73
<211> LENGTH: 1479
<212> TYPE: DNA
<213> ORGANISM: artificial sequence
<220> FEATURE:
<223> OTHER INFORMATION: Woodsholea maritima

<400> SEQUENCE: 73

| | |
|---|---:|
| atgaaaagct tggatcacgt tgctcatcag aacttactga tgaaccgac tcaccataaa | 60 |
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aacttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |
| ggatcctata acttatttag cggtagcgtc agcaatgaat tcagcagcag cgaaactcgc | 420 |
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |
| cacacatacg agaatgaaac cattgccaag gccagctacg aagccttaac tgggcagatc | 720 |
| tctgctgaga ctgcggctaa atatcgccaa agcatgtcgt cgttctccca gaactccgat | 780 |
| attcacaaaa ttgtggtcgg cggagacgga gtcgcgggcg cgaaagtgta tagcggtgac | 840 |
| aaggcggatt cgatgcttg gctgacacc gtgggacgt ctccagattt tgtggacttt | 900 |
| gttagcagcg ttcctatgtt gggaatttgg gaactgtgca agatgacgc gcaggcgaaa | 960 |
| aagatggaag attactataa taatacgtgg gccccgcgga aaagcaaaga ggctcaaatt | 1020 |
| tatgctgatt atatcgacgc agtcgaagtg atccagagta attcttcggg ggttcgccct | 1080 |
| cccagtggat atacgaaaat tgattacgac ctcaataaag gcgccggtgg ggattatatc | 1140 |
| tacctgtgtt atcataaagc ccgttatagc gcttactcag aaaacaaaga ttgcctgtta | 1200 |
| gtttctgatt taattattat taagggaaac ggagcacgcg ccccgagcgg ttatacgaaa | 1260 |
| attgatgtgg atttgaatga ggatgcaggt ggaaaatacc tgtatttatg ctacaagaag | 1320 |
| caaagttacg acaatgtgga agcaatcaag gggctggcgg tagttggtgg tgacaattcg | 1380 |
| cataccctg ctccgtacgg ttaccgtcgg attgacaccg atgttaacga gggggccgga | 1440 |

```
ggtgagtaca tttatatctg ttactccaaa ggggcttaa                    1479
```

<210> SEQ ID NO 74
<211> LENGTH: 1479
<212> TYPE: DNA
<213> ORGANISM: artificial sequence
<220> FEATURE:
<223> OTHER INFORMATION: Woodsholea maritima

<400> SEQUENCE: 74

```
atgaaaagct tggatcacgt tgctcatcag aacttactga atgaaccgac tcaccataaa      60
agcaatacca aggcggcgct gatgcgtcat caggaaaacc tggttgaacg ctatctgccg     120
ggtgtggagg tgattggggc aggttacaac cctttcggcg tatacgcgtc cactgactca     180
gttactgtgc aactttttga ttggcaaagc gcgccatcag aaccggtcat tttttaacccc     240
gattacattg ctccgaaagc tgtgtcagta caacaaaatg atgaagcccg gtatacgaac     300
gttagcggca aaacaatcaa cacgtttcaa aaaaacttct ccctgaaagt tactgtcgcg     360
ggatcctata acttatttag cggtagcgtc agcaatgaat tcagcagcag cgaaactcgc     420
aatgcagaaa acgaatttag ccgcatccaa cagagcatcc gcgtctggtc tctgcgcctc     480
gcgtacacgg attccctgcg tgaatattta aaagcggacg ttcgcgatta tatcgatagc     540
attcaatcag atgcgcagat tgaaattctg tttgatcgtt acgggtcaca tttccttacc     600
ggcgtggtga tgggtggcgc agcaatcatg gcgtcttcga ccaataaagt acaggtggac     660
cacacatacg agaatgaaac cattgccaag gccagctacg aagccttaac tgggcagatc     720
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt cgatgcttg gctgacaccc gtggggacgt ctccagattt tgtggacttt     900
gttagcagcg ttcctatgtt gggaatttgg gaactgtgca agatgacgc gcaggcgaaa     960
aagatggaag attactataa taatacgtgg gccccgcgga aaagcaaaga ggctcaaatt    1020
tatgctgatt atatcgacgc agtcgaagtg atccagagta attcttcggg ggttcgccct    1080
cccagtggat atacgaaaat tgattacgac ctcaataaag gcgccggtgg ggattatatc    1140
tacctgtgtt atcataaagc ccgttatagc gcttactcag aaaacaaaga ttgcctgtta    1200
gtttctgatt taattattat taagggaaac ggagcacgcg ccccgagcgg ttatacgaaa    1260
attgatgtgg atttgaatga ggatgcaggt ggaaaatacc tgtatttatg ctacaagaag    1320
caaagttacg acaatgtgga agcaatcaag gggctggcgg tagttggtgg tgacaattcg    1380
catacccctg ctccgtacgg ttaccgtcgg attgacaccg atgttaacga gggggccgga    1440
ggtgagtaca tttatatctg ttactccaaa ggggcttaa                    1479
```

<210> SEQ ID NO 75
<211> LENGTH: 1479
<212> TYPE: DNA
<213> ORGANISM: artificial sequence
<220> FEATURE:
<223> OTHER INFORMATION: Woodsholea maritima

<400> SEQUENCE: 75

```
atgaaaagct tggatcacgt tgctcatcag aacttactga atgaaccgac tcaccataaa      60
agcaatacca aggcggcgct gatgcgtcat caggaaaacc tggttgaacg ctatctgccg     120
ggtgtggagg tgattggggc aggttacaac cctttcggcg tatacgcgtc cactgactca     180
```

```
gttactgtgc aacttttttga ttggcaaagc gcgccatcag aaccggtcat ttttaacccc    240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360 ggatccatata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca agatgacgc gcaggcgaaa    960 aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaaacaaaga tctgtgcctg   1200
gtttctgatt taattattat taagggaaac ggagcacgcg ccccgagcgg ttatacgaaa   1260
attgatgtgg atttgaatga ggatgcaggt ggaaaatacc tgtatttatg ctacaagaag   1320
caaagttacg acaatgtgga agcaatcaag gggctggcgg tagttggtgg tgacaattcg   1380
catacccctg ctccgtacgg ttaccgtcgg attgacaccg atgttaacga gggggccgga   1440
ggtgagtaca tttatatctg ttactccaaa ggggcttaa                          1479
```

<210> SEQ ID NO 76
<211> LENGTH: 1473
<212> TYPE: DNA
<213> ORGANISM: artificial sequence
<220> FEATURE:
<223> OTHER INFORMATION: Woodsholea maritima

<400> SEQUENCE: 76

```
atgaaaagct tggatcacgt tgctcatcag aacttactga atgaaccgac tcaccataaa     60
agcaatacca aggcggcgct gatgcgtcat caggaaaaacc tggttgaacg ctatctgccg   120
ggtgtggagg tgattggggc aggttacaac cctttcggcg tatacgcgtc cactgactca   180
gttactgtgc aacttttttga ttggcaaagc gcgccatcag aaccggtcat ttttaacccc   240
gattacattg ctccgaaagc tgtgtcagta caacaaaatg atgaagcccg gtatacgaac   300
gttagcggca aaacaatcaa cacgtttcaa aaaaacttct ccctgaaagt tactgtcgcg   360 ggatccatata acttatttag cggtagcgtc agcaatgaat tcagcagcag cgaaactcgc   420
aatgcagaaa acgaatttag ccgcatccaa cagagcatcc gcgtctggtc tctgcgcctc   480
gcgtacacgg attccctgcg tgaatattta aaagcggacg ttcgcgatta tatcgatagc   540
attcaatcag atgcgcagat tgaaattctg tttgatcgtt acgggtcaca tttccttacc   600
ggcgtggtga tgggtggcgc agcaatcatg gcgtcttcga ccaataaagt acaggtggac   660
cacacatacg agaatgaaac cattgccaag gccagctacg aagccttaac tgggcagatc   720
tctgctgaga ctgcggctaa atatcgccaa agcatgtcgt cgttctccca gaactccgat   780
```

```
attcacaaaa ttgtggtcgg cggagacgga gtcgcgggcg cgaaagtgta tagcggtgac      840
aaggcggatt tcgatgcttg ggctgacacc gtggggacgt ctccagattt tgtggacttt      900
gttagcagcg ttcctatgtt gggaatttgg gaactgtgca agatgacgc gcaggcgaaa       960 aagatggaag attactataa taatacgtgg gccccgcgga aaagcaaaga ggctcaaatt     1020
tatgctgatt atatcgacgc agtcgaagtg atccagagta attcttcggg ggttcgccct     1080
cccagtggat atacgaaaat tgattacgac ctcaataaag gcgccggtgg ggattatatc     1140
tacctgtgtt atcataaagc ccgttatagc gcttactcag aaaacaaaga ttgcgtttct     1200
gatttaatta ttattaaggg aaacggagca cgcgccccga gcggttatac gaaaattgat     1260
gtggatttga atgaggatgc aggtggaaaa tacctgtatt tatgctttaa gaagcaaagt     1320
tacgacaatg tggaagcaat caaggggctg gcggtagttg gtggtgacaa ttcgcatacc     1380
cctgctccgt acggttaccg tcggattgac accgatgtta acgaggggc cggaggtgag      1440 tacatttata tctgttactc caaaggggct taa                                  1473
```

<210> SEQ ID NO 77
<211> LENGTH: 1476
<212> TYPE: DNA
<213> ORGANISM: artificial sequence
<220> FEATURE:
<223> OTHER INFORMATION: Woodsholea maritima

<400> SEQUENCE: 77

```
atgaaaagct tggatcacgt tgctcatcag aacttactga atgaaccgac tcaccataaa       60
agcaatacca aggcggcgct gatgcgtcat caggaaaacc tggttgaacg ctatctgccg      120
ggtgtggagg tgattggggc aggttacaac cctttcggcg tatacgcgtc cactgactca      180
gttactgtgc aacttttga ttggcaaagc gcgccatcag aaccggtcat ttttaacccc       240
gattacattg ctccgaaagc tgtgtcagta caacaaaatg atgaagcccg gtatacgaac      300
gttagcggca aaacaatcaa cacgtttcaa aaaaacttct ccctgaaagt tactgtcgcg      360
ggatcctata acttatttag cggtagcgtc agcaatgaat tcagcagcag cgaaactcgc      420
aatgcagaaa acgaatttag ccgcatccaa cagagcatcc gcgtctggtc tctgcgcctc      480
gcgtacacgg attccctgcg tgaatattta aaagcggacg ttcgcgatta tatcgatagc      540
attcaatcag atgcgcagat tgaaattctg tttgatcgtt acgggtcaca tttccttacc      600
ggcgtggtga tgggtggcgc agcaatcatg gcgtcttcga ccaataaagt acaggtggac      660
cacacatacg agaatgaaac cattgccaag gccagctacg aagccttaac tgggcagatc      720
tctgctgaga ctgcggctaa atatcgccaa agcatgtcgt cgttctccca gaactccgat      780
attcacaaaa ttgtggtcgg cggagacgga gtcgcgggcg cgaaagtgta tagcggtgac      840
aaggcggatt tcgatgcttg ggctgacacc gtggggacgt ctccagattt tgtggacttt      900
gttagcagcg ttcctatgtt gggaatttgg gaactgtgca agatgacgc gcaggcgaaa       960 aagatggaag attactataa taatacgtgg gccccgcgga aaagcaaaga ggctcaaatt     1020
tatgctgatt atatcgacgc agtcgaagtg atccagagta attcttcggg ggttcgccct     1080
cccagtggat atacgaaaat tgattacgac ctcaataaag gcgccggtgg ggattatatc     1140
tacctgtgtt atcataaagc ccgttatagc gcttactcag aaaacaaaga tctgtgcgtt     1200
tctgatttaa ttattattaa gggaaacgga gcacgcgccc cgagcggtta tacgaaaatt     1260
gatgtggatt tgaatgagga tgcaggtgga aaatacctgt atttatgcta caagaagcaa     1320
```

| | |
|---|---|
| agttacgaca atgtggaagc aatcaagggg ctggcggtag ttggtggtga caattcgcat | 1380 |
| acccctgctc cgtacggtta ccgtcggatt gacaccgatg ttaacgaggg ggccggaggt | 1440 |
| gagtacattt atatctgtta ctccaaaggg gcttaa | 1476 |

<210> SEQ ID NO 78
<211> LENGTH: 1476
<212> TYPE: DNA
<213> ORGANISM: artificial sequence
<220> FEATURE:
<223> OTHER INFORMATION: Woodsholea maritima

<400> SEQUENCE: 78

| | |
|---|---|
| atgaaaagct tggatcacgt tgctcatcag aacttactga atgaaccgac tcaccataaa | 60 |
| agcaatacca aggcggcgct gatgcgtcat caggaaaacc tggttgaacg ctatctgccg | 120 |
| ggtgtggagg tgattggggc aggttacaac cctttcggcg tatacgcgtc cactgactca | 180 |
| gttactgtgc aacttttga ttggcaaagc gcgccatcag aaccggtcat ttttaacccc | 240 |
| gattacattg ctccgaaagc tgtgtcagta caacaaaatg atgaagcccg gtatacgaac | 300 |
| gttagcggca aaacaatcaa cacgtttcaa aaaaacttct ccctgaaagt tactgtcgcg | 360 |
| ggatcctata acttatttag cggtagcgtc agcaatgaat tcagcagcag cgaaactcgc | 420 |
| aatgcagaaa acgaatttag ccgcatccaa cagagcatcc gcgtctggtc tctgcgcctc | 480 |
| gcgtacacgg attccctgcg tgaatattta aaagcggacg ttcgcgatta tatcgatagc | 540 |
| attcaatcag atgcgcagat tgaaattctg tttgatcgtt acgggtcaca tttccttacc | 600 |
| ggcgtggtga tgggtggcgc agcaatcatg gcgtcttcga ccaataaagt acaggtggac | 660 |
| cacacatacg agaatgaaac cattgccaag gccagctacg aagccttaac tgggcagatc | 720 |
| tctgctgaga ctgcggctaa atatcgccaa agcatgtcgt cgttctccca gaactccgat | 780 |
| attcacaaaa ttgtggtcgg cggagacgga gtcgcgggcg cgaaagtgta tagcggtgac | 840 |
| aaggcggatt tcgatgcttg ggctgacacc gtggggacgt ctccagattt tgtggacttt | 900 |
| gttagcagcg ttcctatgtt gggaatttgg gaactgtgca agatgacgc gcaggcgaaa | 960 |
| aagatggaag attactataa taatacgtgg ccccgcgga aaagcaaaga ggctcaaatt | 1020 |
| tatgctgatt atatcgacgc agtcgaagtg atccagagta attcttcggg ggttcgccct | 1080 |
| cccagtggat atacgaaaat tgattacgac ctcaataaag cgccggtgg ggattatatc | 1140 |
| tacctgtgtt atcataaagc ccgttatagc gcttactcag aaaacaaaga ttgcctggtt | 1200 |
| tctgatttaa ttattattaa gggaaacgga gcacgcgccc cgagcggtta tacgaaaatt | 1260 |
| gatgtggatt tgaatgagga tgcaggtgga aaatacctgt atttatgcta caagaagcaa | 1320 |
| agttacgaca atgtggaagc aatcaagggg ctggcggtag ttggtggtga caattcgcat | 1380 |
| acccctgctc cgtacggtta ccgtcggatt gacaccgatg ttaacgaggg ggccggaggt | 1440 |
| gagtacattt atatctgtta ctccaaaggg gcttaa | 1476 |

<210> SEQ ID NO 79
<211> LENGTH: 1476
<212> TYPE: DNA
<213> ORGANISM: artificial sequence
<220> FEATURE:
<223> OTHER INFORMATION: Woodsholea maritima

<400> SEQUENCE: 79

| | |
|---|---|
| atgaaaagct tggatcacgt tgctcatcag aacttactga atgaaccgac tcaccataaa | 60 |
| agcaatacca aggcggcgct gatgcgtcat caggaaaacc tggttgaacg ctatctgccg | 120 |

```
ggtgtggagg tgattggggc aggttacaac cctttcggcg tatacgcgtc cactgactca    180
gttactgtgc aacttttga ttggcaaagc gcgccatcag aaccggtcat ttttaacccc     240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt cgatgcttg gctgacacc gtggggacgt ctccagattt tgtggacttt      900
gttagcagcg ttcctatgtt gggaatttgg gaactgtgca agatgacgc gcaggcgaaa     960 aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgctgt gttatcataa agcccgttat agcgcttact cagaaaacaa agattgcgtt   1200
tctgatttaa ttattattaa gggaaacgga gcacgcgccc cgagcggtta tacgaaaatt   1260
gatgtggatt tgaatgagga tgcaggtgga aaatacctgt attatgcta caagaagcaa    1320 agttacgaca atgtggaagc aatcaagggg ctggcggtag ttggtggtga caattcgcat   1380
acccctgctc cgtacggtta ccgtcggatt gacaccgatg ttaacgaggg ggccggaggt   1440
gagtacattt atatctgtta ctccaaaggg gcttaa                             1476
```

<210> SEQ ID NO 80
<211> LENGTH: 1476
<212> TYPE: DNA
<213> ORGANISM: artificial sequence
<220> FEATURE:
<223> OTHER INFORMATION: Woodsholea maritima

<400> SEQUENCE: 80

```
atgaaaagct tggatcacgt tgctcatcag aacttactga atgaaccgac tcaccataaa     60
agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aacttttga ttggcaaagc gcgccatcag aaccggtcat ttttaacccc     240
gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
```

```
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca aagatgacgc gcaggcgaaa    960
aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtc tgtatcataa agcccgttat agcgcttact cagaaaacaa agattgcgtt   1200
tctgatttaa ttattattaa gggaaacgga gcacgcgccc cgagcggtta tacgaaaatt   1260
gatgtggatt tgaatgagga tgcaggtgga aaatacctgt atttatgcta caagaagcaa   1320
agttacgaca atgtggaagc aatcaagggg ctggcggtag ttggtggtga caattcgcat   1380 accccctgctc cgtacggtta ccgtcggatt gacaccgatg ttaacgaggg ggccggaggt   1440
gagtacattt atatctgtta ctccaaaggg gcttaa                             1476
```

<210> SEQ ID NO 81
<211> LENGTH: 1476
<212> TYPE: DNA
<213> ORGANISM: artificial sequence
<220> FEATURE:
<223> OTHER INFORMATION: Woodsholea maritima

<400> SEQUENCE: 81

```
atgaaaagct tggatcacgt tgctcatcag aacttactga atgaaccgac tcaccataaa     60
agcaatacca aggcggcgct gatgcgtcat caggaaaacc tggttgaacg ctatctgccg    120
ggtgtggagg tgattggggc aggttacaac cctttcggcg tatacgcgtc cactgactca    180
gttactgtgc aacttttttga ttggcaaagc gcgccatcag aaccggtcat ttttaaccccc   240 gattacattg ctccgaaagc tgtgtcagta caacaaaatg atgaagcccg gtatacgaac    300
gttagcggca aaacaatcaa cacgtttcaa aaaaacttct ccctgaaagt tactgtcgcg    360
ggatcctata acttatttag cggtagcgtc agcaatgaat tcagcagcag cgaaactcgc    420
aatgcagaaa acgaatttag ccgcatccaa cagagcatcc gcgtctggtc tctgcgcctc    480
gcgtacacgg attccctgcg tgaatattta aaagcggacg ttcgcgatta tatcgatagc    540
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgt ctccagattt tgtggacttt    900
gttagcagcg ttcctatgtt gggaatttgg gaactgtgca aagatgacgc gcaggcgaaa    960
aagatggaag attactataa taatacgtgg gccccgcgga aaagcaaaga ggctcaaatt   1020
tatgctgatt atatcgacgc agtcgaagtg atccagagta attcttcggg ggttcgccct   1080
cccagtggat atacgaaaat tgattacgac ctcaataaag gcgccggtgg ggattatatc   1140
tacctgtgtt atcataaagc ccgttatagc gcttactcag aaacaaaga ttgcgttct    1200 gatttaatta ttattaaggg aaacggagca cgcgccccga gcggttatac gaaaattgat   1260
```

```
gtggatttga atgaggatgc aggtggaaaa tacctgtatt tactgtgcta caagaagcaa    1320
agttacgaca atgtggaagc aatcaagggg ctggcggtag ttggtggtga caattcgcat    1380
acccctgctc cgtacggtta ccgtcggatt gacaccgatg ttaacgaggg ggccggaggt    1440
gagtacattt atatctgtta ctccaaaggg gcttaa                              1476
```

<210> SEQ ID NO 82
<211> LENGTH: 1476
<212> TYPE: DNA
<213> ORGANISM: artificial sequence
<220> FEATURE:
<223> OTHER INFORMATION: Woodsholea maritima

<400> SEQUENCE: 82

```
atgaaaagct tggatcacgt tgctcatcag aacttactga atgaaccgac tcaccataaa      60
agcaatacca aggcggcgct gatgcgtcat caggaaaacc tggttgaacg ctatctgccg     120
ggtgtggagg tgattgggc aggttacaac cctttcggcg tatacgcgtc cactgactca     180
gttactgtgc aactttttga ttggcaaagc gcgccatcag aaccggtcat ttttaacccc     240
gattacattg ctccgaaagc tgtgtcagta caacaaaatg atgaagcccg gtatacgaac     300
gttagcggca aaacaatcaa cacgtttcaa aaaaacttct ccctgaaagt tactgtcgcg     360
ggatcctata acttatttag cggtagcgtc agcaatgaat tcagcagcag cgaaactcgc     420
aatgcagaaa acgaatttag ccgcatccaa cagagcatcc gcgtctggtc tctgcgcctc     480
gcgtacacgg attccctgcg tgaatattta aaagcggacg ttcgcgatta tatcgatagc     540
attcaatcag atgcgcagat tgaaattctg tttgatcgtt acgggtcaca tttccttacc     600
ggcgtggtga tgggtggcgc agcaatcatg gcgtcttcga ccaataaagt acaggtggac     660
cacacatacg agaatgaaac cattgccaag gccagctacg aagccttaac tgggcagatc     720
tctgctgaga ctgcggctaa atatcgccaa agcatgtcgt cgttctccca gaactccgat     780
attcacaaaa ttgtggtcgg cggagacgga gtcgcgggcg cgaaagtgta tagcggtgac     840
aaggcggatt tcgatgcttg ggctgacacc gtggggacgt ctccagattt tgtggacttt     900
gttagcagcg ttcctatgtt gggaatttgg gaactgtgca agatgacgc gcaggcgaaa     960 aagatggaag attactataa taatacgtgg gccccgcgga aaagcaaaga ggctcaaatt    1020
tatgctgatt atatcgacgc agtcgaagtg atccagagta attcttcggg ggttcgcgcct   1080 cccagtggat atacgaaaat tgattacgac ctcaataaag cgccggtgg ggattatatc    1140 tacctgtgtt atcataaagc ccgttatagc gcttactcag aaaacaaaga ttgcgtttct   1200
gatttaatta ttattaaggg aaacggagca cgcgccccga gcggttatac gaaaattgat   1260
gtggatttga atgaggatgc aggtggaaaa tacctgtatt tatgcctgta caagaagcaa    1320
agttacgaca atgtggaagc aatcaagggg ctggcggtag ttggtggtga caattcgcat    1380
acccctgctc cgtacggtta ccgtcggatt gacaccgatg ttaacgaggg ggccggaggt    1440
gagtacattt atatctgtta ctccaaaggg gcttaa                              1476
```

<210> SEQ ID NO 83
<211> LENGTH: 1521
<212> TYPE: DNA
<213> ORGANISM: artificial sequence
<220> FEATURE:
<223> OTHER INFORMATION: Woodsholea maritima, Photorhabdus luminescens

<400> SEQUENCE: 83

-continued

```
atgtcaaacg ataaaacggg aaaaagtctg gaacaggaaa atagcgagcg cgacgttgaa      60
attcgcgatc gcaactactt tcgcaaattg agcttgtttg acgatactgt tatcgccggt     120
gcggagatga tcggtactag ctacgatgtg tttggcaagt actgcaatgt aggaagctgc     180
atgaacagcc tcttcgatga acgtaaaatc aacgcgagtg aagacaactt taaaaaagtt     240
accattttag gcaaaacgct caaggtaccg tattatatcg attgttattc tgtcggtgat     300
cttaaataca cgaacgcatc aggcgaatct atcgagagtt atcagtctaa catttcttct     360
aaaagtcgta tcaaaggtaa ctatctgttt ttttctgcct cactcaaggt cgatttcgat     420
acggatagcc tgacggattt cgagaatgcc ttctctcgta ccagtacac gtatgatttg      480
tatattttaa aatcatccgc ggaagccctc aaggaatttc tgaaagagtc agtcaaaacg     540
gcgttggaca aggcggatac cgaagaagac atgaacgacc tgtttaatac ttggggcagt     600
catttcctgt caggcgtagt gatgggtggt tgcgcgcaat acagttcgag tacgaataag     660
tatacctcaa atctgaccaa tagctttgac gttgttgcag cggcatcttt cgctggtttt     720
attggtctgt ccgcccgtac aggcaactca tttatggaag atattaaaaa atttcgctcc     780
gcatctaata ttaagaccca cgcgatcggt ggggatctca gccgcttcga tccgttcggc     840
ggcgccacct ccgccgatca accgtctgcc gaagagatcg cggcggccaa gaaggccttt     900
gaagattgga agccagcgt accaaacgca ccggaattag tgaacttcgc ggattctaat      960
ccgctgaccg gcatttggga gctgtgctcg gatcgtacgc agaaagcgaa actgaaaaaa    1020
cacttcgaga cggtgtgggc cccggcagaa agcgcgaagc gtcgggtaca tgcggattat    1080
atcgacgcag tcgaagtgat ccagagtaat tcttcggggg ttcgccctcc cagtggatat    1140
acgaaaattg attacgacct caataaaggc gccggtgggg attatatcta cctgtgttat    1200
cataaagccc gttatagcgc ttactcagaa aacaaagatt gcgtttctga tttaattatt    1260
attaagggaa acggagcacg cgccccgagc ggttatacga aaattgatgt ggatttgaat    1320
gaggatgcag gtgaaaaata cctgtattta tgctacaaga agcaaagtta cgacaatgtg    1380
gaagcaatca aggggctggc ggtagttggt ggtgacaatt cgcatacccc tgctccgtac    1440
ggttaccgtc ggattgacac cgatgttaac gagggggccg gaggtgagta catttatatc    1500
tgttactcca aagggcctta a                                              1521
```

<210> SEQ ID NO 84
<211> LENGTH: 1485
<212> TYPE: DNA
<213> ORGANISM: artificial sequence
<220> FEATURE:
<223> OTHER INFORMATION: Woodsholea maritima, Photorhabdus luminescens

<400> SEQUENCE: 84

```
atgaaaagct tggatcacgt tgctcatcag aacttactga atgaaccgac tcaccataaa      60
agcaatacca aggcggcgct gatgcgtcat caggaaaaacc tggttgaacg ctatctgccg     120
ggtgtggagg tgattggggc aggttacaac cctttcggcg tatacgcgtc cactgactca     180
gttactgtgc aactttttga ttggcaaagc gcgccatcag aaccggtcat ttttaacccc     240
gattacattg ctccgaaagc tgtgtcagta caacaaaatg atgaagcccg gtatacgaac     300
gttagcggca aaacaatcaa cacgtttcaa aaaaacttct ccctgaaagt tactgtcgcg     360
ggatcctata acttatttag cggtagcgtc agcaatgaat tcagcagcag cgaaactcgc     420
aatgcagaaa acgaatttag ccgcatccaa cagagcatcc gcgtctggtc tctgcgcctc     480
gcgtacacgg attccctgcg tgaatattta aaagcggacg ttcgcgatta tatcgatagc     540
```

```
attcaatcag atgcgcagat tgaaattctg tttgatcgtt acgggtcaca tttccttacc    600
ggcgtggtga tgggtggcgc agcaatcatg gcgtcttcga ccaataaagt acaggtggac    660
cacacatacg agaatgaaac cattgccaag gccagctacg aagccttaac tgggcagatc    720
tctgctgaga ctgcggctaa atatcgccaa agcatgtcgt cgttctccca gaactccgat    780
attcacaaaa ttgtggtcgg cggagacgga gtcgcgggcg cgaaagtgta tagcggtgac    840
aaggcggatt tcgatgcttg ggctgacacc gtggggacgc tccagatttt tgtggacttt    900
gttagcagcg ttcctatgtt gggaatttgg gaactgtgca agatgacgc gcaggcgaaa     960 aagatggaag attactataa taatacgtgg gccccgcgga aaagcaaaga ggctcaaatt   1020
tatgctgatt atatcgacga aattattatt ggcattaata acaccaatac acctccggaa   1080
ggttatattg gcctgaaaag caccaaagat gaaaatctga atagcaaagg caatatttgc   1140
ctgtttatgc ataaagccaa atatgatccg aatattgata taaagattg cattaccgaa    1200 ctgaaattta ttaccgtgcg tgataaatct ccggaaggtg attgggttaa aattccgcag   1260
gatatttata ttagcccgaa tcagtatctg tatctgtgtt atctgcctgc aaaatatagc   1320
gcagaaaaag ccattaaaga tattcagctg ctgtgtagca gctgtggtag cagcatgatt   1380
ctgccgtatg gctataatga tgtgctggat gaacgtggtg aacgtgcaaa tgcaaccgaa   1440
gatgataatg tgcattatct gatttatagc gcaggctgga ataa                    1485

<210> SEQ ID NO 85
<211> LENGTH: 1533
<212> TYPE: DNA
<213> ORGANISM: Photorhabdus luminescens

<400> SEQUENCE: 85
atgtcaaacg ataaaacggg aaaaagtctg gaacaggaaa atagcgagcg cgacgttgaa     60
attcgcgatc gcaactactt tcgcaaattg agcttgtttg acgatactgt tatcgccggt    120
gcggagatga tcggtactag ctacgatgtg tttggcaagt actgcaatgt aggaagctgc    180
atgaacagcc tcttcgatga acgtaaaatc aacgcgagtg aagacaactt taaaaaagtt    240 accatttttag gcaaaacgct caaggtaccg tattatatcg attgttattc tgtcggtgat    300
cttaaataca cgaacgcatc aggcgaatct atcgagagtt atcagtctaa catttcttct    360
aaaagtcgta tcaaaggtaa ctatctgtttt ttttctgcct cactcaaggt cgatttcgat    420
acggatagcc tgacggattt cgagaatgcc ttctctcgta tccagtacac gtatgatttg    480
tatattttaa aatcatccgc ggaagccctc aaggaatttc tgaaagagtc agtcaaaacg    540
gcgttggaca aggcggatac cgaagaagac atgaacgacc tgtttaatac ttggggcagt    600
catttcctgt caggcgtagt gatgggtggt tgcgcgcaat acagttcgag tacgaataag    660
tatacctcaa atctgaccaa tagctttgac gttgttgcag cggcatcttt cgctggtttt    720
attggtctgt ccgcccgtac aggcaactca tttatggaag atattaaaaa atttcgctcc    780
gcatctaata ttaagaccca cgcgatcggt ggggatctca gccgcttcga tccgttcggc    840
ggcgccacct ccgccgatca accgtctgcc gaagagatcg cggcggccaa gaaggccttt    900
gaagattgga aagccagcgt accaaacgca ccggaattag tgaacttcgc ggattctaat    960
ccgctgaccg gcatttggga gctgtgctcg atcgtacgc agaaagcgaa actgaaaaaa   1020
cacttcgaga cggtgtgggc cccggcagaa agcgcgaagc gtcgggtaca tgcggattac   1080
atcgatgaga ttatcattgg tattaacaat accaatacc caccagaagg ctacattgga   1140
```

-continued

```
ttaaaaagta ccaaggatga aaatctcaac agtaaaggaa atatctgctt attcatgcac    1200
aaagctaaat atgacccgaa tatcgacaac aaagattgca ttactgaact gaaatttatc    1260
actgtgcgtg acaagagtcc agaaggtgat tgggttaaaa tcccgcaaga tatctatatt    1320
agtccgaatc agtatctgta cctgtgctat ttgcccgcaa atattcggc cgagaaagcg     1380 atcaaagaca ttcagctgct gtgctcgagc tgtggctcga gcatgattct gccttacggg    1440
tataatgatg tcttagatga gcgcggtgaa cgtgcaaatg ctacggaaga tgataacgtg    1500
cactatctga tttactccgc aggatggaag taa                                  1533
```

<210> SEQ ID NO 86
<211> LENGTH: 492
<212> TYPE: PRT
<213> ORGANISM: artificial sequence
<220> FEATURE:
<223> OTHER INFORMATION: Woodsholea maritima

<400> SEQUENCE: 86

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
        50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
```

```
            290                 295                 300
Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Leu Leu Cys
385                 390                 395                 400

Val Ser Asp Leu Ile Ile Ile Lys Gly Asn Gly Ala Arg Ala Pro Ser
                405                 410                 415

Gly Tyr Thr Lys Ile Asp Val Asp Leu Asn Glu Asp Ala Gly Gly Lys
            420                 425                 430

Tyr Leu Tyr Leu Cys Tyr Lys Lys Gln Ser Tyr Asp Asn Val Glu Ala
        435                 440                 445

Ile Lys Gly Leu Ala Val Val Gly Gly Asp Asn Ser His Thr Pro Ala
    450                 455                 460

Pro Tyr Gly Tyr Arg Arg Ile Asp Thr Asp Val Asn Glu Gly Ala Gly
465                 470                 475                 480

Gly Glu Tyr Ile Tyr Ile Cys Tyr Ser Lys Gly Ala
                485                 490

<210> SEQ ID NO 87
<211> LENGTH: 492
<212> TYPE: PRT
<213> ORGANISM: artificial sequence
<220> FEATURE:
<223> OTHER INFORMATION: Woodsholea maritima

<400> SEQUENCE: 87

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65              70                  75                  80

Asp Tyr Ile Ala Pro Lys Ala Val Ser Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
```

```
                165                 170                 175
Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
        355                 360                 365

Tyr Asp Leu Asn Lys Gly Ala Gly Asp Tyr Ile Tyr Leu Cys Tyr
    370                 375                 380

His Lys Ala Arg Tyr Ser Ala Tyr Ser Glu Asn Lys Asp Cys Leu Leu
385                 390                 395                 400

Val Ser Asp Leu Ile Ile Ile Lys Gly Asn Gly Ala Arg Ala Pro Ser
                405                 410                 415

Gly Tyr Thr Lys Ile Asp Val Asp Leu Asn Glu Asp Ala Gly Gly Lys
            420                 425                 430

Tyr Leu Tyr Leu Cys Tyr Lys Lys Gln Ser Tyr Asp Asn Val Glu Ala
        435                 440                 445

Ile Lys Gly Leu Ala Val Val Gly Gly Asp Asn Ser His Thr Pro Ala
    450                 455                 460

Pro Tyr Gly Tyr Arg Arg Ile Asp Thr Asp Val Asn Glu Gly Ala Gly
465                 470                 475                 480

Gly Glu Tyr Ile Tyr Ile Cys Tyr Ser Lys Gly Ala
                485                 490

<210> SEQ ID NO 88
<211> LENGTH: 492
<212> TYPE: PRT
<213> ORGANISM: artificial sequence
<220> FEATURE:
<223> OTHER INFORMATION: Woodsholea maritima

<400> SEQUENCE: 88

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
```

```
                35                  40                  45
Tyr Asn Pro Phe Gly Val Tyr Ala Ser Thr Asp Ser Val Thr Val Gln
 50                  55                  60

Leu Phe Asp Trp Gln Ser Ala Pro Ser Glu Pro Val Ile Phe Asn Pro
 65                  70                  75                  80

Asp Tyr Ile Ala Pro Lys Ala Val Ser Gln Gln Asn Asp Glu Ala
                 85                  90                  95

Arg Tyr Thr Asn Val Ser Gly Lys Thr Ile Asn Thr Phe Gln Lys Asn
                100                 105                 110

Phe Ser Leu Lys Val Thr Val Ala Gly Ser Tyr Asn Leu Phe Ser Gly
                115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
                180                 185                 190

Arg Tyr Gly Ser His Phe Leu Thr Gly Val Val Met Gly Gly Ala Ala
                195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
                260                 265                 270

Gly Ala Lys Val Tyr Ser Gly Asp Lys Ala Asp Phe Asp Ala Trp Ala
                275                 280                 285

Asp Thr Val Gly Thr Ser Pro Asp Phe Val Asp Phe Val Ser Ser Val
                290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
                340                 345                 350

Ser Asn Ser Ser Gly Val Arg Pro Pro Ser Gly Tyr Thr Lys Ile Asp
                355                 360                 365

Tyr Asp Leu Asn Lys Gly Ala Gly Gly Asp Tyr Ile Tyr Leu Cys Tyr
                370                 375                 380

His Lys Ala Arg Tyr Ser Ala Tyr Ser Glu Asn Lys Asp Leu Cys Leu
385                 390                 395                 400

Val Ser Asp Leu Ile Ile Ile Lys Gly Asn Gly Ala Arg Ala Pro Ser
                405                 410                 415

Gly Tyr Thr Lys Ile Asp Val Asp Leu Asn Glu Asp Ala Gly Gly Lys
                420                 425                 430

Tyr Leu Tyr Leu Cys Tyr Lys Lys Gln Ser Tyr Asp Asn Val Glu Ala
                435                 440                 445

Ile Lys Gly Leu Ala Val Val Gly Gly Asp Asn Ser His Thr Pro Ala
450                 455                 460
```

```
Pro Tyr Gly Tyr Arg Arg Ile Asp Thr Asp Val Asn Glu Gly Ala Gly
465                 470                 475                 480

Gly Glu Tyr Ile Tyr Ile Cys Tyr Ser Lys Gly Ala
            485                 490
```

<210> SEQ ID NO 89
<211> LENGTH: 490
<212> TYPE: PRT
<213> ORGANISM: artificial sequence
<220> FEATURE:
<223> OTHER INFORMATION: Woodsholea maritima

<400> SEQUENCE: 89

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
    115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
    195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
    275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335
```

Glu Ala Gln Ile Tyr Ala Asp Tyr Ile Asp Ala Val Glu Val Ile Gln
                340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Gly Asp Tyr Ile Tyr Leu Cys Tyr
        370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Cys Phe Lys Lys Gln Ser Tyr Asp Asn Val Glu Ala Ile Lys
        435                 440                 445

Gly Leu Ala Val Val Gly Gly Asp Asn Ser His Thr Pro Ala Pro Tyr
    450                 455                 460

Gly Tyr Arg Arg Ile Asp Thr Asp Val Asn Glu Gly Ala Gly Gly Glu
465                 470                 475                 480

Tyr Ile Tyr Ile Cys Tyr Ser Lys Gly Ala
                485                 490

<210> SEQ ID NO 90
<211> LENGTH: 491
<212> TYPE: PRT
<213> ORGANISM: artificial sequence
<220> FEATURE:
<223> OTHER INFORMATION: Woodsholea maritima

<400> SEQUENCE: 90

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
            210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
                260                 265                 270

Gly Ala Lys Val Tyr Ser Gly Asp Lys Ala Asp Phe Asp Ala Trp Ala
            275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
                340                 345                 350

Ser Asn Ser Ser Gly Val Arg Pro Pro Ser Gly Tyr Thr Lys Ile Asp
            355                 360                 365

Tyr Asp Leu Asn Lys Gly Ala Gly Gly Asp Tyr Ile Tyr Leu Cys Tyr
370                 375                 380

His Lys Ala Arg Tyr Ser Ala Tyr Ser Glu Asn Lys Asp Leu Cys Val
385                 390                 395                 400

Ser Asp Leu Ile Ile Ile Lys Gly Asn Gly Ala Arg Ala Pro Ser Gly
                405                 410                 415

Tyr Thr Lys Ile Asp Val Asp Leu Asn Glu Asp Ala Gly Gly Lys Tyr
                420                 425                 430

Leu Tyr Leu Cys Tyr Lys Lys Gln Ser Tyr Asp Asn Val Glu Ala Ile
            435                 440                 445

Lys Gly Leu Ala Val Val Gly Gly Asp Asn Ser His Thr Pro Ala Pro
450                 455                 460

Tyr Gly Tyr Arg Arg Ile Asp Thr Asp Val Asn Glu Gly Ala Gly Gly
465                 470                 475                 480

Glu Tyr Ile Tyr Ile Cys Tyr Ser Lys Gly Ala
                485                 490

<210> SEQ ID NO 91
<211> LENGTH: 491
<212> TYPE: PRT
<213> ORGANISM: artificial sequence
<220> FEATURE:
<223> OTHER INFORMATION: Woodsholea maritima

<400> SEQUENCE: 91

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

```
Asp Tyr Ile Ala Pro Lys Ala Val Ser Val Gln Gln Asn Asp Glu Ala
                85                  90                  95
Arg Tyr Thr Asn Val Ser Gly Lys Thr Ile Asn Thr Phe Gln Lys Asn
            100                 105                 110
Phe Ser Leu Lys Val Thr Val Ala Gly Ser Tyr Asn Leu Phe Ser Gly
        115                 120                 125
Ser Val Ser Asn Glu Phe Ser Ser Glu Thr Arg Asn Ala Glu Asn
    130                 135                 140
Glu Phe Ser Arg Ile Gln Gln Ser Ile Arg Val Trp Ser Leu Arg Leu
145                 150                 155                 160
Ala Tyr Thr Asp Ser Leu Arg Glu Tyr Leu Lys Ala Asp Val Arg Asp
                165                 170                 175
Tyr Ile Asp Ser Ile Gln Ser Asp Ala Gln Ile Glu Ile Leu Phe Asp
            180                 185                 190
Arg Tyr Gly Ser His Phe Leu Thr Gly Val Val Met Gly Gly Ala Ala
        195                 200                 205
Ile Met Ala Ser Ser Thr Asn Lys Val Gln Val Asp His Thr Tyr Glu
    210                 215                 220
Asn Glu Thr Ile Ala Lys Ala Ser Tyr Glu Ala Leu Thr Gly Gln Ile
225                 230                 235                 240
Ser Ala Glu Thr Ala Ala Lys Tyr Arg Gln Ser Met Ser Ser Phe Ser
                245                 250                 255
Gln Asn Ser Asp Ile His Lys Ile Val Val Gly Gly Asp Gly Val Ala
            260                 265                 270
Gly Ala Lys Val Tyr Ser Gly Asp Lys Ala Asp Phe Asp Ala Trp Ala
        275                 280                 285
Asp Thr Val Gly Thr Ser Pro Asp Phe Val Asp Phe Val Ser Ser Val
    290                 295                 300
Pro Met Leu Gly Ile Trp Glu Leu Cys Lys Asp Asp Ala Gln Ala Lys
305                 310                 315                 320
Lys Met Glu Asp Tyr Tyr Asn Asn Thr Trp Ala Pro Arg Lys Ser Lys
                325                 330                 335
Glu Ala Gln Ile Tyr Ala Asp Tyr Ile Asp Ala Val Glu Val Ile Gln
            340                 345                 350
Ser Asn Ser Ser Gly Val Arg Pro Pro Ser Gly Tyr Thr Lys Ile Asp
        355                 360                 365
Tyr Asp Leu Asn Lys Gly Ala Gly Asp Tyr Ile Tyr Leu Cys Tyr
    370                 375                 380
His Lys Ala Arg Tyr Ser Ala Tyr Ser Glu Asn Lys Asp Cys Leu Val
385                 390                 395                 400
Ser Asp Leu Ile Ile Lys Gly Asn Gly Ala Arg Ala Pro Ser Gly
                405                 410                 415
Tyr Thr Lys Ile Asp Val Asp Leu Asn Glu Asp Ala Gly Gly Lys Tyr
            420                 425                 430
Leu Tyr Leu Cys Tyr Lys Lys Gln Ser Tyr Asp Asn Val Glu Ala Ile
        435                 440                 445
Lys Gly Leu Ala Val Val Gly Gly Asp Asn Ser His Thr Pro Ala Pro
    450                 455                 460
Tyr Gly Tyr Arg Arg Ile Asp Thr Asp Val Asn Glu Gly Ala Gly Gly
465                 470                 475                 480
Glu Tyr Ile Tyr Ile Cys Tyr Ser Lys Gly Ala
                485                 490
```

<210> SEQ ID NO 92
<211> LENGTH: 491
<212> TYPE: PRT
<213> ORGANISM: artificial sequence
<220> FEATURE:
<223> OTHER INFORMATION: Woodsholea maritima

<400> SEQUENCE: 92

```
Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Gln Gln Asn Asp Glu Ala
                85                  90                  95

Arg Tyr Thr Asn Val Ser Gly Lys Thr Ile Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
    130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365
```

Tyr Asp Leu Asn Lys Gly Ala Gly Asp Tyr Ile Tyr Leu Leu Cys
    370                 375                 380

Tyr His Lys Ala Arg Tyr Ser Ala Tyr Ser Glu Asn Lys Asp Cys Val
385                 390                 395                 400

Ser Asp Leu Ile Ile Ile Lys Gly Asn Gly Ala Arg Ala Pro Ser Gly
                405                 410                 415

Tyr Thr Lys Ile Asp Val Asp Leu Asn Glu Asp Ala Gly Gly Lys Tyr
                420                 425                 430

Leu Tyr Leu Cys Tyr Lys Lys Gln Ser Tyr Asp Asn Val Glu Ala Ile
            435                 440                 445

Lys Gly Leu Ala Val Val Gly Gly Asp Asn Ser His Thr Pro Ala Pro
450                 455                 460

Tyr Gly Tyr Arg Arg Ile Asp Thr Asp Val Asn Glu Gly Ala Gly Gly
465                 470                 475                 480

Glu Tyr Ile Tyr Ile Cys Tyr Ser Lys Gly Ala
                485                 490

<210> SEQ ID NO 93
<211> LENGTH: 491
<212> TYPE: PRT
<213> ORGANISM: artificial sequence
<220> FEATURE:
<223> OTHER INFORMATION: Woodsholea maritima

<400> SEQUENCE: 93

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
        50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
                100                 105                 110

Phe Ser Leu Lys Val Thr Val Ala Gly Ser Tyr Asn Leu Phe Ser Gly
            115                 120                 125

Ser Val Ser Asn Glu Phe Ser Ser Glu Thr Arg Asn Ala Glu Asn
        130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
                180                 185                 190

Arg Tyr Gly Ser His Phe Leu Thr Gly Val Val Met Gly Gly Ala Ala
            195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

```
Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Ser Gly Tyr Thr Lys Ile Asp
        355                 360                 365

Tyr Asp Leu Asn Lys Gly Ala Gly Gly Asp Tyr Ile Tyr Leu Cys Leu
    370                 375                 380

Tyr His Lys Ala Arg Tyr Ser Ala Tyr Ser Glu Asn Lys Asp Cys Val
385                 390                 395                 400

Ser Asp Leu Ile Ile Ile Lys Gly Asn Gly Ala Arg Ala Pro Ser Gly
                405                 410                 415

Tyr Thr Lys Ile Asp Val Asp Leu Asn Glu Asp Ala Gly Gly Lys Tyr
            420                 425                 430

Leu Tyr Leu Cys Tyr Lys Lys Gln Ser Tyr Asp Asn Val Glu Ala Ile
        435                 440                 445

Lys Gly Leu Ala Val Val Gly Gly Asp Asn Ser His Thr Pro Ala Pro
    450                 455                 460

Tyr Gly Tyr Arg Arg Ile Asp Thr Asp Val Asn Glu Gly Ala Gly Gly
465                 470                 475                 480

Glu Tyr Ile Tyr Ile Cys Tyr Ser Lys Gly Ala
                485                 490

<210> SEQ ID NO 94
<211> LENGTH: 491
<212> TYPE: PRT
<213> ORGANISM: artificial sequence
<220> FEATURE:
<223> OTHER INFORMATION: Woodsholea maritima

<400> SEQUENCE: 94

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
                20                  25                  30

Asn Leu Val Glu Arg Tyr Leu Pro Gly Val Glu Val Ile Gly Ala Gly
            35                  40                  45

Tyr Asn Pro Phe Gly Val Tyr Ala Ser Thr Asp Ser Val Thr Val Gln
        50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110
```

Phe Ser Leu Lys Val Thr Val Ala Gly Ser Tyr Asn Leu Phe Ser Gly
            115                 120                 125

Ser Val Ser Asn Glu Phe Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
    210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr
                405                 410                 415

Thr Lys Ile Asp Val Asp Leu Asn Glu Asp Ala Gly Gly Lys Tyr Leu
            420                 425                 430

Tyr Leu Leu Cys Tyr Lys Lys Gln Ser Tyr Asp Asn Val Glu Ala Ile
        435                 440                 445

Lys Gly Leu Ala Val Val Gly Gly Asp Asn Ser His Thr Pro Ala Pro
450                 455                 460

Tyr Gly Tyr Arg Arg Ile Asp Thr Asp Val Asn Glu Gly Ala Gly Gly
465                 470                 475                 480

Glu Tyr Ile Tyr Ile Cys Tyr Ser Lys Gly Ala
                485                 490

<210> SEQ ID NO 95
<211> LENGTH: 491
<212> TYPE: PRT
<213> ORGANISM: artificial sequence
<220> FEATURE:
<223> OTHER INFORMATION: Woodsholea maritima

<400> SEQUENCE: 95

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Glu Thr Arg Asn Ala Glu Asn
130                 135                 140

Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
    290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Ala Val Glu Val Ile Gln
            340                 345                 350

Ser Asn Ser Ser Gly Val Arg Pro Pro Ser Gly Tyr Thr Lys Ile Asp
        355                 360                 365

Tyr Asp Leu Asn Lys Gly Ala Gly Gly Asp Tyr Ile Tyr Leu Cys Tyr
    370                 375                 380

His Lys Ala Arg Tyr Ser Ala Tyr Ser Glu Asn Lys Asp Cys Val Ser
385                 390                 395                 400

Asp Leu Ile Ile Ile Lys Gly Asn Gly Ala Arg Ala Pro Ser Gly Tyr

```
                            405                 410                 415
Thr Lys Ile Asp Val Asp Leu Asn Glu Asp Ala Gly Gly Lys Tyr Leu
            420                 425                 430

Tyr Leu Cys Leu Tyr Lys Lys Gln Ser Tyr Asp Asn Val Glu Ala Ile
            435                 440                 445

Lys Gly Leu Ala Val Val Gly Gly Asp Asn Ser His Thr Pro Ala Pro
            450                 455                 460

Tyr Gly Tyr Arg Arg Ile Asp Thr Asp Val Asn Glu Gly Ala Gly Gly
465                 470                 475                 480

Glu Tyr Ile Tyr Ile Cys Tyr Ser Lys Gly Ala
                485                 490

<210> SEQ ID NO 96
<211> LENGTH: 506
<212> TYPE: PRT
<213> ORGANISM: artificial sequence
<220> FEATURE:
<223> OTHER INFORMATION: Woodsholea maritima, Photorhabdus luminescens

<400> SEQUENCE: 96

Met Ser Asn Asp Lys Thr Gly Lys Ser Leu Glu Gln Glu Asn Ser Glu
1               5                   10                  15

Arg Asp Val Glu Ile Arg Asp Arg Asn Tyr Phe Arg Lys Leu Ser Leu
            20                  25                  30

Phe Asp Thr Val Ile Ala Gly Ala Glu Met Ile Gly Thr Ser Tyr
        35                  40                  45

Asp Val Phe Gly Lys Tyr Cys Asn Val Gly Ser Cys Met Asn Ser Leu
50                  55                  60

Phe Asp Glu Arg Lys Ile Asn Ala Ser Glu Asp Asn Phe Lys Lys Val
65                  70                  75                  80

Thr Ile Leu Gly Lys Thr Leu Lys Val Pro Tyr Tyr Ile Asp Cys Tyr
                85                  90                  95

Ser Val Gly Asp Leu Lys Tyr Thr Asn Ala Ser Gly Glu Ser Ile Glu
            100                 105                 110

Ser Tyr Gln Ser Asn Ile Ser Ser Lys Ser Arg Ile Lys Gly Asn Tyr
        115                 120                 125

Leu Phe Phe Ser Ala Ser Leu Lys Val Asp Phe Asp Thr Asp Ser Leu
130                 135                 140

Thr Asp Phe Glu Asn Ala Phe Ser Arg Ile Gln Tyr Thr Tyr Asp Leu
145                 150                 155                 160

Tyr Ile Leu Lys Ser Ser Ala Glu Ala Leu Lys Glu Phe Leu Lys Glu
                165                 170                 175

Ser Val Lys Thr Ala Leu Asp Lys Ala Asp Thr Glu Glu Asp Met Asn
            180                 185                 190

Asp Leu Phe Asn Thr Trp Gly Ser His Phe Leu Ser Gly Val Val Met
        195                 200                 205

Gly Gly Cys Ala Gln Tyr Ser Ser Thr Asn Lys Tyr Thr Ser Asn
210                 215                 220

Leu Thr Asn Ser Phe Asp Val Val Ala Ala Ser Phe Ala Gly Phe
225                 230                 235                 240

Ile Gly Leu Ser Ala Arg Thr Gly Asn Ser Phe Met Glu Asp Ile Lys
                245                 250                 255

Lys Phe Arg Ser Ala Ser Asn Ile Lys Thr His Ala Ile Gly Gly Asp
            260                 265                 270

Leu Ser Arg Phe Asp Pro Phe Gly Gly Ala Thr Ser Ala Asp Gln Pro
```

```
                275                 280                 285
Ser Ala Glu Glu Ile Ala Ala Lys Lys Ala Phe Glu Asp Trp Lys
    290                 295                 300

Ala Ser Val Pro Asn Ala Pro Glu Leu Val Asn Phe Ala Asp Ser Asn
305                 310                 315                 320

Pro Leu Thr Gly Ile Trp Glu Leu Cys Ser Asp Arg Thr Gln Lys Ala
                325                 330                 335

Lys Leu Lys Lys His Phe Glu Thr Val Trp Ala Pro Ala Glu Ser Ala
            340                 345                 350

Lys Arg Arg Val His Ala Asp Tyr Ile Asp Ala Val Glu Val Ile Gln
        355                 360                 365

Ser Asn Ser Ser Gly Val Arg Pro Pro Ser Gly Tyr Thr Lys Ile Asp
    370                 375                 380

Tyr Asp Leu Asn Lys Gly Ala Gly Asp Tyr Ile Tyr Leu Cys Tyr
385                 390                 395                 400

His Lys Ala Arg Tyr Ser Ala Tyr Ser Glu Asn Lys Asp Cys Val Ser
                405                 410                 415

Asp Leu Ile Ile Ile Lys Gly Asn Gly Ala Arg Ala Pro Ser Gly Tyr
            420                 425                 430

Thr Lys Ile Asp Val Asp Leu Asn Glu Asp Ala Gly Gly Lys Tyr Leu
        435                 440                 445

Tyr Leu Cys Tyr Lys Lys Gln Ser Tyr Asp Asn Val Glu Ala Ile Lys
    450                 455                 460

Gly Leu Ala Val Val Gly Gly Asp Asn Ser His Thr Pro Ala Pro Tyr
465                 470                 475                 480

Gly Tyr Arg Arg Ile Asp Thr Asp Val Asn Glu Gly Ala Gly Gly Glu
                485                 490                 495

Tyr Ile Tyr Ile Cys Tyr Ser Lys Gly Ala
            500                 505

<210> SEQ ID NO 97
<211> LENGTH: 494
<212> TYPE: PRT
<213> ORGANISM: artificial sequence
<220> FEATURE:
<223> OTHER INFORMATION: Woodsholea maritima, Photorhabdus luminescens

<400> SEQUENCE: 97

Met Lys Ser Leu Asp His Val Ala His Gln Asn Leu Leu Asn Glu Pro
1               5                   10                  15

Thr His His Lys Ser Asn Thr Lys Ala Ala Leu Met Arg His Gln Glu
            20                  25                  30

Asn Leu Val Glu Arg Tyr Leu Pro Gly Val Glu Val Ile Gly Ala Gly
        35                  40                  45

Tyr Asn Pro Phe Gly Val Tyr Ala Ser Thr Asp Ser Val Thr Val Gln
    50                  55                  60

Leu Phe Asp Trp Gln Ser Ala Pro Ser Glu Pro Val Ile Phe Asn Pro
65                  70                  75                  80

Asp Tyr Ile Ala Pro Lys Ala Val Ser Val Gln Gln Asn Asp Glu Ala
                85                  90                  95

Arg Tyr Thr Asn Val Ser Gly Lys Thr Ile Asn Thr Phe Gln Lys Asn
            100                 105                 110

Phe Ser Leu Lys Val Thr Val Ala Gly Ser Tyr Asn Leu Phe Ser Gly
        115                 120                 125

Ser Val Ser Asn Glu Phe Ser Ser Ser Glu Thr Arg Asn Ala Glu Asn
```

```
            130                 135                 140
Glu Phe Ser Arg Ile Gln Gln Ser Ile Arg Val Trp Ser Leu Arg Leu
145                 150                 155                 160

Ala Tyr Thr Asp Ser Leu Arg Glu Tyr Leu Lys Ala Asp Val Arg Asp
                165                 170                 175

Tyr Ile Asp Ser Ile Gln Ser Asp Ala Gln Ile Glu Ile Leu Phe Asp
            180                 185                 190

Arg Tyr Gly Ser His Phe Leu Thr Gly Val Val Met Gly Gly Ala Ala
        195                 200                 205

Ile Met Ala Ser Ser Thr Asn Lys Val Gln Val Asp His Thr Tyr Glu
210                 215                 220

Asn Glu Thr Ile Ala Lys Ala Ser Tyr Glu Ala Leu Thr Gly Gln Ile
225                 230                 235                 240

Ser Ala Glu Thr Ala Ala Lys Tyr Arg Gln Ser Met Ser Ser Phe Ser
                245                 250                 255

Gln Asn Ser Asp Ile His Lys Ile Val Val Gly Gly Asp Gly Val Ala
            260                 265                 270

Gly Ala Lys Val Tyr Ser Gly Asp Lys Ala Asp Phe Asp Ala Trp Ala
        275                 280                 285

Asp Thr Val Gly Thr Ser Pro Asp Phe Val Asp Phe Val Ser Ser Val
290                 295                 300

Pro Met Leu Gly Ile Trp Glu Leu Cys Lys Asp Asp Ala Gln Ala Lys
305                 310                 315                 320

Lys Met Glu Asp Tyr Tyr Asn Asn Thr Trp Ala Pro Arg Lys Ser Lys
                325                 330                 335

Glu Ala Gln Ile Tyr Ala Asp Tyr Ile Asp Glu Ile Ile Gly Ile
            340                 345                 350

Asn Asn Thr Asn Thr Pro Pro Glu Gly Tyr Ile Gly Leu Lys Ser Thr
        355                 360                 365

Lys Asp Glu Asn Leu Asn Ser Lys Gly Asn Ile Cys Leu Phe Met His
370                 375                 380

Lys Ala Lys Tyr Asp Pro Asn Ile Asp Asn Lys Asp Cys Ile Thr Glu
385                 390                 395                 400

Leu Lys Phe Ile Thr Val Arg Asp Lys Ser Pro Glu Gly Asp Trp Val
                405                 410                 415

Lys Ile Pro Gln Asp Ile Tyr Ile Ser Pro Asn Gln Tyr Leu Tyr Leu
            420                 425                 430

Cys Tyr Leu Pro Ala Lys Tyr Ser Ala Glu Lys Ala Ile Lys Asp Ile
        435                 440                 445

Gln Leu Leu Cys Ser Ser Cys Gly Ser Ser Met Ile Leu Pro Tyr Gly
450                 455                 460

Tyr Asn Asp Val Leu Asp Glu Arg Gly Glu Arg Ala Asn Ala Thr Glu
465                 470                 475                 480

Asp Asp Asn Val His Tyr Leu Ile Tyr Ser Ala Gly Trp Lys
                485                 490
```

<210> SEQ ID NO 98
<211> LENGTH: 510
<212> TYPE: PRT
<213> ORGANISM: Photorhabdus luminescens

<400> SEQUENCE: 98

```
Met Ser Asn Asp Lys Thr Gly Lys Ser Leu Glu Gln Glu Asn Ser Glu
1               5                   10                  15
```

-continued

```
Arg Asp Val Glu Ile Arg Asp Arg Asn Tyr Phe Arg Lys Leu Ser Leu
             20                  25                  30

Phe Asp Asp Thr Val Ile Ala Gly Ala Glu Met Ile Gly Thr Ser Tyr
         35                  40                  45

Asp Val Phe Gly Lys Tyr Cys Asn Val Gly Ser Cys Met Asn Ser Leu
 50                  55                  60

Phe Asp Glu Arg Lys Ile Asn Ala Ser Glu Asp Asn Phe Lys Lys Val
65                  70                  75                  80

Thr Ile Leu Gly Lys Thr Leu Lys Val Pro Tyr Tyr Ile Asp Cys Tyr
                 85                  90                  95

Ser Val Gly Asp Leu Lys Tyr Thr Asn Ala Ser Gly Glu Ser Ile Glu
                100                 105                 110

Ser Tyr Gln Ser Asn Ile Ser Ser Lys Ser Arg Ile Lys Gly Asn Tyr
            115                 120                 125

Leu Phe Phe Ser Ala Ser Leu Lys Val Asp Phe Asp Thr Asp Ser Leu
130                 135                 140

Thr Asp Phe Glu Asn Ala Phe Ser Arg Ile Gln Tyr Thr Tyr Asp Leu
145                 150                 155                 160

Tyr Ile Leu Lys Ser Ser Ala Glu Ala Leu Lys Glu Phe Leu Lys Glu
                165                 170                 175

Ser Val Lys Thr Ala Leu Asp Lys Ala Asp Thr Glu Glu Asp Met Asn
                180                 185                 190

Asp Leu Phe Asn Thr Trp Gly Ser His Phe Leu Ser Gly Val Val Met
            195                 200                 205

Gly Gly Cys Ala Gln Tyr Ser Ser Ser Thr Asn Lys Tyr Thr Ser Asn
210                 215                 220

Leu Thr Asn Ser Phe Asp Val Val Ala Ala Ser Phe Ala Gly Phe
225                 230                 235                 240

Ile Gly Leu Ser Ala Arg Thr Gly Asn Ser Phe Met Glu Asp Ile Lys
                245                 250                 255

Lys Phe Arg Ser Ala Ser Asn Ile Lys Thr His Ala Ile Gly Gly Asp
                260                 265                 270

Leu Ser Arg Phe Asp Pro Phe Gly Gly Ala Thr Ser Ala Asp Gln Pro
            275                 280                 285

Ser Ala Glu Glu Ile Ala Ala Lys Lys Ala Phe Glu Asp Trp Lys
290                 295                 300

Ala Ser Val Pro Asn Ala Pro Glu Leu Val Asn Phe Ala Asp Ser Asn
305                 310                 315                 320

Pro Leu Thr Gly Ile Trp Glu Leu Cys Ser Asp Arg Thr Gln Lys Ala
                325                 330                 335

Lys Leu Lys Lys His Phe Glu Thr Val Trp Ala Pro Ala Glu Ser Ala
            340                 345                 350

Lys Arg Arg Val His Ala Asp Tyr Ile Asp Glu Ile Ile Gly Ile
            355                 360                 365

Asn Asn Thr Asn Thr Pro Pro Glu Gly Tyr Ile Gly Leu Lys Ser Thr
370                 375                 380

Lys Asp Glu Asn Leu Asn Ser Lys Gly Asn Ile Cys Leu Phe Met His
385                 390                 395                 400

Lys Ala Lys Tyr Asp Pro Asn Ile Asp Asn Lys Asp Cys Ile Thr Glu
                405                 410                 415

Leu Lys Phe Ile Thr Val Arg Asp Lys Ser Pro Glu Gly Asp Trp Val
            420                 425                 430
```

```
Lys Ile Pro Gln Asp Ile Tyr Ile Ser Pro Asn Gln Tyr Leu Tyr Leu
        435                 440                 445

Cys Tyr Leu Pro Ala Lys Tyr Ser Ala Glu Lys Ala Ile Lys Asp Ile
450                 455                 460

Gln Leu Leu Cys Ser Ser Cys Gly Ser Ser Met Ile Leu Pro Tyr Gly
465                 470                 475                 480

Tyr Asn Asp Val Leu Asp Glu Arg Gly Glu Arg Ala Asn Ala Thr Glu
                485                 490                 495

Asp Asp Asn Val His Tyr Leu Ile Tyr Ser Ala Gly Trp Lys
                500                 505                 510

<210> SEQ ID NO 99
<211> LENGTH: 433
<212> TYPE: DNA
<213> ORGANISM: artificial sequence
<220> FEATURE:
<223> OTHER INFORMATION: Woodsholea maritima

<400> SEQUENCE: 99
cgcagtcgaa gtgatccaga gtaattcttc gggggttcgc cctcccagtg atatacgaa      60 aattgattac gacctcaata aaggcgccgg tggggattat atctacctgt gttatcataa    120
agcccgttat agcgcttact cagaaaacaa agattgcgtt tctgatttaa ttattattaa    180
gggaaacgga gcacgcgccc cgagcggtta tacgaaaatt gatgtggatt tgaatgagga    240
tgcaggtgga aaatacctgt atttatgcta caagaagcaa agttacgaca atgtggaagc    300
aatcaagggg ctggcggtag ttggtggtga caattcgcat accccctgctc cgtacggtta    360 ccgtcggatt gacaccgatg ttaacgaggg ggccggaggt gagtacattt atatctgtta    420
ctccaaaggg gct                                                        433

<210> SEQ ID NO 100
<211> LENGTH: 144
<212> TYPE: PRT
<213> ORGANISM: artificial sequence
<220> FEATURE:
<223> OTHER INFORMATION: Woodsholea maritima

<400> SEQUENCE: 100

Ala Val Glu Val Ile Gln Ser Asn Ser Ser Gly Val Arg Pro Pro Ser
1               5                   10                  15

Gly Tyr Thr Lys Ile Asp Tyr Asp Leu Asn Lys Gly Ala Gly Gly Asp
                20                  25                  30

Tyr Ile Tyr Leu Cys Tyr His Lys Ala Arg Tyr Ser Ala Tyr Ser Glu
            35                  40                  45

Asn Lys Asp Cys Val Ser Asp Leu Ile Ile Ile Lys Gly Asn Gly Ala
    50                  55                  60

Arg Ala Pro Ser Gly Tyr Thr Lys Ile Asp Val Asp Leu Asn Glu Asp
65                  70                  75                  80

Ala Gly Gly Lys Tyr Leu Tyr Leu Cys Tyr Lys Lys Gln Ser Tyr Asp
                85                  90                  95

Asn Val Glu Ala Ile Lys Gly Leu Ala Val Val Gly Gly Asp Asn Ser
            100                 105                 110

His Thr Pro Ala Pro Tyr Gly Tyr Arg Arg Ile Asp Thr Asp Val Asn
        115                 120                 125

Glu Gly Ala Gly Gly Tyr Ile Tyr Ile Cys Tyr Ser Lys Gly Ala
    130                 135                 140
```

INSECTICIDAL PROTEINS

RELATED APPLICATION INFORMATION

This application is a 371 of International Application No. PCT/2018/012730, filed Jan. 8, 2018, which claims priority to U.S. Provisional Application No. 62/445,429 filed Jan. 12, 2017, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled "81158_ST25.txt", 219 kilobytes in size, generated on Dec. 22, 2016 and filed via EFS-Web is provided in lieu of a paper copy. This Sequence Listing is hereby incorporated by reference into the specification for its disclosures.

FIELD OF THE INVENTION

The present invention relates to the fields of protein engineering, plant molecular biology and pest control. More particularly the invention relates to a novel protein and its variants having insecticidal activity, nucleic acids whose expression results in the insecticidal proteins, and methods of making and methods of using the insecticidal proteins and corresponding nucleic acids to control insects.

BACKGROUND

Insect pests are a major cause of crop losses. In the US alone, billions of dollars are lost every year due to infestation by various genera of insects. In addition to losses in field crops, insect pests are also a burden to vegetable and fruit growers, to producers of ornamental flowers, and they are a nuisance to gardeners and homeowners.

Species of corn rootworm are considered to be the most destructive corn pests. In the United States, the three important species are *Diabrotica virgifera virgifera*, the western corn rootworm, *D. longicornis barberi*, the northern corn rootworm and *D. undecimpunctata howardi*, the southern corn rootworm. Only western and northern corn rootworms are considered primary pests of corn in the US Corn Belt. Additionally, an important corn rootworm pest in the Southern US is the Mexican corn rootworm, *Diabrotica virgifera zeae*. Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections which lead to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect varieties. Yet another problem is due to the fact that corn rootworm larvae feed underground thus making it difficult to apply rescue treatments of insecticides. Therefore, most insecticide applications are made prophylactically at the time of planting. This practice results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins (delta-endotoxins; also called crystal toxins or Cry proteins), have been applied to crop plants with satisfactory results against insect pests. The δ-endotoxins are proteins held within a crystalline matrix that are known to possess insecticidal activity when ingested by certain insects. Several native Cry proteins from *Bacillus thuringiensis*, or engineered Cry proteins, have been expressed in transgenic crop plants and exploited commercially to control certain lepidopteran and coleopteran insect pests. For example, starting in 2003, transgenic corn hybrids that control corn rootworm by expressing a Cry3Bb1, Cry34Ab1/Cry35Ab1 or modified Cry3A (mCry3A) or Cry3Ab (eCry3.1Ab) protein have been available commercially in the US.

Although the usage of transgenic plants expressing Cry proteins has been shown to be extremely effective, insect pests that now have resistance against the Cry proteins expressed in certain transgenic plants are known. Therefore, there remains a need to identify new and effective pest control agents that provide an economic benefit to farmers and that are environmentally acceptable. Particularly needed are proteins that are toxic to *Diabrotica* species, a major pest of corn, that have a different mode of action than existing insect control products as a way to mitigate the development of resistance. Furthermore, delivery of insect control agents through products that minimize the burden on the environment, as through transgenic plants, are desirable.

SUMMARY

In view of these needs, the present invention provides novel insecticidal proteins, namely WoodsCRW and proteins which are substantially identical to WoodsCRW and its variants. The proteins of the invention have toxicity to corn rootworm (*Diabrotica* spp). The proteins of the invention may also have toxicity to other Coleopterans and/or to Lepidopterans. The invention is further drawn to nucleic acid molecules that encode WoodsCRW or its variants, their complements, or which are substantially identical to WoodsCRW and its variants.

Also included in the invention are vectors containing such recombinant (or complementary thereto) nucleic acids; a plant or microorganism which includes and enables expression of such nucleic acids; plants transformed with such nucleic acids, for example transgenic corn plants; the progeny of such plants which contain the nucleic acids stably incorporated and hereditable in a Mendelian manner, and/or the seeds of such plants and such progeny. The invention also includes methods of breeding to introduce a transgene comprising a nucleic acid molecule of the invention into a progeny plant and into various germplasms.

The invention also includes compositions and formulations containing WoodsCRW or its variants, which are capable of inhibiting the ability of insect pests to survive, grow and/or reproduce, or of limiting insect-related damage or loss to crop plants, for example applying WoodsCRW or its variants as part of compositions or formulations to insect-infested areas or plants, or to prophylactically treat insect-susceptible areas or plants to confer protection against the insect pests.

The invention is further drawn to a method of making WoodsCRW or its variants and to methods of using the nucleic acids, for example in microorganisms to control insects or in transgenic plants to confer protection from insect damage.

The novel proteins described herein are active against insects. For example, in embodiments, the proteins of the present invention can be used to control economically important insect pests, including Coleopteran insects such as western corn rootworm (WCR), northern corn rootworm (NCR), southern corn rootworm (SCR) and/or Mexican corn rootworm (*D. virgifera zeae*). The insecticidal proteins of the invention can be used singly or in combination with other insect control strategies to confer enhanced pest control efficiency against the same insect pest and/or to increase the spectrum of target insects with minimal environmental impact.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

SEQ ID NO: 1 is the WoodsCRW amino acid sequence.
SEQ ID NO: 2 is the WoodsCRW *E. coli* optimized nucleotide sequence
SEQ ID NO: 3 is the WoodsCRW native nucleotide sequence.
SEQ ID NO: 4 is the WoodsCRW variant C485S nucleotide sequence.
SEQ ID NO: 5 is the WoodsCRW variant C435S nucleotide sequence.
SEQ ID NO: 6 is the WoodsCRW variant C398S nucleotide sequence.
SEQ ID NO: 7 is the WoodsCRW variant C383S nucleotide sequence.
SEQ ID NO: 8 is the WoodsCRW variant C313S nucleotide sequence.
SEQ ID NO: 9 is the WoodsCRW variant Y194W nucleotide sequence.
SEQ ID NO: 10 is the WoodsCRW variant Y194F nucleotide sequence.
SEQ ID NO: 11 is the WoodsCRW variant C383S/C485S nucleotide sequence.
SEQ ID NO: 12 is the WoodsCRW variant C435S/C485S nucleotide sequence.
SEQ ID NO: 13 is the WoodsCRW variant C398S/C435S nucleotide sequence.
SEQ ID NO: 14 is the WoodsCRW variant C398S/C485S nucleotide sequence.
SEQ ID NO: 15 is the WoodsCRW variant C383S/C435S/C485S nucleotide sequence.
SEQ ID NO: 16 is the WoodsCRW variant C313S/C383S/C398S/C435S/C485S nucleotide sequence.
SEQ ID NO: 17 is the WoodsCRW variant K396L nucleotide sequence.
SEQ ID NO: 18 is the WoodsCRW variant K406L nucleotide sequence.
SEQ ID NO: 19 is the WoodsCRW variant C383A/C485A nucleotide sequence.
SEQ ID NO: 20 is the WoodsCRW variant C398A/C485A nucleotide sequence.
SEQ ID NO: 21 is the WoodsCRW variant C383L nucleotide sequence.
SEQ ID NO: 22 is the WoodsCRW variant C398L nucleotide sequence.
SEQ ID NO: 23 is the WoodsCRW variant I77L/I83L/Y98F nucleotide sequence.
SEQ ID NO: 24 is the WoodsCRW variant Y248F/I264L/Y277F nucleotide sequence.
SEQ ID NO: 25 is the WoodsCRW variant Y326F/I340L/I351L nucleotide sequence.
SEQ ID NO: 26 is the WoodsCRW variant I209L/Y223F/I228L nucleotide sequence.
SEQ ID NO: 27 is the WoodsCRW variant I447L/Y464F/I469L nucleotide sequence.
SEQ ID NO: 28 is the WoodsCRW variant C435L nucleotide sequence.
SEQ ID NO: 29 is the WoodsCRW variant C485L nucleotide sequence.
SEQ ID NO: 30 is the WoodsCRW variant I403L/I404L nucleotide sequence.
SEQ ID NO: 31 is the WoodsCRW variant V399L nucleotide sequence.
SEQ ID NO: 32 is the WoodsCRW variant V399F nucleotide sequence.
SEQ ID NO: 33 is the WoodsCRW variant C398F nucleotide sequence.
SEQ ID NO: 34 is the WoodsCRW variant C398Y nucleotide sequence.
SEQ ID NO: 35 is the WoodsCRW variant C398I nucleotide sequence.
SEQ ID NO: 36 is the WoodsCRW variant C398M nucleotide sequence.
SEQ ID NO: 37 is the WoodsCRW variant C485S amino acid sequence.
SEQ ID NO: 38 is the WoodsCRW variant C435S amino acid sequence.
SEQ ID NO: 39 is the WoodsCRW variant C398S amino acid sequence.
SEQ ID NO: 40 is the WoodsCRW variant C383S amino acid sequence.
SEQ ID NO: 41 is the WoodsCRW variant C313S amino acid sequence.
SEQ ID NO: 42 is the WoodsCRW variant Y194W amino acid sequence.
SEQ ID NO: 43 is the WoodsCRW variant Y194F amino acid sequence.
SEQ ID NO: 44 is the WoodsCRW variant K396L amino acid sequence.
SEQ ID NO: 45 is the WoodsCRW variant K406L amino acid sequence.
SEQ ID NO: 46 is the WoodsCRW variant C383S/C485S amino acid sequence.
SEQ ID NO: 47 is the WoodsCRW variant C435S/C485S amino acid sequence.
SEQ ID NO: 48 is the WoodsCRW variant C398S/C435S amino acid sequence.
SEQ ID NO: 49 is the WoodsCRW variant C398S/C485S amino acid sequence.
SEQ ID NO: 50 is the WoodsCRW variant C383S/C435S/C485S amino acid sequence.
SEQ ID NO: 51 is the WoodsCRW variant C313S/C383S/C398S/C435S/C485S amino acid sequence.
SEQ ID NO: 52 is the WoodsCRW variant C383A/C485A amino acid sequence.
SEQ ID NO: 53 is the WoodsCRW variant C398A/C485A amino acid sequence.
SEQ ID NO: 54 is the WoodsCRW variant C383L amino acid sequence.

SEQ ID NO: 55 is the WoodsCRW variant C398L amino acid sequence.

SEQ ID NO: 56 is the WoodsCRW variant I77L/I83L/Y98F amino acid sequence.

SEQ ID NO: 57 is the WoodsCRW variant Y248F/I264L/Y277F amino acid sequence.

SEQ ID NO: 58 is the WoodsCRW variant Y326F/I340L/I351L amino acid sequence.

SEQ ID NO: 59 is the WoodsCRW variant I209L/Y223F/I228L amino acid sequence.

SEQ ID NO: 60 is the WoodsCRW variant I447L/Y464F/I469L amino acid sequence.

SEQ ID NO: 61 is the WoodsCRW variant C435L amino acid sequence.

SEQ ID NO: 62 is the WoodsCRW variant C485L amino acid sequence.

SEQ ID NO: 63 is the WoodsCRW variant I403L/I404L amino acid sequence.

SEQ ID NO: 64 is the WoodsCRW variant V399L amino acid sequence.

SEQ ID NO: 65 is the WoodsCRW variant V399F amino acid sequence.

SEQ ID NO: 66 is the WoodsCRW variant C398F amino acid sequence.

SEQ ID NO: 67 is the WoodsCRW variant C398Y amino acid sequence.

SEQ ID NO: 68 is the WoodsCRW variant C398I amino acid sequence.

SEQ ID NO: 69 is the WoodsCRW variant C398M amino acid sequence.

SEQ ID NO: 70 and 71 are amino acid sequences of fragments of WoodsCRW.

SEQ ID NO: 72 is a WoodsCRW amino acid sequence, where "X" can be any amino acid.

SEQ ID NO: 73 is the nucleotide sequence of the WoodsCRW variant D397-Leu-Leu-C398, comprising two inserted leucine residues.

SEQ ID NO: 74 is the nucleotide sequence of the WoodsCRW variant C398-Leu-Leu-V399, comprising two inserted leucine residues.

SEQ ID NO: 75 is the nucleotide sequence of the WoodsCRW variant D397-Leu-C398-Leu, comprising two inserted leucine residues.

SEQ ID NO: 76 is the nucleotide sequence of the WoodsCRW variant Y436F.

SEQ ID NO: 77 is the nucleotide sequence of the WoodsCRW variant D397-Leu-C398, comprising one inserted leucine residue.

SEQ ID NO: 78 is the nucleotide sequence of the WoodsCRW variant C398-Leu-V399, comprising one inserted leucine residue.

SEQ ID NO: 79 is the nucleotide sequence of the WoodsCRW variant L382-Leu-C383, comprising one inserted leucine residue.

SEQ ID NO: 80 is the nucleotide sequence of the WoodsCRW variant C383-Leu-Y384, comprising one inserted leucine residue.

SEQ ID NO: 81 is the nucleotide sequence of the WoodsCRW variant L434-Leu-C435, comprising one inserted leucine residue.

SEQ ID NO: 82 is the nucleotide sequence of the WoodsCRW variant C435-Leu-Y436, comprising one inserted leucine residue.

SEQ ID NO: 83 is the nucleotide sequence of the Plu1415-Woods chimera.

SEQ ID NO: 84 is the nucleotide sequence of the Woods-Plu1415 chimera.

SEQ ID NO: 85 is the amino acid sequence of the Plu1415 protein.

SEQ ID NO: 86 is the amino acid sequence of the WoodsCRW variant D397-Leu-Leu-C398, comprising two inserted leucine residues.

SEQ ID NO: 87 is the amino acid sequence of the WoodsCRW variant C398-Leu-Leu-V399, comprising two inserted leucine residues.

SEQ ID NO: 88 is the amino acid sequence of the WoodsCRW variant D397-Leu-C398-Leu, comprising two inserted leucine residues.

SEQ ID NO: 89 is the amino acid sequence of the WoodsCRW variant Y436F.

SEQ ID NO: 90 is the amino acid sequence of the WoodsCRW variant D397-Leu-C398, comprising one inserted leucine residue.

SEQ ID NO: 91 is the amino acid sequence of the WoodsCRW variant C398-Leu-V399, comprising one inserted leucine residue.

SEQ ID NO: 92 is the amino acid sequence of the WoodsCRW variant L382-Leu-C383, comprising one inserted leucine residue.

SEQ ID NO: 93 is the amino acid sequence of the WoodsCRW variant C383-Leu-Y384, comprising one inserted leucine residue.

SEQ ID NO: 94 is the amino acid sequence of the WoodsCRW variant L434-Leu-C435, comprising one inserted leucine residue.

SEQ ID NO: 95 is the amino acid sequence of the WoodsCRW variant C435-Leu-Y436, comprising one inserted leucine residue.

SEQ ID NO: 96 is the amino acid sequence of the Plu1415-Woods chimera.

SEQ ID NO: 97 is the amino acid sequence of the Woods-Plu1415 chimera.

SEQ ID NO: 98 is the amino acid sequence of the Plu1415 protein.

SEQ ID NO: 99 is the nucleotide sequence of the C-terminal β-prism domain of WoodsCRW (amino acids 347-490).

SEQ ID NO: 100 is the amino acid sequence of the C-terminal β-prism domain of WoodsCRW (amino acids 347-490).

Definitions

For clarity, certain terms used in the specification are defined and presented as follows:

"Activity" of the insecticidal proteins of the invention is meant that the insecticidal proteins function as orally active insect control agents, have a toxic effect, and/or are able to disrupt or deter insect feeding, which may or may not cause death of the insect. When an insecticidal protein of the invention is delivered to the insect, the result is typically death of the insect, or the insect does not feed upon the source that makes the insecticidal protein available to the insect. "Pesticidal" is defined as a toxic biological activity capable of controlling a pest, such as an insect, nematode, fungus, bacteria, or virus, preferably by killing or destroying them. "Insecticidal" is defined as a toxic biological activity capable of controlling insects, preferably by killing them. A "pesticidal agent" is an agent that has pesticidal activity. An "insecticidal agent" is an agent that has insecticidal activity.

"Associated with/operatively linked" refer to two nucleic acids that are related physically or functionally. For example, a promoter or regulatory DNA sequence is said to be "associated with" a DNA sequence that codes for RNA or a protein if the two sequences are operatively linked, or situated such that the regulatory DNA sequence will affect the expression level of the coding or structural DNA sequence.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" an insecticidal protein means that the insecticidal protein comes in contact with an insect, resulting in a toxic effect and control of the insect. The insecticidal protein may be delivered in many recognized ways, e.g., through a transgenic plant expressing the insecticidal protein, formulated protein composition(s), sprayable protein composition(s), a bait matrix, or any other art-recognized toxin delivery system.

"Effective insect-controlling amount" means that concentration of an insecticidal protein that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used. Any available terminator known to function in plants can be used in the context of this invention.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

A "gene" is a defined region that is located within a genome and comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any nucleic acid molecule which, when transferred to a plant, confers upon the plant a desired trait such as antibiotic resistance, virus resistance, insect resistance, disease resistance, or resistance to other pests, herbicide tolerance, abiotic stress tolerance, male sterility, modified fatty acid metabolism, modified carbohydrate metabolism, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence or nucleic acid molecule is a nucleic acid sequence or nucleic acid molecule not naturally associated with a host cell into which it is introduced, including non-naturally occurring multiple copies of a naturally occurring nucleic acid sequence. A heterologous nucleic acid sequence or nucleic acid molecule may comprise a chimeric sequence such as a chimeric expression cassette, where the promoter and the coding region are derived from multiple source organisms. The promoter sequence may be a constitutive promoter sequence, a tissue-specific promoter sequence, a chemically-inducible promoter sequence, a wound-inducible promoter sequence, a stress-inducible promoter sequence, or a developmental stage-specific promoter sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Identity" or "percent identity" refers to the degree of similarity between two nucleic acid or protein sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or at least about 85%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic* Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A further indication that two nucleic acids or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated toxin is a nucleic acid molecule or toxin that, by the hand of man, exists apart from its native environment and is therefore not a product of nature. An isolated nucleic acid molecule or toxin may exist in a purified form or may exist in a non-native environment such as, for example without limitation, a recombinant microbial cell, plant cell, plant tissue, or plant.

A "nucleic acid molecule" or "nucleic acid sequence" is a segment of single- or double-stranded DNA or RNA that can be isolated from any source. In the context of the present invention, the nucleic acid molecule is typically a segment of DNA. In some embodiments, the nucleic acid molecules of the invention are isolated nucleic acid molecules.

The terms "protein," "peptide" and "polypeptide" are used interchangeably herein.

As used herein, "codon optimized" sequence means the nucleotide sequence of a recombinant, transgenic, or synthetic polynucleotide wherein the codons are chosen to reflect the particular codon bias that a host cell may have. This is done in such a way so as to preserve the amino acid sequence of the polypeptide encoded by the codon optimized polynucleotide. In certain embodiments, the nucleotide sequence of the recombinant DNA construct includes a sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase and initiates transcription of the DNA. The promoter region may also include other elements that act as regulators of gene expression.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Transformation" is a process for introducing heterologous nucleic acid into a host cell or organism. In particular embodiments, "transformation" means the stable integration of a DNA molecule into the genome (nuclear or plastid) of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G) Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; l), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DETAILED DESCRIPTION

This invention relates to novel insecticidal proteins which have activity against coleopterans, for example, *Diabrotica virgifera virgifera* (western corn rootworm; WCR), *Diabrotica barberi* (northern corn rootworm; NCR), and/or *Diabrotica undecimpunctata howardi* (southern corn rootworm; SCR) and/or other *Diabrotica* species including *Diabrotica virgifera zeae* (Mexican corn rootworm), and/or Colorado Potato Beetle. In embodiments, a novel insecticidal protein of the invention may have activity against Lepidopteran species. The present invention also relates to nucleic acids whose expression results in insecticidal proteins of the invention, and to the making and using of the insecticidal proteins to control insect pests. In embodiments, the expression of the nucleic acids results in insecticidal proteins that can be used to control coleopteran insects such as western, northern and/or southern corn rootworm, particularly when expressed in a transgenic plant such as a transgenic corn plant.

The present invention further encompasses a nucleic acid molecule comprising a nucleotide sequence that encodes an insecticidal protein of the invention. The nucleotide sequence may be optimized for expression in bacteria, such as *Escherichia coli*, or for expression in a plant, such as *Zea mays*. A nucleotide sequence optimized for expression in a heterologous organism, such as a species of bacteria different from where it originated or a plant, is not naturally occurring. In one aspect of this embodiment, the nucleic acid molecule comprises the nucleotide sequence of SEQ ID NO: 2, SEQ ID NO: 4 to 36, SEQ ID NO: 73 to 83, and/or SEQ ID NO: 99. Specifically exemplified teachings of methods to make nucleic acid molecules that encode the insecticidal proteins of the invention can be found in the examples of the present application. Those skilled in the art will recognize that modifications can be made to the exemplified methods to make the insecticidal proteins encompassed by the present invention.

A skilled person would recognize that a transgene for commercial use, such as a nucleic acid molecule that comprises any one of SEQ ID NO: 2 to 36, SEQ ID NO: 73 to 83, or SEQ ID NO: 99 may have relatively minor modifications to the nucleic acid sequence to comply with governmental regulatory standards. Such modifications would not affect the function of the resulting molecule, which would be substantially identical to SEQ ID NO: 2 to 36, SEQ ID NO: 73 to 83, and/or SEQ ID NO: 99. A skilled person would recognize that the modified nucleic acid molecule would be essentially the same as the starting molecule, and is encompassed by the present invention.

The present invention also encompasses a nucleic acid molecule that comprises (a) a nucleotide sequence of any one of SEQ ID NO: 2 to 36, SEQ ID NO: 73 to 83, or SEQ ID NO: 99; (b) a nucleotide sequence that is sequence at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to any one of the nucleotide sequences of SEQ ID NO: 2 to 36, SEQ ID NO: 73 to 83, or SEQ ID NO: 99; (c) a nucleotide sequence that encodes a polypeptide, wherein the amino acid sequence of the polypeptide comprises SEQ ID NO: 1, SEQ ID NO: 37 to 69, or SEQ ID NO: 86-96, and has insect control activity; (d) a nucleotide sequence that encodes a polypeptide, wherein the amino acid sequence of the polypeptide is at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to any one of the amino acid sequences of SEQ ID NO: 1, SEQ ID NO: 37 to 72, SEQ ID NO: 86 to 96, or SEQ ID NO: 100; or (e) a nucleotide sequence that is complementary to the nucleotide sequence of any one of (a) to (d) above.

The present invention further encompasses an expression cassette comprising a promoter operably linked to a heterologous nucleotide sequence that comprises: (a) a nucleotide sequence of any one of SEQ ID NOs: 2 to 36, SEQ ID NO: 73 to 83, or SEQ ID NO: 99; (b) a nucleotide sequence that is at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of any one of SEQ ID NOs: 2 to 36, SEQ ID NO: 73 to 83, or SEQ ID NO: 99; (c) a nucleotide sequence that encodes a polypeptide, wherein the amino acid sequence of the polypeptide comprises SEQ ID NO: 1, SEQ ID NO: 37 to 72, SEQ ID NO: 86 to 96, or SEQ ID NO: 100, and has insect control activity; (d) a nucleotide sequence that encodes a polypeptide, wherein the amino acid sequence of the polypeptide is at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the amino acid sequence of any one of SEQ ID NO: 1, SEQ ID NO: 37 to 72, SEQ ID NO: 86 to 96, or SEQ ID NO: 100; or (e) a nucleotide sequence that is complementary to the nucleotide sequence of any one of (a) to (d) above. In some embodiments, the present invention encompasses an expression cassette comprising a heterologous nucleic acid molecule comprising a nucleotide sequence that encodes a polypeptide, wherein the amino acid sequence of the polypeptide is at least 93% identical to the amino acid sequence of SEQ ID NO: 55, SEQ ID NO: 67, or SEQ ID NO: 86 to 91. The expression cassette comprises a promoter operably linked to a heterologous nucleotide sequence and is not naturally occurring.

In some embodiments, the heterologous nucleic acid molecule of the expression cassette comprises a nucleotide sequence that encodes a polypeptide, wherein the amino acid sequence of the polypeptide is the amino acid sequence of SEQ ID NO: 72 and wherein the "X" amino acid residue can be any amino acid residue. In some embodiments, the heterologous nucleic acid molecule of the expression cassette comprises a nucleotide sequence that encodes a polypeptide at least 93% identical to the amino acid sequence of SEQ ID NO: 100.

The present invention also encompasses recombinant vectors or constructs, which may also be referred to as vectors or constructs, comprising the expression cassettes and/or the nucleic acid molecules of this invention. In such vectors, the nucleic acids are preferably in expression cassettes comprising regulatory elements for expression of the nucleotide molecules in a host cell capable of expressing the nucleotide molecules. Such regulatory elements usually comprise promoter and termination signals and preferably also comprise elements allowing efficient translation of polypeptides encoded by the nucleic acids of the present invention. Vectors comprising the nucleic acids are may be capable of replication in particular host cells, preferably as extrachromosomal molecules, and are therefore used to amplify the nucleic acids of this invention in the host cells. The present invention also encompasses a host cell that contains an expression cassette or a nucleic acid molecule of the invention. In one embodiment, host cells for such vectors are microorganisms, such as bacteria, in particular *Bacillus thuringiensis* or *E. coli*, or such as fungi such as yeast. In another embodiment, host cells for such recombinant vectors are endophytes or epiphytes. In yet another embodiment, such vectors are viral vectors and are used for replication of the nucleotide sequences in particular host cells, e.g. insect cells or plant cells. Recombinant vectors are also used for transformation of the nucleotide molecules of this invention into host cells, whereby the nucleotide molecules are stably integrated into the DNA of a transgenic host. In one embodiment, the transgenic host is plant, for example a monocot plant, such as a corn plant or a wheat plant. In embodiments, the transgenic host plant is a dicot plant, such as a soybean plant or cotton plant.

In another embodiment, at least one of the nucleic acids of the invention is inserted into an appropriate expression cassette, comprising a promoter and termination signal. Expression of the nucleic acid may be constitutive, or an inducible promoter responding to various types of stimuli to initiate transcription may be used. In another embodiment, the cell in which the insecticidal protein of the invention is expressed is a microorganism, such as a virus, bacteria, or a fungus. In yet another embodiment, a virus, such as a baculovirus, contains a nucleic acid of the invention in its genome and expresses large amounts of the corresponding insecticidal protein after infection of appropriate eukaryotic cells that are suitable for virus replication and expression of the nucleic acid. The insecticidal protein thus produced is used as an insecticidal agent. Alternatively, baculoviruses engineered to include the nucleic acid are used to infect insects in vivo and kill them either by expression of the insecticidal toxin or by a combination of viral infection and expression of the insecticidal toxin. In a further embodiment, the present invention also encompasses a method for producing a polypeptide with insecticidal activity, comprising culturing the host cell under conditions in which the nucleic acid molecule encoding the polypeptide is expressed.

Bacterial cells are also hosts for the expression of the nucleic acids of the invention. In one embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleic acids for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In: Industrial Microorganisms: Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In: Industrial microorganisms: basic and applied molecular genetics, Baltz, Hegeman, and Skatrud eds., American Society for Microbiology, Washington (1993); Dequin & Bane, Biotechnology L2:173-177 (1994); van den Berg et al., Biotechnology 8:135-139 (1990)).

Certain insecticidal proteins have been expressed in plants and seed from such plants are sold annually to farmers for use in controlling various insect pests. Such self-protected insecticidal products are subject to review and registration by various regulatory agencies including, for example, the US Environmental Protection Agency (EPA).

Dietary exposure is the major route by which humans can be exposed to insecticidal proteins expressed in transgenic plants. Acute oral mammalian toxicity and protein digestibility are the end points for EPA's human health risk assessment. Further scientific evidence of the safety of insecticidal proteins is that they have been shown to be rapidly degraded in vitro using simulated gastric fluids. For example, results of seven in vitro assays conducted with representative Cry1, Cry2, and Cry3 proteins establish that the proteins are rapidly degraded, typically within 30 seconds. These results support the broader conclusion that members of these groups of Cry proteins (that share significant amino acid sequence identity) are likely to be rapidly degraded following ingestion by humans. Similar tests are done for each transgenic protein expressed in plants. Another area of consideration is whether insecticidal proteins may induce an allergenic reaction. Demonstrated rapid in vitro degradation of the transgenic insecticidal protein should minimize the potential for such an occurrence. By comparison, food allergens generally persist in the in vitro gastrointestinal model, whereas common food proteins with no allergenic history degraded rapidly in simulated gastric fluid (Metcalfe et al. 1996).

A simulated gastric fluid (SGF) assay measures the in vitro digestibility of a test protein at tightly controlled conditions representative of the upper mammalian digestive tract. For example, bacterially produced test Cry protein (at a concentration of 0.5-5 mg/ml) was exposed to the enzyme pepsin (from porcine gastric mucosa, solubilized in 2 mg/ml NaCl, pH 1.2) at a ratio of 10 Units of pepsin activity/µg test protein over a time period of one hour at 37° C. Samples are removed at 1, 2, 5, 10, 30, and 60 minute timepoints and immediately quenched with the addition of pre-heated (95° C. —2 minutes) stop buffer (65% 0.5M Sodium Bicarbonate pH 11, 35% Tricine Loading Buffer) to immediately render pepsin inactive, and returned to heat for an additional 5 minutes. Once the assay was complete, time point samples and controls (test protein alone, pepsin alone) were examined by SDS-PAGE on a 10-20% Tris-Tricine gel (with peptides visible down to 1 kDa) to track the kinetics and level of digestion performed by pepsin. If the test protein or a significant polypeptide fragment of the text protein is visible at, for example, the 5 and/or 10 minute timepoints, then it is not digestible or not completely digestible by the SGF assay, and may be scored qualitatively as "no", or "not digestible". If the test protein and any significant polypeptide fragment is not visible at, for example, the 5 minute timepoint, then it is digestible by the SGF assay, and may be scored qualitatively as "yes" or "digestible".

The present invention also encompasses a polypeptide comprising an amino acid sequence at least 45% identical, at least 50% identical, at least 55%, at least 60%, at least 65%, at least 70%, at least 75%, at least 80%, at least 85%, at least 90%, at least 92%, at least 95%, at least 98%, at least 99% identical, or is 100% identical to any one of SEQ ID NO: 1, SEQ ID NO: 37 to 72, SEQ ID NO: 86 to 96, or SEQ ID NO: 100, and further comprising an introduced protease cleavage site. The introduced protease cleavage site is not naturally occurring, and is introduced into the polypeptide sequence, as a substitution mutation or as an insertion or deletion mutation. The introduced protease cleavage site may be introduced by the insertion of at least one leucine residue in a polypeptide sequence comprising any one of SEQ ID NO: 1, SEQ ID NO: 37 to 72, SEQ ID NO: 86 to 96, or SEQ ID NO: 100. The introduced mutation may destabilize the polypeptide, so that a protease may gain access to a cleavage site which it previously did not have access to due to tight and/or stable folding of the protein, or to steric hindrance. The introduced protease cleavage site may be an introduced mutation in the polypeptide sequence which is recognized by a protease, such as chymotrypsin, trypsin, or pepsin, as a site for proteolytic cleavage. In some embodiments, the introduced protease cleavage site may alter an existing protease cleavage site so that it is recognized by a different protease. Protease cleavage sites for chymotrypsin, trypsin, and pepsin are well-known in the art. Chymotrypsin preferentially cleaves peptide amide bonds where the carboxyl side of the amide bond (the P1 position) is a large hydrophobic amino acid (tyrosine, tryptophan, and phenylalanine). Trypsin cleaves peptide chains mainly at the carboxyl side of the amino acids lysine or arginine, except when either is followed by proline. Pepsin is most efficient in cleaving peptide bonds between hydrophobic and preferably aromatic amino acids such as phenylalanine, tryptophan, and tyrosine. These cleavage sites are the preferential cleavage sites and do not include all cleavage sites recognized by chymotrypsin, trypsin, or pepsin, and furthermore do not include all cleavage sites for all proteases.

An example of a polypeptide engineered to contain an introduced protease cleavage site is WoodsCRW variant C398L (SEQ ID NO: 55). This substitution mutation changes a motif from "NKDCVS" to "NKDLVS". This introduced protease cleavage site may be recognized by pepsin and/or chymotrypsin, and is not present in the wild type WoodsCRW protein sequence. In some embodiments, the introduced protease cleavage site may be at or near the site of the mutation, for example residues 388-408 of the polypeptide. It is well-known in the art that cysteines in proteins are frequently covalently bonded to other cysteine residues to form disulfide bonds. Disulfide bonds play an important role in the folding and stability of some proteins. Therefore, the WoodsCRW variant C398L may have an altered or less stable tertiary structure compared to wild-type WoodsCRW. In some embodiments, the introduced protease cleavage site may be located distal from the introduced mutation. For example, the introduced mutation of C398L may "loosen" the three dimensional folding of the WoodsCRW polypeptide, thereby making a protease cleavage site that was previously inaccessible (and therefore not cleaved) accessible to a protease. This results in the introduced mutation introducing a protease cleavage site that did not exist in the unaltered polypeptide. In some embodiments, the introduced mutation and/or the introduced protease cleavage site is located between amino acid residues 1 to 490 of any one of SEQ ID NOs: 1, SEQ ID NO: 37 to 69, SEQ ID NO: 72, or SEQ ID NO: 86 to 96. In further embodiments, the introduced mutation and/or the introduced protease cleavage site is located between amino acid residues 100 to 490 of any one of SEQ ID NOs: 1, SEQ ID NO: 37 to 69, SEQ ID NO: 72, or SEQ ID NO: 86 to 96. In further embodiments, the introduced mutation and/or the introduced protease cleavage site is located between amino acid residues 190 to 490 of any one of SEQ ID NOs: 1, SEQ ID NO: 37 to 69, SEQ ID NO: 72, or SEQ ID NO: 86 to 96. In further embodiments, the introduced mutation and/or the introduced protease cleavage site is located between amino acid residues 190 to 310 of any one of SEQ ID NOs: 1, SEQ ID NO: 37 to 69, SEQ ID NO: 72, or SEQ ID NO: 86 to 96. In further embodiments, the introduced mutation and/or the introduced protease cleavage site is located between amino acid residues 190 to 210 of any one of SEQ ID NOs: 1, SEQ ID NO: 37 to 69, SEQ ID NO: 72, or SEQ ID NO: 86 to 96. In other embodiments, the introduced mutation is located between amino acid residues 300 to 490 of any one of SEQ ID NOs: 1, SEQ ID NO: 37 to 69, SEQ ID NO: 72, or SEQ ID NO: 86 to 96. In further embodiments, the introduced mutation and/or the introduced protease cleavage site is located between amino acid residues 300 to 400 of any one of SEQ ID NOs: 1, SEQ ID NO: 37 to 69, SEQ ID NO: 72, or SEQ ID NO: 86 to 96.

The introduced protease cleavage site may alter protease specificity at that site, for example, it may change a trypsin proteolytic cleavage site to a chymotrypsin proteolytic cleavage site. For example, WoodsCRW variant K406L (SEQ ID NO: 45) may change a trypsin cleavage site to a chymotrypsin or a pepsin cleavage site. In some embodiments, the introduced protease cleavage site is located between amino acid residues 1 to 490 of any one of SEQ ID NOs: 1, SEQ ID NO: 37 to 69, SEQ ID NO: 72, or SEQ ID NO: 86 to 96. In further embodiments, the introduced protease cleavage site is located between amino acid residues 100 to 490 of any one of SEQ ID NOs: 1, SEQ ID NO: 37 to 69, SEQ ID NO: 72, or SEQ ID NO: 86 to 96. In further embodiments, the introduced protease cleavage site is located between amino acid residues 190 to 490 of any one of SEQ ID NOs: 1, SEQ ID NO: 37 to 69, SEQ ID NO: 72, or SEQ ID NO: 86 to 96. In further embodiments, the introduced protease cleavage site is located between amino acid residues 190 to 400 of any one of SEQ ID NOs: 1, SEQ ID NO: 37 to 69, SEQ ID NO: 72, or SEQ ID NO: 86 to 96. In further embodiments, the introduced protease cleavage site is located between amino acid residues 190 to 310 of any one of SEQ ID NOs: 1, SEQ ID NO: 37 to 69, SEQ ID NO: 72, or SEQ ID NO: 86 to 96. In further embodiments, the introduced protease cleavage site is located between amino acid residues 190 to 210 of any one of SEQ ID NOs: 1, SEQ ID NO: 37 to 69, SEQ ID NO: 72, or SEQ ID NO: 86 to 96. In other embodiments, the introduced protease cleavage site is located between amino acid residues 300 to 490 of any one of SEQ ID NOs: 1, SEQ ID NO: 37 to 69, SEQ ID NO: 72, or SEQ ID NO: 86 to 96. In further embodiments, the introduced protease cleavage site is located between amino acid residues 300 to 400 of any one of SEQ ID NOs: 1, SEQ ID NO: 37 to 69, SEQ ID NO: 72, or SEQ ID NO: 86 to 96. In a further embodiment, the introduced protease cleavage site which alters protease specificity may be located between corresponding amino acid residues of 313 to 490 of any one of SEQ ID NOs: 1, SEQ ID NO: 37 to 69, or SEQ ID NO: 86 to 96.

The present invention also encompasses a polypeptide comprising an amino acid sequence at least 45% identical, at least 50% identical, at least 55%, at least 60%, at least 65%, at least 70%, at least 75%, at least 80%, at least 85%, at least 90%, at least 92%, at least 95%, at least 98%, at least 99% identical, or is 100% identical to any one of SEQ ID NOs: 1, SEQ ID NO: 37 to 69, or SEQ ID NO: 86 to 96, and further comprising an introduced mutation which improves digestibility in an SGF assay compared to a polypeptide comprising the amino acid sequence of SEQ ID NO: 1. The mutation may be a substitution mutation, insertion, or deletion. The mutation may be the insertion of at least one leucine residue.

The present invention also includes a method of improving digestibility of a polypeptide at least 45% identical, at least 50% identical, at least 55%, at least 60%, at least 65%, at least 70%, at least 75%, at least 80%, at least 85%, at least 90%, at least 92%, at least 95%, at least 98%, at least 99% identical, or is 100% identical to any one of SEQ ID NOs: 1, SEQ ID NO: 37 to 69, or SEQ ID NO: 86 to 96 comprising introducing at least one mutation into the amino acid sequence of the polypeptide. In embodiments, this introduced mutation improves the digestibility of the polypeptide in an SGF assay. The mutation may improve digestibility by introducing a protease cleavage site. In other embodiments, the mutation may improve digestibility by altering protease specificity at that site. For example, so that what may have been a chymotrypsin or trypsin site is mutated to a pepsin site. In other embodiments, the mutation may destabilize the protein so that a site is made accessible to a protease for cleavage. The site made accessible to a protease may be distal from the introduced mutation. In preferred embodiments, the mutation does not alter or does not significantly alter the activity, or the insecticidal activity, of the polypeptide. In some embodiments, the polypeptide with the introduced mutation possesses at least 50%, at least 55%, at least 60%, at least 65%, at least 70%, at least 75%, at least 80%, at least 85%, at least 90%, at least 92%, at least 93%, at least 94%, at least 95%, at least 96%, at least 97%, at least 98%, or at least 99% of the insecticidal activity of WoodsCRW. This method is exemplified in the examples of the present specification, where, for example, the WoodsCRW variants C398L, C398Y, and D397-Leu-Leu-C398 were found to have improved digestibility in the SGF assay. They also retained very high insecticidal activity.

In some embodiments of the method described above, the introduced mutation(s) may be located between amino acid residues 1 to 490 of any one of SEQ ID NOs: 1, SEQ ID NO: 37 to 69, SEQ ID NO: 72, or SEQ ID NO: 86 to 96. In further embodiments, the introduced mutation(s) may be located between amino acid residues 100 to 490 of any one of SEQ ID NOs: 1, SEQ ID NO: 37 to 69, SEQ ID NO: 72, or SEQ ID NO: 86 to 96. In further embodiments, the introduced mutation(s) may be located between amino acid residues 190 to 490 of any one of SEQ ID NOs: 1, SEQ ID NO: 37 to 69, SEQ ID NO: 72, or SEQ ID NO: 86 to 96. In further embodiments, the introduced mutation(s) may be located between amino acid residues 190 to 400 of any one of SEQ ID NOs: 1, SEQ ID NO: 37 to 69, SEQ ID NO: 72, or SEQ ID NO: 86 to 96. In further embodiments, the introduced mutation(s) may be located between amino acid residues 190 to 310 of any one of SEQ ID NOs: 1, SEQ ID NO: 37 to 69, SEQ ID NO: 72, or SEQ ID NO: 86 to 96. In further embodiments, the introduced mutation(s) may be located between amino acid residues 190 to 210 of any one of SEQ ID NOs: 1, SEQ ID NO: 37 to 69, SEQ ID NO: 72, or SEQ ID NO: 86 to 96. In other embodiments, the introduced mutation(s) may be located between amino acid residues 300 to 490 of any one of SEQ ID NOs: 1, SEQ ID NO: 37 to 69, SEQ ID NO: 72, or SEQ ID NO: 86 to 96. In further embodiments, introduced mutation(s) may be located between amino acid residues 300 to 400 of any one of SEQ ID NOs: 1, SEQ ID NO: 37 to 69, SEQ ID NO: 72, or SEQ ID NO: 86 to 96. In a further embodiment, the introduced mutation(s) may be located between corresponding amino acid residues of 313 to 490 of any one of SEQ ID NOs: 1 or SEQ ID NO: 37 to 69. In other embodiments, the mutation(s) may be introduced between amino acid sequences 313 to 490 of SEQ ID NO: 1.

In other embodiments, a mutation may be introduced at or proximal to C398 of SEQ ID NO: 1. In further embodiments, the mutation may be C398L, C398I, C398V, C398G, C398A, C398F, C398M, C398S, C398W, or C398Y. In other embodiments, the mutation may be the insertion or deletion of an amino acid residue, such as for example, the insertion of at least one leucine residue. This residue(s) may be adjacent to, or neighboring, C398 of SEQ ID NO: 1, such as for example WoodsCRW variants D397-Leu-C398, D397-Leu-Leu-C398, C398-Leu-V399, C398-Leu-Leu-V399, or D397-Leu-C398-L, which are all found to have improved digestibility in the SGF assay. They also retained very high insecticidal activity (see Examples). Leucine residues may also be inserted proximal to C398, wherein "proximal" may be at least 1, at least 2, at least 4, at least 6, at least 8, at least 10, or at least 20 amino acids away from C398.

The insecticidal proteins of the present invention have insect control activity when tested against insect pests in bioassays. In one embodiment, the insecticidal proteins of the invention are active against coleopteran and/or lepidopteran insects. A person skilled in the art will appreciate that a protein of the present invention may have a different range of insecticidal activity compared to other proteins of the invention. In some embodiments, a WoodsCRW mutant variant may have insecticidal activity on a broader range of insect pests, such as more coleopteran or lepidopteran species, compared to other variants of WoodsCRW. In other embodiments, a variant of WoodsCRW may have insecticidal activity on lepidopteran species but not on coleopteran species. In some embodiments, a variant of WoodsCRW may have activity on a broader range of insecticidal activity on coleopteran or lepidopteran species compared to unmodified WoodsCRW (SEQ ID NO: 1).

Insects in the order Lepidoptera include without limitation any insect now known or later identified that is classified as a lepidopteran, including those insect species within suborders Zeugloptera, Glossata, and Heterobathmiina, and any combination thereof. Exemplary lepidopteran insects include, but are not limited to, *Ostrinia* spp. such as *O. nubilalis* (European corn borer); *Plutella* spp. such as *P. xylostella* (diamondback moth); *Spodoptera* spp. such as *S. frugiperda* (fall armyworm), *S. ornithogalli* (yellowstriped armyworm), *S. praefica* (western yellowstriped armyworm), *S. eridania* (southern armyworm) and *S. exigua* (beet armyworm); *Agrotis* spp. such as *A. ipsilon* (black cutworm), *A. segetum* (common cutworm), *A. gladiaria* (claybacked cutworm), and *A. orthogonia* (pale western cutworm); *Striacosta* spp. such as *S. albicosta* (western bean cutworm); *Helicoverpa* spp. such as *H. zea* (corn earworm), *H. punctigera* (native budworm), *S. littoralis* (Egyptian cotton leafworm) and *H. armigera* (cotton bollworm); *Heliothis* spp. such as *H. virescens* (tobacco budworm); *Diatraea* spp. such as *D. grandiosella* (southwestern corn borer) and *D. saccharalis* (sugarcane borer); *Trichoplusia* spp. such as *T. ni* (cabbage looper); *Sesamia* spp. such as *S. nonagroides* (Mediterranean corn borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Crymodes* spp. such as *C. devastator* (glassy cutworm); *Feltia* spp. such as *F. ducens* (dingy cutworm); and any combination of the foregoing. In one aspect of this embodiment, the insecticidal proteins of the invention are active against black cutworm, sugar cane borer, and/or southwestern corn borer.

Insects in the order Coleoptera include but are not limited to any coleopteran insect now known or later identified including those in suborders Archostemata, Myxophaga, Adephaga and Polyphaga, and any combination thereof.

In one aspect of this embodiment, the insecticidal proteins of the invention are active against *Diabrotica* spp. *Diabrotica* is a genus of beetles of the order Coleoptera commonly referred to as "corn rootworms" or "cucumber beetles." Exemplary *Diabrotica* species include without limitation *Diabrotica barberi* (northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm), *D. beniensis, D. cristata, D. curviplustalata, D. dissimilis, D. elegantula, D. emorsitans, D. graminea, D. hispanloe, D. lemniscata, D. linsleyi, D. milleri, D. nummularis, D. occlusal, D. porrecea, D. scutellata, D. tibialis, D. trifasciata* and *D. viridula*; and any combination thereof.

Other nonlimiting examples of Coleopteran insect pests according to the present invention include *Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing.

The insecticidal proteins of the invention may also be active against Hemipteran, Dipteran, *Lygus* spp., and/or other piercing and sucking insects, for example of the order Orthoptera or Thysanoptera. Insects in the order Diptera include but are not limited to any dipteran insect now known or later identified including but not limited to *Liriomyza* spp. such as *L. trifolii* (leafminer) and *L. sativae* (vegetable leafminer); *Scrobipalpula* spp. such as *S. absoluta* (tomato leafminer); *Delia* spp. such as *D. platura* (seedcorn maggot), *D. brassicae* (cabbage maggot) and *D. radicum* (cabbage root fly); *Psilia* spp. such as *P. rosae* (carrot rust fly); *Tetanops* spp. such as *T. myopaeformis* (sugarbeet root maggot); and any combination of the foregoing.

Insects in the order Orthoptera include but are not limited to any orthopteran insect now known or later identified including but not limited to *Melanoplus* spp. such as *M. differentialis* (Differential grasshopper), *M. femurrubrum* (Redlegged grasshopper), *M. bivittatus* (Twostriped grasshopper); and any combination thereof.

Insects in the order Thysanoptera include but are not limited to any thysanopteran insect now known or later identified including but not limited to *Frankliniella* spp. such as *F. occidentalis* (western flower thrips) and *F. fusca* (tobacco thrips); and *Thrips* spp. such as *T. tabaci* (onion thrips), *T. palmi* (melon thrips); and any combination of the foregoing.

The insecticidal proteins of the invention may also be active against nematodes. The term "nematode" as used herein encompasses any organism that is now known or later identified that is classified in the animal kingdom, phylum Nematoda, including without limitation nematodes within class Adenophorea (including for example, orders Enoplida, Isolaimida, Mononchida, Dorylaimida, Trichocephalida, Mermithida, Muspiceida, Araeolaimida, Chromadorida, Desmoscolecida, Desmodorida and Monhysterida) and/or class Secernentea (including, for example, orders Rhabdita, Strongylida, Ascaridida, Spirurida, Camallanida, Diplogasterida, Tylenchida and Aphelenchida).

Nematodes include but are not limited to parasitic nematodes such as root-knot nematodes, cyst nematodes and/or lesion nematodes. Exemplary genera of nematodes according to the present invention include but are not limited to, *Meloidogyne* (root-knot nematodes), *Heterodera* (cyst nematodes), *Globodera* (cyst nematodes), *Radopholus* (burrowing nematodes), *Rotylenchulus* (reniform nematodes), *Pratylenchus* (lesion nematodes), *Aphelenchoides* (foliar nematodes), *Helicotylenchus* (spiral nematodes), *Hoplolaimus* (lance nematodes), *Paratrichodorus* (stubby-root nematodes), *Longidorus, Nacobbus* (false root-knot nematodes), *Subanguina, Belonlaimus* (sting nematodes), *Criconemella, Criconemoides* (ring nematodes), *Ditylenchus, Dolichodorus, Hemicriconemoides, Hemicycliophora, Hirschmaniella, Hypsoperine, Macroposthonia, Melinius, Punctodera, Quinisulcius, Scutellonema, Xiphinema* (dagger nematodes), *Tylenchorhynchus* (stunt nematodes), *Tylenchulus, Bursaphelenchus* (round worms), and any combination thereof.

Exemplary plant parasitic nematodes according to the present invention include, but are not limited to, *Belonolaimus gracilis, Belonolaimus longicaudatus, Bursaphelenchus xylophilus* (pine wood nematode), *Criconemoides ornata, Ditylenchus destructor* (potato rot nematode), *Ditylenchus dipsaci* (stem and bulb nematode), *Globodera pallida* (potato cyst nematode), *Globodera rostochiensis* (golden nematode), *Heterodera glycines* (soybean cyst nematode), *Heterodera schachtii* (sugar beet cyst nematode); *Heterodera zeae* (corn cyst nematode), *Heterodera avenae* (cereal cyst nematode), *Heterodera carotae, Heterodera trifolii, Hoplolaimus columbus, Hoplolaimus galeatus, Hoplolaimus magnistylus, Longidorus breviannulatus, Meloidogyne arenaria, Meloidogyne chitwoodi, Meloidogyne hapla, Meloidogyne incognita, Meloidogyne javanica, Mesocriconema xenoplax, Nacobbus aberrans, Naccobus dorsalis, Paratrichodorus christiei, Paratrichodorus minor, Pratylenchus brachyurus, Pratylenchus crenatus, Pratylenchus hexincisus, Pratylenchus neglectus, Pratylenchus penetrans, Pratylenchus projectus, Pratylenchus scribneri, Pratylenchus tenuicaudatus, Pratylenchus thornei, Pratylenchus zeae, Punctodera chaccoensis, Quinisulcius acutus, Radopholus similis, Rotylenchulus reniformis, Tylenchorhynchus dubius, Tylenchulus semipenetrans* (citrus nematode), *Siphinema americanum, X. Mediterraneum*, and any combination of the foregoing.

In another embodiment, the invention encompasses a method of producing a insecticidal protein that is active against insects, comprising: (a) obtaining a host cell comprising a gene, which itself comprises an expression cassette and/or a nucleic acid molecule of the invention; and (b) growing the transgenic host cell in such a manner to express an insecticidal protein that is active against insects.

In yet a further embodiment, the invention encompasses a method of controlling insects, comprising delivering to the insects an effective insect-controlling amount of an insecticidal protein of the invention.

In one embodiment, at least one of the insecticidal proteins of the invention is expressed in a higher organism such as a plant. In this case, transgenic plants expressing effective insect-controlling amounts of the insecticidal protein protect themselves from insect pests. When the insect starts feeding on such a transgenic plant, it also ingests the expressed insecticidal protein. This will deter the insect from further biting into the plant tissue and/or may even harm or kill the insect. A nucleic acid of the present invention is inserted into an expression cassette, which may then be stably integrated in the genome of the plant. In another embodiment, the nucleic acid is included in a non-pathogenic self-replicating virus. Plants transformed in accordance with the present invention may be monocotyledonous or dicotyledonous and include, but are not limited to, corn, wheat, oat, turfgrass, pasture grass, flax, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, Arabidopsis, and woody plants such as coniferous and deciduous trees.

In another embodiment, the invention encompasses a method of producing a plant or plant part having enhanced insect resistance as compared to a control plant or plant part, comprising: (a) introducing a nucleic acid molecule comprising an expression cassette of the invention; and (b) growing the plant part into a plant that expresses the heterologous nucleic acid molecule of the expression cassette and that has enhanced insect resistance as compared to a control plant or plant part that has not been transformed with a nucleic acid molecule comprising the expression cassette. In a preferred embodiment, the expression cassette may encode a polypeptide comprising an amino acid sequence that is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical or similar to SEQ ID NO: 1, SEQ ID NO: 37 to 72, SEQ ID NO: 86 to 96, or SEQ ID NO: 100. In a preferred embodiment, the expression cassette may encode a polypeptide comprising an amino acid sequence that is at least 60% identical to SEQ ID NO: 4. "Enhanced" insect resistance may be measured as an increase in insecticidal activity. Enhanced insect resistance may be greater than 0%, at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 100%, at least 125%, at least 150%, at least 200%, at least 300%, at least 400%, at least 500%, at least 600%, at least 700%, at least 800%, at least 900%, or at least 1000% greater insecticidal activity compared to a control plant. A plant or plant part having enhance insect resistance as compared to a control plant or plant part may be produced by methods of plant transformation, plant tissue culture, or breeding. The plant or plant part may be produced by methods of sexual or asexual propagation. Any suitable control plant or plant part can be used, for example a plant of the same or similar genetic background grown in the same environment. In embodiments, the control plant or plant part is of the same genetic background and is growing in the same environment as the described plant, but it does not comprise a molecule of the invention, while the described plant does comprise a molecule of the invention.

In another embodiment, the invention encompasses a method of enhancing insect resistance in a plant or plant part as compared to a control plant or plant part, comprising expressing in the plant or plant part a nucleic acid molecule or an expression cassette of the invention, wherein expression of the heterologous nucleic acid of the expression cassette results in enhanced insect resistance in a plant or plant part as compared to a control plant or plant part. In embodiments, the expression cassette or nucleic acid molecule comprises a promoter operably linked to a heterologous nucleic acid molecule comprising a nucleotide sequence that comprises: (a) a nucleotide sequence of any one of SEQ ID NOs: 2 to 36, SEQ ID NO: 73 to 83, or SEQ ID NO: 99; (b) a nucleotide sequence that is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of any one of SEQ ID NOs: 2 to 36, SEQ ID NO: 73 to 83, or SEQ ID NO: 99; (c) a nucleotide sequence that encodes a polypeptide, wherein the amino acid sequence of the polypeptide comprises SEQ ID NO: 1, SEQ ID NO: 37 to 72, SEQ ID NO: 86 to 96, or SEQ ID NO: 100, and has insect control activity; (d) a nucleotide sequence that encodes a polypeptide, wherein the amino acid sequence of the polypeptide is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the amino acid sequence of SEQ ID NO: 1, SEQ ID NO: 37 to 72, SEQ ID NO: 86 to 96, or SEQ ID NO: 100; or (e) a nucleotide sequence that is complementary to the nucleotide sequence of any one of (a) to (d) above. The nucleic acid molecule or expression cassette may be introduced into the plant. In some embodiments, the nucleic acid molecule or expression cassette may be introduced into a plant part and a plant comprising the nucleic acid molecule or expression cassette may be produced from the plant part.

In another embodiment, the invention encompasses a method of producing a plant having enhanced insect resistance as compared to a control plant, comprising detecting, in a plant part, a heterologous nucleic acid comprising a nucleic acid molecule or an expression cassette of the invention and producing a plant from the plant part, thereby producing a plant having enhanced insect resistance as compared to a control plant. In a further embodiment, the invention encompasses a method of identifying a plant or plant part having enhanced insect resistance as compared to a control plant or plant part, comprising detecting, in the plant or plant part, a nucleic acid molecule or an expression cassette of the invention, thereby identifying a plant or plant part having enhanced insect resistance. In a further embodiment, the expression cassette or a diagnostic fragment thereof is detected in an amplification product from a nucleic acid sample from the plant or plant part. The diagnostic fragment may be a nucleic acid molecule at least 10 contiguous nucleotides long which is unique to the expression cassette of the invention.

In yet another embodiment, the invention encompasses a method of producing a plant having enhanced insect resistance as compared to a control plant or plant part, comprising crossing a first parent plant with a second parent plant, wherein at least the first parent plant comprises within its genome a heterologous nucleic acid that comprises a nucleic acid molecule or an expression cassette of the invention and producing a progeny generation, wherein the progeny generation comprises at least one plant that possesses the heterologous nucleic acid within its genome and that exhibits enhanced insect resistance as compared to a control plant.

In preferred embodiments, the methods of the invention confer enhanced insect resistance in a plant or plant part against a coleopteran and/or a lepidopteran insect pest. Insect control of both lepidopteran and coleopteran insect pests are demonstrated in the Examples. In further embodiments, the methods of the invention confer enhanced insect resistance in a plant or plant part against *Diabrotica* species, including *Diabrotica virgifera virgifera, Diabrotica barberi, Diabrotica undecimpunctata howardi, Diabrotica virgifera zeae,* and/or *Diabrotica speciosa,* and/or related species.

In preferred embodiments, the methods of the invention confer enhanced insect resistance in a monocotyledonous plant.

The present invention further encompasses a transgenic plant comprising a a heterologous nucleic acid molecule or an expression cassette of the invention, which when transcribed and translated confers enhanced insect resistance. In preferred embodiments, the heterologous nucleic acid molecule comprises a sequence at least 45%, at least 50%, at least 55%, at least 60%, at least 65%, at least 70%, at least 75%, at least 80%, at least 85%, at least 90%, at least 91% at least 92%, at least 93%, at least 94%, at least 95%, at least 96%, at least 97%, at least 98% at least 99%, or 100% identical to any one of SEQ ID NOs: 2 to 36, SEQ ID NO: 73 to 83, or SEQ ID NO: 99. In a further embodiment, the transgenic plant comprises a heterologous nucleic acid molecule comprising a sequence at least 45%, at least 50%, at least 55%, at least 60%, at least 65%, at least 70%, at least 75%, at least 80%, at least 85%, at least 90%, at least 91% at least 92%, at least 93%, at least 94%, at least 95%, at least 96%, at least 97%, at least 98% at least 99%, or 100% identical to SEQ ID NO: 2 to 36, SEQ ID NO: 73 to 83, or SEQ ID NO: 99. In embodiments, the transgenic plant is a dicotyledonous plant. In preferred embodiments, the transgenic plant is a monocotyledonous plant. In further embodiments, the transgenic plant is alfalfa, aneth, apple, apricot, artichoke, arugula, asparagus, avocado, banana, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sunflower, sweet potato, sweetgum, tangerine, tea, tobacco, tomato, turf, a vine, watermelon, yams, or zucchini. In preferred embodiments, the transgenic plant is millet, switchgrass, maize, sorghum, wheat, oat, turf grass, pasture grass, flax, rice, sugarcane, oilseed rape, or barley.

In yet another embodiment, a transgenic plant of the invention comprises a heterologous nucleic acid molecule comprising a promoter sequence. In yet another embodiment, a transgenic plant of the invention may comprise a heterologous nucleic acid molecule which encodes for at least one additional desired trait. The additional trait may be encoded on the same heterologous nucleic acid molecule as a molecule of the invention, or it may be encoded on a second heterologous nucleic acid molecule. The additional desired trait may confer insect resistance to a second insect pest, insect resistance to the same insect pest, abiotic stress tolerance, male sterility, herbicide resistance, bacterial disease resistance, fungal disease resistance, viral disease resistance, nematode resistance, modified fatty acid metabolism, modified carbohydrate metabolism, improved nutritional value, improved performance in an industrial process or altered reproductive capability. The additional desired trait may also induce production within the plant of a commercially valuable enzyme or metabolite.

In embodiments, the desired added trait is a second pesticidal agent. The second pesticidal agent may be active on any plant pest, including insects, nematodes, fungi, viruses or bacteria. Examples of insect plant pests include and are not limited to *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (whitebacked planthopper)); *Blissus* spp. (e.g. *B. leucopterus leucopterus* (chinch bug)); *Scotinophora* spp. (e.g. *S. vermidulate* (rice blackbug)); *Acrosternum* spp. (e.g. *A. hilare* (green stink bug)); *Parnara* spp. (e.g. *P. guttata* (rice skipper)); *Chilo* spp. (e.g. *C. suppressalis* (rice striped stem borer), *C. auricilius* (gold-fringed stem borer), or *C. polychrysus* (dark-headed stem borer)); *Chilotraea* spp. (e.g. *C. polychrysa* (rice stalk borer)); *Sesamia* spp. (e.g. *S. inferens* (pink rice borer)); *Tryporyza* spp. (e.g. *T. innotata* (white rice borer), or *T. incertulas* (yellow rice borer)); *Cnaphalocrocis* spp. (e.g. *C. medinalis* (rice leafroller)); *Agromyza* spp. (e.g. *A. oryzae* (leafminer), or *A. parvicornis* (corn blot leafminer)); *Diatraea* spp. (e.g. *D. saccharalis* (sugarcane borer), or *D. grandiosella* (southwestern corn borer)); *Narnaga* spp. (e.g. *N. aenescens* (green rice caterpillar)); *Xanthodes* spp. (e.g. *X. transversa* (green caterpillar)); *Spodoptera* spp. (e.g. *S. frugiperda* (fall armyworm), *S. exigua* (beet armyworm), *S. littoralis* (climbing cutworm) or *S. praefica* (western yellowstriped armyworm)); *Mythimna* spp. (e.g. *Mythmna* (*Pseudaletia*) *seperata* (armyworm)); *Helicoverpa* spp. (e.g. *H. zea* (corn earworm)); *Colaspis* spp. (e.g. *C. brunnea* (grape colaspis)); *Lissorhoptrus* spp. (e.g. *L. oryzophilus* (rice water weevil)); *Echinocnemus* spp. (e.g. *E. squamos* (rice plant weevil)); *Diclodispa* spp. (e.g. *D. armigera* (rice hispa)); *Oulema* spp. (e.g. *O. oryzae* (leaf beetle); *Sitophilus* spp. (e.g. *S. oryzae* (rice weevil)); *Pachydiplosis* spp. (e.g. *P. oryzae* (rice gall midge)); *Hydrellia* spp. (e.g. *H. griseola* (small rice leafminer), or *H. sasakii* (rice stem maggot)); *Chlorops* spp. (e.g. *C. oryzae* (stem maggot)); *Diabrotica* spp. (e.g. *D. virgifera virgifera* (western corn rootworm), *D. barberi* (northern corn rootworm), *D. undecimpunctata howardi* (southern corn rootworm), *D. virgifera zeae* (Mexican corn rootworm); *D. balteata* (banded cucumber beetle)); *Ostrinia* spp. (e.g. *O. nubilalis* (European corn borer)); *Agrotis* spp. (e.g. *A. ipsilon* (black cutworm)); *Elasmopalpus* spp. (e.g. *E. lignosellus* (lesser cornstalk borer)); *Melanotus* spp. (wireworms); *Cyclocephala* spp. (e.g. *C. borealis* (northern masked chafer), or *C. immaculata* (southern masked chafer)); *Popillia* spp. (e.g. *P. japonica* (Japanese beetle)); *Chaetocnema* spp. (e.g. *C. pulicaria* (corn flea beetle)); *Sphenophorus* spp. (e.g. *S. maidis* (maize billbug)); *Rhopalosiphum* spp. (e.g. *R. maidis* (corn leaf aphid)); *Anuraphis* spp. (e.g. *A. maidiradicis* (corn root aphid)); *Melanoplus* spp. (e.g. *M. femurrubrum* (red-legged grasshopper) *M. differentialis* (differential grasshopper) or *M. sanguinipes* (migratory grasshopper)); *Hylemya* spp. (e.g. *H. platura* (seedcorn maggot)); *Anaphothrips* spp. (e.g. *A. obscrurus* (grass *thrips*)); *Solenopsis* spp. (e.g. *S. milesta* (thief ant)); or spp. (e.g. *T. urticae* (twospotted spider mite), *T. cinnabarinus* (carmine spider mite); *Helicoverpa* spp. (e.g. *H. zea* (cotton bollworm), or *H. armigera* (American bollworm)); *Pectinophora* spp. (e.g. *P. gossypiella* (pink bollworm)); *Earias* spp. (e.g. *E. vittella* (spotted bollworm)); *Heliothis* spp. (e.g. *H. virescens* (tobacco budworm)); *Anthonomus* spp. (e.g. *A. grandis* (boll weevil)); *Pseudatomoscelis* spp. (e.g. *P. seriatus* (cotton fleahopper)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion *thrips*)); *Frankliniella* spp. (e.g. *F. fusca* (tobacco *thrips*), or *F. occidentalis* (western flower thrips)); *Leptinotarsa* spp. (e.g. *L. decemlineata* (Colorado potato beetle), *L. juncta* (false potato beetle), or *L. texana* (Texan false potato beetle)); *Lema* spp. (e.g. *L. trilineata* (three-lined potato beetle)); *Epitrix* spp. (e.g. *E. cucumeris* (potato flea beetle), *E. hirtipennis* (flea beetle), or *E. tuberis* (tuber flea beetle)); *Epicauta* spp. (e.g. *E. vittata* (striped blister beetle)); *Phaedon* spp. (e.g. *P. cochleariae* (mustard leaf beetle)); *Epilachna* spp. (e.g. *E. varivetis* (mexican bean beetle)); *Acheta* spp. (e.g. *A. domesticus* (house cricket)); *Empoasca* spp. (e.g. *E. fabae* (potato leafhopper)); *Myzus* spp. (e.g. *M. persicae* (green peach aphid)); *Paratrioza* spp. (e.g. *P. cockerelli* (psyllid)); *Conoderus* spp. (e.g. *C. falli* (southern potato wireworm), or *C. vespertinus* (tobacco wireworm)); *Phthorimaea* spp. (e.g. *P. operculella* (potato tuberworm)); *Macrosiphum* spp. (e.g. *M. euphorbiae* (potato aphid)); *Thyanta* spp. (e.g. *T. pallidovirens* (redshouldered stinkbug)); *Phthorimaea* spp. (e.g. *P. operculella* (potato tuberworm)); *Helicoverpa* spp. (e.g. *H. zea* (tomato fruitworm); *Keiferia* spp. (e.g. *K. lycopersicella* (tomato pinworm)); *Limonius* spp. (wireworms); *Manduca* spp. (e.g. *M. sexta* (tobacco hornworm), or *M. quinquemaculata* (tomato hornworm)); *Liriomyza* spp. (e.g. *L. sativae, L. trifolli* or *L. huidobrensis* (leafminer)); *Drosophilla* spp. (e.g. *D. melanogaster, D. yakuba, D. pseudoobscura* or *D. simulans*); *Carabus* spp. (e.g. *C. granulatus*); *Chironomus* spp. (e.g. *C. tentanus*); *Ctenocephalides* spp. (e.g. *C. felis* (cat flea)); *Diaprepes* spp. (e.g. *D. abbreviatus* (root weevil)); *Ips* spp. (e.g. *I. pini* (pine engraver)); *Tribolium* spp. (e.g. *T. castaneum* (red floor beetle)); *Glossina* spp. (e.g. *G. morsitans* (tsetse fly)); *Anopheles* spp. (e.g. *A. gambiae* (malaria mosquito)); *Helicoverpa* spp. (e.g. *H. armigera* (African Bollworm)); *Acyrthosiphon* spp. (e.g. *A. pisum* (pea aphid)); *Apis* spp. (e.g. *A. melifera* (honey bee)); *Homalodisca* spp. (e.g. *H. coagulate* (glassy-winged sharpshooter)); *Aedes* spp. (e.g. *Ae. aegypti* (yellow fever mosquito)); *Bombyx* spp. (e.g. *B. mori* (silkworm)); *Locusta* spp. (e.g. *L. migratoria* (migratory locust)); *Boophilus* spp. (e.g. *B. microplus* (cattle tick)); *Acanthoscurria* spp. (e.g. *A. gomesiana* (red-haired chololate bird eater)); *Diploptera* spp. (e.g. *D. punctata* (pacific beetle cockroach)); *Heliconius* spp. (e.g. *H. erato* (red passion flower butterfly) or *H. melpomene* (postman butterfly)); *Curculio* spp. (e.g. *C. glandium* (acorn weevil)); *Plutella* spp. (e.g. *P. xylostella* (diamondback moth)); *Amblyomma* spp. (e.g. *A. variegatum* (cattle tick)); *Anteraea* spp. (e.g. *A. yamamai* (silkmoth)); and *Annigeres* spp. (e.g. *A. subalbatus*).

The insecticidal proteins of the invention can be used in combination with other pesticidal agents (e.g. Bt Cry proteins) to increase pest target range. Furthermore, the use of the insecticidal proteins of the invention in combination with an insecticidal agent which has a different mode of action or target a different receptor in the insect gut has particular utility for the prevention and/or management of insect resistance.

The second pesticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry23 protein, a Cry36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP (Vegetative Insecticidal Protein, disclosed in U.S. Pat. Nos. 5,849,870 and 5,877,012, herein incorporated by reference), a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A (U.S. Pat. No. 7,276,583, incorporated by reference herein), eCry3.1Ab (U.S. Pat. No. 8,309,516, incorporated by reference herein), and Vip3A proteins, including Vip3Aa (U.S. Pat. No. 6,137,033, incorporated by reference herein).

In other embodiments, a transgenic plant of the invention may comprise a second pesticidal agent which may be derived from sources other than *B. thuringiensis*. The second insecticidal agent can be an agent selected from the group comprising an a amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphaericus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin. In other embodiments, the second agent may be at least one insecticidal protein derived from an insecticidal toxin complex (Tc) from *Photorhabdus, Xenorhabus, Serratia,* or *Yersinia*. In other embodiments. The insecticidal protein may be an ADP-ribosyltransferase derived from an insecticidal bacteria, such as *Photorhabdus* ssp. In still other embodiments, the insecticidal protein may Axmi205 or derived from Axmi205 (U.S. Pat. Nos. 8,575, 425 and 9,394,345, each incorporated herein by reference). In other embodiments, the insecticidal protein may be a VIP protein, such as VIP1 and/or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In some embodiments, the transgenic plant of the invention may comprise and/or express at least a second pesticidal agent which is non-proteinaceous. In some embodiments, the second pesticidal agent may be present on the surface of the plant, for example as a topical application. In preferred embodiments, the second pesticidal agent is an interfering RNA molecule. An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention, or may target a different pest. The targeted insect plant pest may feed by chewing, sucking, or piercing. Interfering RNAs are known in the art to be useful for insect control. In embodiments, the dsRNA useful for insect control is described in PCT Patent Application Nos. PCT/US17/044825; PCT/US17/044831; PCT/US17/044832, herein incorporated by reference. In embodiments, the dsRNA useful for insect control is described in U.S. Pat. No. 9,238,822, 9,340,797, or 8,946,510, herein incorporated by reference. In embodiments, the dsRNA useful for insect control is described in U.S. patent application Ser. No. 12/868,994, 13/831,230, 14/207,313, or 14/207,318, herein incorporated by reference. In other embodiments, the interfering RNA may confer resistance against a non-insect plant pest, such as a nematode pest or a virus pest.

The co-expression of more than one pesticidal agent in the same transgenic plant can be achieved by making a single recombinant vector comprising coding sequences of more than one pesticidal agent in a so called molecular stack and genetically engineering a plant to contain and express all the pesticidal agents in the transgenic plant. Such molecular stacks may be also be made by using mini-chromosomes as described, for example in U.S. Pat. No. 7,235,716. Alternatively, a transgenic plant comprising one nucleic acid encoding a first pesticidal agent can be re-transformed with a different nucleic acid encoding a second pesticidal agent and so forth. Alternatively, a plant, Parent 1, can be genetically engineered for the expression of genes of the present invention. A second plant, Parent 2, can be genetically engineered for the expression of a second pesticidal agent. By crossing Parent 1 with Parent 2, progeny plants are obtained which express all the genes introduced into Parents 1 and 2.

Transgenic plants or seed comprising and/or expressing an insecticidal protein of the invention can also be treated with an insecticide or insecticidal seed coating as described in U.S. Pat. Nos. 5,849,320 and 5,876,739, herein incorporated by reference. In embodiments, where both the insecticide or insecticidal seed coating and the transgenic plant or seed of the invention are active against the same target insect, for example a Coleopteran pest or a *Diabrotica* target pest, the combination is useful (i) in a method for further enhancing activity of the composition of the invention against the target insect, and/or (ii) in a method for preventing development of resistance to the composition of the invention by providing yet another mechanism of action against the target insect. Thus, in embodiments, the invention provides a method of enhancing control of a *Diabrotica* insect population comprising providing a transgenic plant or seed of the invention and applying to the plant or the seed an insecticide or insecticidal seed coating to a transgenic plant or seed of the invention.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to a transgenic seed of the invention, which, in some embodiments, has activity against coleopteran and some lepidopteran insects, the coated transgenic seed produced controls both lepidopteran and coleopteran insect pests.

Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorphyrifos), Fortress® (chlorethoxyfos), Mocap® (ethoprop), Thimet® (phorate), AAstar® (phorate, flucythinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

The present invention also encompasses a composition comprising an effective insect-controlling amount of an insecticidal protein according to the invention. In further embodiments, the composition comprises a suitable agricultural carrier and a polypeptide of the invention with insecticidal activity. The agricultural carrier may include adjuvants, mixers, enhancers, etc. beneficial for application of an active ingredient, such as a polypeptide of the invention, including a polypeptide comprising an amino acid sequence that is at least 60%, at least 65%, at least 70%, at least 75%, at least 80%, at least 85%, at least 90%, at least 95%, or 100% identical to of any of SEQ ID NO: 1, SEQ ID NO: 37 to 72, SEQ ID NO: 86 to 96, or SEQ ID NO: 100. Suitable carriers should not be phytotoxic to valuable crops, particularly at the concentrations employed in applying the compositions in the presence of crops, and should not react chemically with the compounds of the active ingredient herein, namely a polypeptide of the invention, or other composition ingredients. Such mixtures can be designed for application directly to crops, or can be concentrates or formulations which are normally diluted with additional carriers and adjuvants before application. They may include inert or active components and can be solids, such as, for example, dusts, powders, granules, water dispersible granules, or wettable powders, or liquids, such as, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like. In another embodiment, a polypeptide of the invention may be encapsulated in a synthetic matrix such as a polymer and applied to the surface of a host such as a plant. Ingestion of the host cells by an insect permits delivery of the insect control agents to the insect and results in a toxic effect in the insect pest.

In further embodiments, a composition of the invention may be a powder, dust, pellet, granule, spray, emulsion, colloid, or solution. A composition of the invention may be prepared by desiccation, lyophilization, homogenization, extraction, filtration, centrifugation, sedimentation, or concentration of a culture of bacterial cells. A composition of the invention may comprise at least 1%, at least 5%, at least 10%, at least 20%, at least 25%, at least 30%, at least 35%, at least 40%, at least 50%, at least 60%, at least 70%, at least 80%, at least 90%, at least 95%, at least 97%, or at least 99% by weight a polypeptide of the invention.

In embodiments, a composition of the invention may comprise at least a second pesticidal agent (e.g., which may be expressed transgenically from the plant and/or be incorporated into the composition), which may be insecticidal, nematicidal, fungicidal, or bactericidal. At least a second pesticidal agent may be insecticidal to the same insect as a polypeptide of the invention or to a different insect. The second pesticidal agent may be a polypeptide. The pesticidal agent may be an interfering RNA (e.g., a dsRNA). The second pesticidal agent may be a microorganism, such as a bacteria, which comprises a nucleic acid molecule that encodes for a pesticidal agent and/or contains a pesticidal agent such as a polypeptide or interfering RNA. The microorganism may be attenuated, heat-inactivated, or lyophilized. The microorganism may be dead or unable to reproduce. The second pesticidal agent may be an insecticide, for example carbofuran, carbaryl, methomyl, bifenthrin, tefluthrin, permethrin, cyfluthrin, lambda-cyhalothrin, cypermethrin, deltamethrin, chlorpyrifos, chlorethoxyfos, clothianidin, dimethoate, ethoprophos, malathion, methyl-parathion, phorate, terbufos, tebupirimiphos, fipronil, acetamiprid, imidacloprid, thiacloprid, thiamethoxam, endosulfan, bensultap, or a combination thereof, or a commercial product containing such insecticides and insecticidal seed coatings as described above.

A composition of the invention, for example a composition comprising a polypeptide of the invention and an agriculturally acceptable carrier, may be used in conventional agricultural methods. An agriculturally acceptable carrier is a formulation useful for applying a composition comprising a polypeptide of the invention to a plant or seed. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

The present invention also comprises a method for controlling a Lepidopteran and/or Coleopteran pest population comprising contacting said population with an effective insect-controlling amount of a polypeptide of the invention with insecticidal activity, where the polypeptide is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to SEQ ID NO: 1, SEQ ID NO: 37 to 72, SEQ ID NO: 86 to 96, or SEQ ID NO: 100. Contacting includes members of the pest population feeding on or ingesting the polypeptide. The polypeptide may be incorporated into insect diet food or may be expressed in or present on plant tissue which the insect then ingests. In further embodiments, controlling the Lepidopteran and/or Coleopteran pest populations includes killing the insects by contacting the insects with an effective insect-controlling amount of a polypeptide of the invention.

The present invention also comprises a method for protecting a plant from an insect pest, comprising expressing in a plant or plant cell a nucleotide sequence or expression cassette that encodes an insecticidal polypeptide of the invention. In embodiments, the nucleotide sequence is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of SEQ ID NO: 2 to 36 or encodes a polypeptide comprising an amino acid sequence that is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to SEQ ID NO: 1, SEQ ID NO: 37 to 72, SEQ ID NO: 86 to 96, or SEQ ID NO: 100. In further embodiments, the plant or plant cell produces an insecticidal polypeptide having insecticidal activity against a Lepidopteran and/or Coleopteran pest.

The present invention also comprises a method for increasing yield in a plant comprising growing in a field a plant, or a seed thereof, having stably incorporated into its genome a nucleic acid molecule of an expression cassette of the invention, and wherein said field is infested with a pest against which said polypeptide has insecticidal activity.

Once a desired nucleic acid has been transformed into a particular plant species, it may be propagated in that species or moved into other varieties of the same species, particularly including commercial varieties, using traditional breeding techniques.

In embodiments, a nucleic acid of this invention is expressed in transgenic plants, thus causing the biosynthesis of the corresponding insecticidal protein in the transgenic plants. In this way, transgenic plants with enhanced resistance to insects, particularly corn rootworm, are generated. For their expression in transgenic plants, the nucleic acids of the invention may optionally be modified and optimized. Although in many cases genes from microbial organisms can be expressed in plants at high levels without modification, low expression in transgenic plants may result from microbial nucleic acids having codons that are not preferred in plants. It is known in the art that all organisms have specific preferences for codon usage, and the codons of the nucleic acids described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleic acids that have low GC contents may express poorly in plants due to the existence of ATTTA motifs that may destabilize messages, and AATAAA motifs that may cause inappropriate polyadenylation. In embodiments, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleic acids are screened for the existence of illegitimate splice sites that may cause message truncation. All changes required to be made within the nucleic acids such as those described above can be made using well known techniques of site directed mutagenesis, PCR, and synthetic gene construction, for example, using the methods described in the published patent applications EP 0 385 962, EP 0 359 472, and WO 93/07278.

In one embodiment of the invention a coding sequence for an insecticidal protein of the present invention is made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al., Nucleic Acids Research 17:477-498 (1989), the disclosure of which is incorporated herein by reference.

In this manner, the nucleotide sequences can be optimized for expression in any plant. It is recognized that all or any part of the gene sequence may be optimized or synthetic. That is, synthetic or partially optimized sequences may also be used.

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clontech suggests a further consensus translation initiator (1993/1994 catalog, page 210). These consensus sequences are suitable for use with the nucleic acids of this invention. In embodiments, the sequences are incorporated into constructions comprising the nucleic acids, up to and including the ATG (whilst leaving the second amino acid unmodified), or alternatively up to and including the GTC subsequent to the ATG (with the possibility of modifying the second amino acid of the transgene).

Expression of the nucleic acids in transgenic plants is driven by promoters that function in plants. The choice of promoter will vary depending on the temporal and spatial requirements for expression, and also depending on the target species. Thus, expression of the nucleic acids of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleic acids in the desired cell.

In one embodiment promoters are used that are expressed constitutively including the actin or ubiquitin or CMP promoters or the CaMV 35S and 19S promoters. The nucleic acids of this invention can also be expressed under the regulation of promoters that are chemically regulated. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

In another embodiment a category of promoters which is wound inducible can be used. Numerous promoters have been described which are expressed at wound sites and also at the sites of phytopathogen infection. Ideally, such a promoter should only be active locally at the sites of infection, and in this way the insecticidal proteins of the invention only accumulate in cells that need to synthesize the proteins to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue-specific or tissue-preferential promoters useful for the expression of genes encoding insecticidal proteins of the invention in plants, particularly corn, are those which direct expression in root, pith, leaf or pollen, particularly root. Such promoters, e.g. those isolated from PEPC or trpA, are disclosed in U.S. Pat. No. 5,625,136, or MTL, disclosed in U.S. Pat. No. 5,466,785. Both U. S. patents are herein incorporated by reference in their entirety.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In further aspects, the nucleotide sequences of the invention can be operably associated with a promoter that is wound inducible or inducible by pest or pathogen infection (e.g., a insect or nematode plant pest). Numerous promoters have been described which are expressed at wound sites and/or at the sites of pest attack (e.g., insect/nematode feeding) or phytopathogen infection. Ideally, such a promoter should be active only locally at or adjacent to the sites of attack, and in this way expression of the nucleotide sequences of the invention will be focused in the cells that are being invaded or fed upon. Such promoters include, but are not limited to, those described by Stanford et al., Mol. Gen. Genet. 215:200-208 (1989), Xu et al. Plant Molec. Biol. 22:573-588 (1993), Logemann et al. Plant Cell 1:151-158 (1989), Rohrmeier and Lehle, Plant Molec. Biol. 22:783-792 (1993), Firek et al. Plant Molec. Biol. 22:129-142 (1993), Warner et al. Plant J. 3:191-201 (1993), U.S. Pat. Nos. 5,750,386, 5,955,646, 6,262,344, 6,395,963, 6,703,541, 7,078,589, 7,196,247, 7,223,901, and U.S. Patent Application Publication 2010043102.

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleic acids of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleic acid. Many such target sequences are known for the chloroplast and their functioning in heterologous constructions has been shown. The expression of the nucleic acids of the present invention is also targeted to the endoplasmic reticulum or to the vacuoles of the host cells. Techniques to achieve this are well known in the art.

Vectors suitable for plant transformation are well-known in the art. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors comprising the nucleic acid molecules of the present invention may also comprise genes (e.g. phosphomannose isomerase; PMI) which provide for positive selection of the transgenic plants as disclosed in U.S. Pat. Nos. 5,767,378 and 5,994,629, herein incorporated by reference. The choice of selectable marker is not, however, critical to the invention.

In embodiments, the nucleic acid can be transformed into the nuclear genome. In another embodiment, a nucleic acid of the present invention is directly transformed into the plastid genome. A major advantage of plastid transformation is that plastids are generally capable of expressing bacterial genes without substantial codon optimization, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid of the present invention is inserted into a plastid-targeting vector and transformed into the plastid genome of a desired plant host. Plants homoplastic for plastid genomes containing a nucleic acid of the present invention are obtained, and are preferentially capable of high expression of the nucleic acid.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al., Molecular Cloning: *A Laboratory Manual*, 3d Ed., Cold Spring Harbor, N.Y.: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1: Identification of a Protein with Insecticidal Activity Against Western Corn Rootworm An insecticidal protein (SEQ ID NO: 1) was identified from *Woodsholea maritima*. An *E. coli*-optimized version of this gene was synthesized (SEQ ID NO: 2) and the gene was cloned into a pET29a vector, creating construct pET29a (Woods). The pET29a(Woods) construct was transformed into *E. coli* BL21* (DE3) and protein expression was carried out in Luria-Bertani broth with IPTG induction at 18° C. overnight. The soluble fraction of lysates was prepared from these cultures by use of a French pressure cell followed by centrifugation of whole lysates at 20,000×g for thirty minutes. The supernatant (soluble fraction) was then tested for bioactivity to Western Corn Rootworm (WCR).

Bioactivity assays were performed using a diet-incorporation method. Briefly, *E. coli* BL21*(DE3) lysates were mixed with an equal volume of heated artificial insect diet (Bioserv, Inc., Frenchtown, N.J.) in 1.5 mL centrifuge tubes and then applied to small petri-dishes. After the diet-sample mixture cooled and solidified, 12 WCR larvae were added to each plate. The plates were sealed and maintained at ambient laboratory conditions with regard to temperature, lighting and relative humidity. Lysates from *E. coli* BL21* (DE3) cultures harboring the empty pET29a vector were used as negative controls. Mortality was assessed on day 4 and day 7. For this and all subsequent tables showing insecticidal activity on CRW, the abbreviations for the "Remarks" column are as follows: s=small larvae, sm=small/medium larvae, m=medium larvae, mb=medium/big larvae, b=big larvae, vb=very big larvae. As shown in Table 1, lysate from the culture expressing pET29a(Woods) showed strong bioactivity against WCR. The *W. maritima* protein was renamed WoodsCRW.

TABLE 1

Insecticidal activity against Western Corn Rootworm

| Treatment | Day 4 | | Day 7 | | Remarks |
|---|---|---|---|---|---|
| | Dead | % Mortality | Dead | % Mortality | |
| 50 mM KPi pH 7.0, 50 mM NaCl | 0 | 0 | 2 | 17 | m, b |
| BL21*/pET29a (empty) | 1 | 8 | 2 | 17 | m, b |
| BL21*/pET29a (Woods) | 10 | 83 | 12 | 100 | |

The WoodsCRW protein in the lysate preparation was quantitated by Bio-Rad Experion and BCA protein assay and re-tested against 12 WCR larvae over a range of concentrations in a diet-incorporation bioassay (Table 2). WoodsCRW showed strong bioactivity to WCR over the range of concentrations tested.

TABLE 2

Insecticidal activity of WoodsCRW lysate against WCR

| WoodsCRW (µg/mL) | Day 4 | | Day 6 | | Remarks |
|---|---|---|---|---|---|
| | Dead | % Mortality | Dead | % Mortality | |
| 250 | 10 | 83 | 12 | 100 | |
| 100 | 10 | 83 | 12 | 100 | |
| 50 | 9 | 75 | 12 | 100 | |
| 25 | 6 | 50 | 11 | 92 | m |
| 12.5 | 3 | 25 | 5 | 42 | m |
| 5.0 | 0 | 0 | 2 | 17 | mb |
| 2.5 | 2 | 17 | 4 | 33 | m |
| BL21*/pET29a (empty) | 0 | 0 | 0 | 0 | b |
| 50 mM KPi pH 7.0, 50 mM NaCl | 0 | 0 | 0 | 0 | b |

Example 2: Purified WoodsCRW Possesses Insecticidal Activity Against Western Corn Rootworm A pET-6His-SUMO construct comprising SEQ ID NO: 2 was produced for WoodsCRW. The pET-6His-SUMO-WoodsCRW construct was transformed into *E. coli* BL21* (DE3) for protein production. The SUMO-tagged protein was purified using standard techniques for a His-tagged protein and subsequently cleaved with SUMO protease to liberate tag-free WoodsCRW protein. The cleaved protein was then applied to a HisTrapFF FPLC column and the column flow-through was collected. The flow-through fractions were analyzed for purity by SDS-PAGE (The expected MW of WoodsCRW is 54.1 kDa.). The purified WoodsCRW was then dialyzed into 1×PBS overnight at 4° C. and then concentrated to 13 mg/mL. The pure protein was then tested against 12 WCR larvae over a range of concentrations in the diet-incorporation method described in Example 1. As shown in Table 3, WoodsCRW is very efficacious against WCR; WoodsCRW at 6 µg/mL produced 83% mortality at day 6.

TABLE 3

Insecticidal activity of Purified WoodsCRW against WCR

| (µg/mL) | Day 3 | | | Day 6 | | |
|---|---|---|---|---|---|---|
| | Dead | % Mortality | Remarks | Dead | % Mortality | Remarks |
| 1×PBS | 0 | 0 | | 0 | 0 | b |
| 100 | 7 | 58 | s | 12 | 100 | |

TABLE 3-continued

Insecticidal activity of Purified WoodsCRW against WCR

| (µg/mL) | Day 3 | | | Day 6 | | |
|---|---|---|---|---|---|---|
| | Dead | % Mortality | Remarks | Dead | % Mortality | Remarks |
| 50 | 9 | 75 | s | 11 | 92 | s |
| 25 | 7 | 58 | s | 12 | 100 | |
| 12.5 | 3 | 25 | s | 11 | 92 | m |
| 6.3 | 1 | 8 | s | 10 | 83 | m |
| 3.1 | 0 | 0 | sm | 3 | 25 | mb |
| 1.6 | 2 | 17 | sm | 4 | 33 | mb |

Example 3: WoodsCRW Possesses Insecticidal Activity Against Northern Corn Rootworm WoodsCRW was purified as in Example 2 and was tested for efficacy against 12 Northern Corn Rootworm (NCR) larvae in a diet-incorporation assay, performed essentially as described in Example 1, except mortality was assessed on day 3 and day 7. WoodsCRW was tested at concentrations of 0.2 mg/mL and 0.1 mg/mL. The negative control had only 1×PBS. As shown in Table 4, WoodsCRW demonstrates insecticidal activity against NCR.

TABLE 4

Insecticidal activity of WoodsCRW against NCR

| Treatment | Day 3 | | Day 7 | | Remarks |
|---|---|---|---|---|---|
| | Dead | % Mort | Dead | % Mort | |
| 1× PBS | 0 | 0% | 0 | 0% | b |
| 0.2 mg/mL | 4 | 33% | 11 | 92% | s |
| 0.1 mg/mL | 3 | 25% | 12 | 100% | s |

Example 4: WoodsCRW Possesses Insecticidal Activity Against Cry-Resistant Western Corn Rootworm To determine if WoodsCRW toxicity is through a mode-of-action separate from Cry3-related proteins, WoodsCRW was purified as in Example 2 and was tested for efficacy against a strain of WCR that is resistant to the mCry3A toxin (mCry3A-R) and against a strain of WCR that is resistant to the eCry3.1Ab toxin (eCry3.1Ab-R). Diet-incorporation assays were performed essentially as described in Example 1, except mortality was assessed on day 4 and day 6. Purified WoodsCRW was tested at two different concentrations, 0.2 mg/mL and 0.075 mg/mL. The negative control had only 1×PBS. WCR that is not resistant to mCry3A or eCry3.1Ab (sus=susceptible) was also assayed. Each assay was performed with 12 WCR larvae. As shown in Table 5, WoodsCRW demonstrates insecticidal activity against Cry-resistant WCR strains.

TABLE 5

Insecticidal activity of WoodsCRW against Cry-R WCR

| Treatment | Day 4 | | | Day 6 | | |
|---|---|---|---|---|---|---|
| | Dead | % Mort | Remarks | Dead | % Mort | Remarks |
| sus, 0.2 mg/mL | 12 | 100% | | 12 | 100% | |
| sus, 0.075 mg/mL | 11 | 92% | 1m | 11 | 92% | 1m |

TABLE 5-continued

Insecticidal activity of WoodsCRW against Cry-R WCR

| | Day 4 | | | Day 6 | | |
|---|---|---|---|---|---|---|
| Treatment | Dead | % Mort | Remarks | Dead | % Mort | Remarks |
| sus, 1x PBS | 0 | 0% | 12mb | 1 | 8% | 11mb |
| mCry3A-R, 0.2 mg/mL | 9 | 75% | 3m | 12 | 100% | |
| mCry3A-R, 0.075 mg/mL | 6 | 50% | 6m | 10 | 83% | 2m |
| mCry3A-R, 1x PBS | 0 | 0% | 12mb | 3 | 25% | 9mb |
| eCry3.1Ab-R, 0.2 mg/mL | 10 | 83% | 2sm | 12 | 100% | |
| eCry3.1Ab-R, 0.075 mg/mL | 9 | 75% | 3m | 11 | 92% | 1m |
| eCry3.1Ab-R, 1x PBS | 0 | 0% | 12mb | 0 | 0% | 12mb |

Example 5: WoodsCRW does not Possess Insecticidal Activity Against Lepidopterans Lysates from bacterial cultures expressing WoodsCRW (SEQ ID NO: 2) was tested for bioactivity on a panel of Lepidopteran insect pests using diet-overlay bioassays. European corn borer (ECB), black cutworm (BCW), and corn earworm (CEW), and Fall armyworm (FAW) were each tested for WoodsCRW insecticidal activity by a diet-incorporation assay similar to that of Example 1. 12 L1 larvae were tested for each experiment, using lysates from B121* (DE3) bacterial cultures harboring a gene encoding for WoodsCRW (SEQ ID NO: 2). A positive-control sample for BCW, CEW, and FAW consisted of larvae exposed to *E. coli* B121* (DE3) lysates expressing Vip3A (U.S. Pat. No. 5,877,012, incorporated by reference herein). 1×PBS alone and lysates from B121* (DE3) bacterial cultures harboring the empty pET29 vector were used as negative controls. Mortality was assessed on day 7. Larvae that reach the L3 stage were not significantly affected by the treatment. If larvae only reach L2 stage, then it is possible that the treatment caused growth inhibition. If the larvae remain at the L1 stage throughout the treatment then growth inhibition occurred. This can also be considered "effective mortality" as the larvae will not develop beyond the L1 stage even if they remain alive. WoodsCRW was not active against the tested Lepidopteran insect pests in these experimental conditions (Table 6).

TABLE 6

Insecticidal activity of WoodsCRW against Lepidopterans

| | | | Day 7 | |
|---|---|---|---|---|
| Insect | Treatment | Dead | % Mort | Remarks |
| CEW | BL21*/pET29a (empty) | 0 | 0% | 12L3 |
| CEW | BL21*/WoodsCRW | 0 | 0% | 12L3 |
| CEW | BL21*/pET29a(Vip3A) | 9 | 75% | 3L1 |
| CEW | 50 mM KPi pH 7.0, 50 mM NaCl | 0 | 0% | 12L3 |
| ECB | BL21*/pET29a (empty) | 0 | 0% | 12L3 |
| ECB | BL21*/WoodsCRW | 0 | 0% | 12L3 |
| ECB | BL21*/pET29a(Vip3A) | 0 | 0% | 12L3 |
| ECB | 50 mM KPi pH 7.0, 50 mM NaCl | 0 | 0% | 12L3 |
| BCW | BL21*/pET29a (empty) | 0 | 0% | 12L3 |
| BCW | BL21*/WoodsCRW | 0 | 0% | 12L3 |
| BCW | BL21*/pET29a(Vip3A) | 12 | 100% | |
| BCW | 50 mM KPi pH 7.0, 50 mM NaCl | 0 | 0% | 12L3 |
| FAW | BL21*/pET29a (empty) | 0 | 0% | 2L2 10L3 |
| FAW | BL21*/WoodsCRW | 0 | 0% | 1L2 11L3 |
| FAW | BL21*/pET29a(Vip3A) | 8 | 67% | 4L1 |
| FAW | 50 mM KPi pH 7.0, 50 mM NaCl | 0 | 0% | 12L3 |

L1 = 1st instar,
L2 = 2nd instar,
L3 = 3rd instar

Example 6: Variants of Woods CRW Possess Insecticidal Activity Against WCR

Mutations were introduced into WoodsCRW and the protein stability and insecticidal activity of bacterial lysates comprising the WoodsCRW mutant variant and/or purified WoodsCRW mutant variant protein were assayed. Mutations include amino acid changes at cysteine residues and also the insertion of leucine residues adjacent to cysteine residues. These mutations were introduced to determine if a WoodsCRW mutant variant could be designed which maintained insecticidal activity but would be digestible in a Simulated Gastric Fluid (SGF) assay. Such a WoodsCRW variant may have commercial value, for example through transgenic expression in a plant to confer insecticidal properties to the plant.

Insecticidal activity was determined using diet-incorporation assays performed essentially as described in Example 1, using 12 WCR larvae per experimental assay. Results are shown in Tables 7-19. SEQ ID NOs correspond to the amino acid sequence of the variant. The mutants shown in Tables 14-16 and 19 contain leucine insertions at the stated positions, as indicated by the "-Leu-" or "-L-". For Table 14, 1:20 dilutions of each bacterial lysate was tested. For Tables 15 and 16, the lysate dilutions are shown as part of the treatment. For Tables 17-19, the amounts of purified protein used are shown as part of the treatment. The majority of the mutant WoodsCRW variants show insecticidal activity. However, very few show SGF digestibility.

Example 7: Simulated Gastric Fluid Testing on *E. coli* Lysate Preparations

This example describes the assay performed to determine SGF digestibility. Bacterial lysates in 50 mM potassium phosphate pH 7.0, 50 mM sodium chloride were diluted to 3 mg/mL (total protein concentration) for the digestibility analysis. The digestion reaction was initiated by adding 15 μL lysate to 285 μL simulated gastric fluid [10 Units pepsin/μg protein, or approximately 1579 Units pepsin/mL, in G-Con solution (2 mg/mL sodium chloride, pH 1.2)] at 37° C. At 5 or 10 minutes, 100 μL of the Lysate-SGF reaction was removed and the reaction terminated by adding it to 100 μL of preheated (95° C.) stop solution comprised of 65% Tricine Loading Buffer (Bio-rad 2× Tricine Load Buffer w/10% β-mercaptoethanol) and 35% 500 mM sodium bicarbonate, pH 11.0. A zero time (TO) point was produced by adding 5 μL of test lysate to preheated (95° C.) 100 μL Stop Solution and 95 μL of simulated gastric fluid. All samples were heated at 95° C. for 5 minutes, and then stored on ice until SDS-PAGE analysis. Thirty microliters of each reaction were loaded on a 10-20% Tris-tricine peptide gel prior to standard protein gel electrophoresis. The Tris-tricine gel was fixed for 20 minutes with a 40% methanol: 10% acetic acid mixture immediately after the electrophoresis. The gel was then stained with GelCode Blue protein stain for 1 hour at room temperature. After 1 hour, the polyacrylamide gel was de-stained with distilled water for at least 12 hours. Results are shown qualitatively in Tables 7-19, in the column "SGF". WoodsCRW mutant variants in Table 20 were also tested for digestibility. A "no" (N) means that intact WoodsCRW protein variant was detectable by GelCode Blue protein stain following gel electrophoresis, indicating that the protein was not fully digestible in the SGF assay. A "yes" (Y) means intact WoodsCRW protein variant was not detectable, indicating that the WoodsCRW protein variant was digestible in the SGF assay. For Tables 7-19, if the SGF column does not contain either "N" or "Y" it indicates that the protein was not tested for digestibility.

TABLE 7

Insecticidal activity of mutant variants of WoodsCRW against WCR

| Treatment | SEQ ID NO. | Day 4 Dead | Day 4 % Mort | Day 4 Remarks | Day 6 Dead | Day 6 % Mort | Day 6 Remarks | SGF |
|---|---|---|---|---|---|---|---|---|
| BL21*/pET29 (empty) | | 0 | 0% | mb | 0 | 0% | b | |
| BL21*/WoodsCRW C485S 50 μg/mL | 28 | 7 | 58% | sm | 12 | 100% | | N |
| BL21*/WoodsCRW C485S 25 μg/mL | 28 | 5 | 42% | s | 12 | 100% | | N |
| BL21*/WoodsCRW C435S 50 μg/mL | 29 | 8 | 67% | s | 12 | 100% | | N |
| BL21*/WoodsCRW C435S 25 μg/mL | 29 | 1 | 8% | sm | 7 | 58% | m | N |
| BL21*/WoodsCRW C398S 50 μg/mL | 30 | 8 | 67% | sm | 11 | 92% | m | N |
| BL21*/WoodsCRW C398S 25 μg/mL | 30 | 8 | 67% | sm | 11 | 92% | m | N |
| BL21*/WoodsCRW C383S 50 μg/mL | 31 | 7 | 58% | sm | 10 | 83% | sm | N |
| BL21*/WoodsCRW C383S 25 μg/mL | 31 | 4 | 33% | sm | 9 | 75% | sm | N |
| BL21*/WoodsCRW C313S 50 μg/mL | 32 | 5 | 42% | sm | 11 | 92% | m | N |
| BL21*/WoodsCRW C313S 25 μg/mL | 32 | 7 | 58% | sm | 11 | 92% | s | N |

TABLE 8

Insecticidal activity of mutant variants of WoodsCRW against WCR

| Treatment | SEQ ID NO. | Day 4 Dead | Day 4 % Mort | Day 4 Remarks | Day 6 Dead | Day 6 % Mort | Day 6 Remarks | SGF |
|---|---|---|---|---|---|---|---|---|
| BL21*/pET29a (empty) | | 1 | 8% | m | 1 | 8% | mb | |
| BL21*/WoodsCRW-wt 50 μg/mL | 1 | 9 | 75% | s/m | 11 | 92% | s | |
| BL21*/WoodsCRW Y194W 50 μg/mL | 33 | 2 | 17% | m | 2 | 17% | mb | |
| BL21*/WoodsCRW Y194F 50 μg/mL | 34 | 8 | 67% | s | 12 | 100% | | N |
| BL21*/WoodsCRW C383S/C485S 50 μg/mL | 37 | 6 | 50% | s | 12 | 100% | | N |
| BL21*/WoodsCRW C435S/C485S 50 μg/mL | 38 | 4 | 33% | s (2m) | 11 | 92% | m | N |
| BL21*/WoodsCRW C398S/C435S 50 μg/mL | 39 | 3 | 25% | s/m | 5 | 42% | m | N |
| BL21*/WoodsCRW C398S/C485S 50 μg/mL | 40 | 5 | 42% | s | 8 | 67% | s | N |

TABLE 9

Insecticidal activity of mutant variant of WoodsCRW against WCR

| Treatment | SEQ ID NO. | Day 4 Dead | Day 4 % Mort | Day 4 Remarks | Day 6 Dead | Day 6 % Mort | Day 6 Remarks |
|---|---|---|---|---|---|---|---|
| BL21*/pET29a (empty) |  | 0 | 0% | mb | 0 | 0% | b |
| BL21*/WoodsCRW-wt 50 µg/mL | 1 | 11 | 92% | 1s | 12 | 100% |  |
| BL21*/WoodsCRW C313S C383S C398S C435S C485S 29 µg/mL | 42 | 1 | 8% | mb | 1 | 8% | mb |
| BL21*/WoodsCRW C313S C383S C398S C435S C485S 58 µg/mL | 42 | 0 | 0% | mb | 0 | 0% | mb |
| BL21*/WoodsCRW C313S C383S C398S C435S C485S 145 µg/mL | 42 | 1 | 8% | mb | 1 | 8% | mb |
| BL21*/WoodsCRW C313S C383S C398S C435S C485S 580 µg/mL | 42 | 4 | 33% | m | 4 | 33% | mb |

TABLE 10

Insecticidal activity of mutant variants of WoodsCRW against WCR

| Treatment | SEQ ID NO. | Day 4 Dead | Day 4 % Mort | Day 6 Dead | Day 6 % Mort | Remarks | SGF |
|---|---|---|---|---|---|---|---|
| BL21*/pet29 (empty) |  | 0 | 0% | 3 | 25% | b |  |
| BL21*/WoodsCRW-wt-50 ug/mL | 1 | 8 | 67% | 12 | 100% | s |  |
| Bl21*/WoodsCRW K396L-50 ug/mL | 35 | 4 | 33% | 10 | 83% | m | N |
| BL21*/WoodsCRW K406L-50 ug/mL | 36 | 6 | 50% | 9 | 75% | m | N |
| BL21*/WoodsCRW C383S C435S C485S-50 ug/ml | 41 | 2 | 17% | 5 | 42% | b |  |
| Bl21*/WoodsCRW I77L I83L Y98F-50 ug/mL | 47 | 5 | 42% | 11 | 92% | m |  |
| Bl21*/WoodsCRW Y248F I264L Y277F-50 ug/mL | 48 | 6 | 50% | 10 | 83% | m |  |
| Bl21*/WoodsCRW Y326F I340L I351L-50 ug/mL | 49 | 5 | 42% | 11 | 92% | s |  |

TABLE 11

Insecticidal activity of mutant variant of WoodsCRW against WCR

| Treatment | SEQ ID NO. | Day 4 Dead | Day 4 % Mort | Day 4 Remarks | Day 6 Dead | Day 6 % Mort | Day 6 Remarks |
|---|---|---|---|---|---|---|---|
| BL21*/pET29 (empty) |  | 3 | 25% | m | 5 | 42% | mb |
| BL21*/WoodsCRW I209L Y223F I228L 0.19 mg/mL | 50 | 5 | 42% | s | 11 | 92% | m |

TABLE 12

Insecticidal activity of mutant variant of WoodsCRW against WCR

| Treatment | SEQ ID NO. | Day 4 Dead | Day 4 % Mort | Day 4 Remarks | Day 6 Dead | Day 6 % Mort | Day 6 Remarks | SGF |
|---|---|---|---|---|---|---|---|---|
| BL21*/pET29 (empty) |  | 2 | 17% | mb | 4 | 33% | mb |  |
| BL21*/WoodsCRW I447L Y464F I469L 181 µg/mL | 51 | 12 | 100% |  | 12 | 100% |  | N |
| BL21*/WoodsCRW I447L Y464F I469L 36 µg/mL | 51 | 11 | 92% | s | 12 | 100% |  | N |

TABLE 13

Insecticidal activity of mutant variants of WoodsCRW against WCR

| Treatment | SEQ ID NO. | Day 4 | | | Day 6 | | | SGF |
|---|---|---|---|---|---|---|---|---|
| | | Dead | % Mort | Remarks | Dead | % Mort | Remarks | |
| Bl21*/pet29 (empty) | | 1 | 8% | mb | 1 | 8% | b | |
| Bl21*/WoodsCRW C383A C485A 245 µg/mL | 37 | 9 | 75% | s | 12 | 100% | | N |
| Bl21*/WoodsCRW C383A C485A 49 µg/mL | 37 | 7 | 58% | sm | 11 | 92% | m | N |
| Bl21*/WoodsCRW C398A C485A 213 µg/mL | 44 | 11 | 92% | sm | 12 | 100% | | N |
| Bl21*/WoodsCRW C398A C485A 43 µg/mL | 44 | 3 | 25% | s | 9 | 75% | m | N |
| Bl21*/WoodsCRW C383L 210 µg/mL | 45 | 3 | 25% | sm | 9 | 75% | mb | N |
| Bl21*/WoodsCRW C383L 42 µg/mL | 45 | 7 | 58% | m | 11 | 92% | m | N |
| Bl21*/WoodsCRW C398L 275 µg/mL | 46 | 7 | 58% | s | 12 | 100% | | Y |
| Bl21*/WoodsCRW C398L 55 µg/mL | 46 | 3 | 25% | sm | 9 | 75% | 2m, 1b | Y |

TABLE 14

Insecticidal activity of mutant variants of WoodsCRW against WCR

| Treatment | SEQ ID NO. | Day 4 | | | Day 6 | | | SGF |
|---|---|---|---|---|---|---|---|---|
| | | Dead | % Mort | Remarks | Dead | % Mort | Remarks | |
| BL21*/pET29a-empty vector | | 0 | 0% | b | 1 | 8% | b | |
| BL21*/WoodsCRW Y436F | 89 | 10 | 83% | s | 12 | 100% | | N |
| BL21*/WoodsCRW D397-Leu-C398 | 90 | 10 | 83% | s | 12 | 100% | | Y |
| BL21*/WoodsCRW C398-Leu-V399 | 91 | 7 | 58% | m | 10 | 83% | m | Y |
| BL21*/WoodsCRW L382-Leu-C383 | 92 | 0 | 0% | b | 0 | 0% | b | |
| BL21*/WoodsCRW C383-Leu-Y384 | 93 | 1 | 8% | b | 1 | 8% | b | |
| BL21*/WoodsCRW L434-Leu-C435 | 94 | 0 | 0% | b | 0 | 0% | b | |
| BL21*/WoodsCRW C435-Leu-Y436 | 95 | 5 | 42% | mb | 11 | 92% | m | |

TABLE 15

Insecticidal activity of mutant variants of WoodsCRW against WCR

| Treatment | SEQ ID NO. | Day 3 | | | Day 6 | | | SGF |
|---|---|---|---|---|---|---|---|---|
| | | Dead | % Mort | Remarks | Dead | % Mort | Remarks | |
| BL21*/pET29a-empty vector | | 0 | 0% | b | 1 | 8% | b | |
| BL21*/WoodsCRW Y436F 1:20 | 89 | 9 | 75% | 2s, 1m | 12 | 100% | | N |
| BL21*/WoodsCRW Y436F 1:50 | 89 | 9 | 75% | 2m, 1b | 12 | 100% | | N |
| BL21*/WoodsCRW Y436F 1:200 | 89 | 3 | 25% | sm | 10 | 83% | mb | N |
| BL21*/WoodsCRW D397-Leu-C398 1:20 | 90 | 5 | 42% | mb | 12 | 100% | | N |
| BL21*/WoodsCRW D397-Leu-C398 1:50 | 90 | 3 | 25% | mb | 11 | 92% | b | N |
| BL21*/WoodsCRW D397-Leu-C398 1:200 | 90 | 2 | 17% | m | 11 | 92% | b | N |
| BL21*/WoodsCRW C398-Leu-V399 1:20 | 91 | 3 | 25% | m | 11 | 92% | m | N |
| BL21*/WoodsCRW C398-Leu-V399 1:50 | 91 | 5 | 42% | m | 12 | 100% | | N |
| BL21*/WoodsCRW C398-Leu-V399 1:200 | 91 | 2 | 17% | m | 7 | 58% | mb | N |
| BL21*/WoodsCRW C435-Leu-Y436 1:20 | 95 | 2 | 17% | mb | 6 | 50% | b | |
| BL21*/WoodsCRW C435-Leu-Y436 1:50 | 95 | 1 | 8% | mb | 6 | 50% | b | |
| BL21*/WoodsCRW C435-Leu-Y436 1:200 | 95 | 2 | 17% | b | 4 | 33% | b | |

TABLE 16

Insecticidal activity of mutant variants of WoodsCRW against WCR

| Treatment | SEQ ID NO. | Day 4 Dead | Day 4 % Mort | Day 4 Remarks | Day 6 Dead | Day 6 % Mort | Day 6 Remarks | SGF |
|---|---|---|---|---|---|---|---|---|
| Bl21*/WoodsCRW D397-Leu-Leu-C398 1:20 | 86 | 12 | 100% | | 12 | 100% | | Y |
| Bl21*/WoodsCRW D397-Leu-Leu-C398 1:50 | 86 | 11 | 92% | m | 12 | 100% | | Y |
| Bl21*/WoodsCRW D397-Leu-Leu-C398 1:200 | 86 | 8 | 67% | m | 11 | 92% | m | Y |
| Bl21*/WoodsCRW C398-Leu-Leu-V399 1:20 | 87 | 9 | 75% | m | 11 | 92% | m | Y |
| Bl21*/WoodsCRW C398-Leu-Leu-V399 1:50 | 87 | 7 | 58% | m | 12 | 100% | | Y |
| Bl21*/WoodsCRW C398-Leu-Leu-V399 1:200 | 87 | 3 | 25% | m | 10 | 83% | m | Y |
| Bl21*/WoodsCRW D397-Leu-C398-Leu-V399 1:20 | 88 | 3 | 25% | m | 6 | 50% | | Y |
| Bl21*/WoodsCRW D397-Leu-C398-Leu-V399 1:50 | 88 | 0 | 0% | mb | 2 | 17% | mb | Y |
| Bl21*/WoodsCRW D397-Leu-C398-Leu-V399 1:200 | 88 | 1 | 8% | mb | 3 | 25% | mb | Y |
| Bl21*/WoodsCRW C398L 1:20 | 55 | 10 | 83% | s | 12 | 100% | | Y |
| Bl21*/WoodsCRW C398L 1:50 | 55 | 9 | 75% | m | 12 | 100% | | Y |
| Bl21*/WoodsCRW C398L 1:200 | 55 | 7 | 58% | m | 9 | 75% | mb | Y |
| Bl21*/pET29a-empty vector 1:20 | | 1 | 8% | mb | 1 | 8% | b | |

TABLE 17

Insecticidal activity of purified C398L variant of WoodsCRW against WCR

| Treatment | SEQ ID NO. | Day 3 Dead | Day 3 % Mort | Day 3 Remarks | Day 6 Dead | Day 6 % Mort | Day 6 Remarks | SGF |
|---|---|---|---|---|---|---|---|---|
| WoodsCRW C398L 200 µg/mL | 55 | 6 | 50% | m | 11 | 92% | m | Y |
| WoodsCRW C398L 100 µg/mL | 55 | 0 | 0% | mb | 10 | 83% | m | Y |
| WoodsCRW C398L 50 µg/mL | 55 | 0 | 0% | mb | 6 | 50% | mb | Y |
| WoodsCRW C398L 25 µg/mL | 55 | 0 | 0% | mb | 4 | 33% | b | Y |
| WoodsCRW C398L 12.5 µg/mL | 55 | 1 | 8% | mb | 2 | 17% | b | Y |
| WoodsCRW C398L 200 µg/mL | 55 | 3 | 25% | m | 11 | 92% | m | Y |
| WoodsCRW C398L 100 µg/mL | 55 | 0 | 0% | mb | 5 | 42% | m | Y |
| WoodsCRW C398L 50 µg/mL | 55 | 0 | 0% | mb | 4 | 33% | mb | Y |
| WoodsCRW C398L 25 µg/mL | 55 | 1 | 8% | mb | 4 | 33% | 3m, 5b | Y |
| WoodsCRW C398L 12.5 µg/mL | 55 | 0 | 0% | mb | 1 | 8% | b | Y |
| 1X PBS | | 0 | 0% | mb | 0 | 0% | b | |
| 1X PBS | | 0 | 0% | mb | 1 | 8% | b | |

TABLE 18

Insecticidal activity of purified C398Y variant of WoodsCRW against WCR

| Treatment | SEQ ID NO. | Day 3 Dead | Day 3 % Mort | Day 3 Remarks | Day 6 Dead | Day 6 % Mort | Day 6 Remarks | SGF |
|---|---|---|---|---|---|---|---|---|
| WoodsCRW C398Y 200 µg/mL | 67 | 5 | 42% | sm | 8 | 67% | m | Y |
| WoodsCRW C398Y 100 µg/mL | 67 | 4 | 33% | m | 10 | 83% | mb | Y |
| WoodsCRW C398Y 50 µg/mL | 67 | 1 | 8% | mb | 7 | 58% | mb | Y |
| WoodsCRW C398Y 25 µg/mL | 67 | 1 | 8% | mb | 3 | 25% | b | Y |
| WoodsCRW C398Y 12.5 µg/mL | 67 | 1 | 8% | mb | 1 | 8% | b | Y |
| WoodsCRW C398Y 200 µg/mL | 67 | 4 | 33% | m | 10 | 83% | m | Y |
| WoodsCRW C398Y 100 µg/mL | 67 | 4 | 33% | mb | 6 | 50% | mb | Y |
| WoodsCRW C398Y 50 µg/mL | 67 | 6 | 50% | mb | 7 | 58% | mb | Y |
| WoodsCRW C398Y 25 µg/mL | 67 | 3 | 25% | mb | 11 | 92% | s | Y |
| WoodsCRW C398Y 12.5 µg/mL | 67 | 0 | 0% | mb | 2 | 17% | mb | Y |
| 1X PBS | | 0 | 0% | mb | 1 | 8% | b | |
| 1X PBS | | 0 | 0% | mb | 0 | 0% | b | |

TABLE 19

Insecticidal activity of purified D397-Leu-Leu-C398 variant of WoodsCRW against WCR

| Treatment | SEQ ID NO. | Day 3 Dead | Day 3 % Mort | Day 3 Remarks | Day 6 Dead | Day 6 % Mort | Day 6 Remarks | SGF |
|---|---|---|---|---|---|---|---|---|
| WoodsCRW D397-Leu-Leu-C398 200 µg/mL | 86 | 11 | 92% | s | 12 | 100% | | Y |
| WoodsCRW D397-Leu-Leu-C398 200 µg/mL | 86 | 9 | 75% | sm | 12 | 100% | | Y |
| WoodsCRW D397-Leu-Leu-C398 100 µg/mL | 86 | 9 | 75% | sm | 12 | 100% | | Y |
| WoodsCRW D397-Leu-Leu-C398 100 µg/mL | 86 | 8 | 67% | sm | 12 | 100% | | Y |
| WoodsCRW D397-Leu-Leu-C398 50 µg/mL | 86 | 7 | 58% | m | 12 | 100% | | Y |
| WoodsCRW D397-Leu-Leu-C398 50 µg/mL | 86 | 7 | 58% | m | 12 | 100% | | Y |
| WoodsCRW D397-Leu-Leu-C398 25 µg/mL | 86 | 8 | 67% | m | 12 | 100% | | Y |
| WoodsCRW D397-Leu-Leu-C398 25 µg/mL | 86 | 6 | 50% | m | 11 | 92% | m | Y |
| WoodsCRW D397-Leu-Leu-C398 12.5 µg/mL | 86 | 4 | 33% | m | 6 | 50% | m | Y |
| WoodsCRW D397-Leu-Leu-C398 12.5 µg/mL | 86 | 4 | 33% | m | 9 | 75% | m | Y |
| 1X PBS | | 0 | 0% | mb | 0 | 0% | b | |
| 1X PBS | | 1 | 8% | mb | 1 | 8% | b | |

TABLE 20

Digestion of mutant variants of WoodsCRW in SGF Assay

| WoodsCRW mutant variant | SEQ ID NO. | SGF |
|---|---|---|
| C435L | 61 | N |
| C485L | 62 | N |
| I403L/I404L | 63 | N |
| V399L | 64 | N |
| V399F | 65 | N |
| C398F | 66 | Y |
| C398I | 68 | N |
| C398M | 69 | N |

As shown in Table 9, the WoodsCRW C313S/C383S/C398S/C435S/C485S mutant variant (SEQ ID NO: 42) has very low insecticidal activity, with a 33% mortality rate by day 6 when using 580 µg/mL of protein. Table 10 shows that the WoodsCRW variant C383S/C435S/C485S (SEQ ID NO: 41) also has low insecticidal activity, with a 42% mortality rate by day 6 when using 50 µg/mL of protein. Additionally, Table 8 shows that WoodsCRW variants C398S/C435S (SEQ ID NO: 39) and C398S/C485S (SEQ ID NO: 40) have reduced insecticidal activity. Table 7 also shows that WoodsCRW variants C435S (SEQ ID NO: 29), and C383S (SEQ ID NO: 31) had some level of reduced insecticidal activity. These results indicate that at least one of the modified cysteines and/or a combination of at least two of the modified cysteines play an important role in the insecticidal activity of WoodsCRW. These results also indicate that a protein domain from about amino acid 313 to about amino acid 485 is essential for WoodsCRW insecticidal activity.

As shown in Tables 14-16 and 19, the leucine insertions around position C398 retain relatively high insecticidal activity and are digestible by SGF. Additionally, mutating C398 to L or Y also results in a WoodsCRW mutant variant with relatively high insecticidal activity against WCR and SGF digestibility (Tables 17 and 18).

Example 8: WoodsCRW Variants C398L and C398Y Insecticidal Against Cry3-Resistant WCR To determine if WoodsCRW mutant variants C398L and C398Y retained insecticidal activity on WCR resistant to Cry3-related proteins, these two variants were assayed for activity on eCry3.1Ab-resistant WCR. The diet-incorporation assays using purified WoodsCRW C398L or C398Y proteins were performed similar to the methods described in Example 4. Results are shown in Table 21. Concentrations of purified protein are included with the treatment. Results indicate that WoodsCRW mutant variants C398L and C398Y possess insecticidal activity against a Cry3-resistant WCR strain.

TABLE 21

Insecticidal activity of purified mutant variants of WoodsCRW against eCry3.1Ab-resistant WCR

| Treatment | SEQ ID NO. | Day 6 Dead | Day 6 % Mort | Day 6 Remarks | SGF |
|---|---|---|---|---|---|
| WoodsCRW C398L 200 µg/mL | 55 | 11 | 92% | m | Y |
| WoodsCRW C398L 100 µg/mL | 55 | 9 | 75% | b | Y |
| WoodsCRW C398L 50 µg/mL | 55 | 4 | 33% | b | Y |
| WoodsCRW C398L 25 µg/mL | 55 | 4 | 33% | b | Y |
| WoodsCRW C398Y 200 µg/mL | 67 | 10 | 83% | m | Y |
| WoodsCRW C398Y 100 µg/mL | 67 | 6 | 50% | b | Y |
| WoodsCRW C398Y 50 µg/mL | 67 | 3 | 25% | b | Y |
| WoodsCRW C398Y 25 µg/mL | 67 | 2 | 17% | b | Y |
| 1X PBS | | 4 | 33% | b | |
| 1X PBS | | 3 | 25% | b | |

Example 9: WoodsCRW has a Domain Essential for Insecticidal Activity

The crystal structure of WoodsCRW was solved and found to have significant structural similarities to Plu1415, a protein from the bacteria *Photorhabdus luminescens* whose crystal structure is described by Rosado et al., 2007 (Science 317: 1548-1551). Like Plu1415, WoodsCRW is comprised of an N-terminal MACPF domain and a C-terminal β-prism domain. Bacterial lysates of Plu1415 were assayed for insecticidal activity following the diet incorporation bioassay method described in Example 1, using 12 WCR larvae. Results are shown in Table 22. Interestingly, Plu1415 does not have insecticidal activity against WCR.

TABLE 22

Insecticidal activity of bacterial lysates of Plu1415 against WCR

| Treatment | SEQ ID NO. | Day 3 | | | Day 6 | | |
| --- | --- | --- | --- | --- | --- | --- | --- |
| | | Dead | % Mort | Remarks | Dead | % Mort | Remarks |
| BL21*/pET29a (empty) | | 1 | 8% | b | 2 | 17% | b |
| BL21*/Plu1415 | 98 | 0 | 0% | b | 10 | 0% | b |

The two crystal structures were used to produce chimeric protein to determine which domain(s) were responsible for the insecticidal activity of WoodsCRW on WCR. Based on structural comparisons of the two proteins, two complementary fusion proteins were produced. The Plu1415-WoodsCRW chimera comprises the N-terminal MACPF domain of Plu1415 (amino acids 1-362) and the C-terminal β-prism domain of WoodsCRW (amino acids 363-506). Similarly, the WoodsCRW-Plu1415 chimera comprises the N-terminal MACPF domain of WoodsCRW (amino acids 1-346) and the C-terminal β-prism domain of Plu1415 (amino acids 347-494). The chimeras were assayed for insecticidal activity to WCR using 12 larvae and following the diet incorporation bioassay method described in Example 1. Results are shown in Tables 23 and 24. Interestingly, the Plu1415-Woods chimera possesses insecticidal activity against WCR, however the Woods-Plu1415 chimera does not. These data indicate that the C-terminal β-prism domain of WoodsCRW is necessary and required for insecticidal activity and can confer insecticidal activity against WCR when fused to a MACPF domain in a chimeric construct.

TABLE 23

Insecticidal activity of Plu1415-Woods chimera against WCR

| Treatment | SEQ ID NO. | Day 4 | | | Day 6 | | |
| --- | --- | --- | --- | --- | --- | --- | --- |
| | | Dead | % Mort | Remarks | Dead | % Mort | Remarks |
| BL21*/pET29a (empty) | | 1 | 8% | mb | 1 | 8% | b |
| BL21*/Plu1415-Woods chimera | 96 | 4 | 33% | m | 10 | 83% | m |

TABLE 24

Insecticidal activity of Woods-Plu1415 chimera against WCR

| Treatment | SEQ ID NO. | Day 4 | | | Day 6 | | |
| --- | --- | --- | --- | --- | --- | --- | --- |
| | | Dead | % Mort | Remarks | Dead | % Mort | Remarks |
| BL21*/pET29a (empty) | | 0 | 0% | b | 0 | 0% | b |
| BL21*/Woods-Plu1415 chimera | 97 | 0 | 0% | b | 0 | 0% | b |

Example 10: Transformation of Maize with WoodsCRW Variants C398L and C398Y

Binary vector constructs suitable for *Agrobacterium*-mediated transformation of WoodsCRW variants C398L and C398Y were produced. The binary vectors each comprise either a maize optimized WoodsCRW variant C398L or a maize optimized WoodsCRW variant C398Y coding sequence, operably linked at the 5' end to a promoter suitable for driving expression in plants and operably linked at the 3' end to a terminator sequence. Maize codon optimization was performed, for example, using the methods described in U.S. Pat. No. 6,320,100 (incorporated by reference herein). The constructs were transformed into *Agrobacterium tumefaciens* using standard molecular biology techniques known to those skilled in the art. To prepare the Agrobacteria for transformation, cells were cultured in liquid YPC media at 28° C. and 220 rpm overnight. *Agrobacterium* transformation of immature maize embryos was performed essentially as described in Negrotto et al., 2000, (Plant Cell Reports 19: 798-803). For this example, all media constituents are essentially as described in Negrotto et al., supra. However, various media constituents known in the art may be substituted.

Following transformation, selection, and regeneration, plants were assayed for the presence of the PMI gene and the WoodsCRW maize codon-optimized coding sequence for variants C398L or C398Y using TaqMan® analysis. Plants were also tested for the presence of the vector backbone. Plants negative for the vector backbone and comprising one copy of the transgene were transferred to the greenhouse and assayed for resistance to WCR damage.

Example 11: Maize Plants Expressing WoodsCRW Variants have Insecticidal Activity Against WCR The presence of a WoodsCRW variant detected by ELISA in ng/mg total soluble protein (TSP) in leaf or root tissue from each event. Insecticidal activity was determined using the Root Segment Bioassay. Briefly, samples of maize root tissue from each event were taken when WoodsCRW variant-expressing maize events reached the V3-V4 stage. Maize root tissue was placed in a petri dish and then infected with 12 WCR larvae in a root segment bioassay. Two root tissue samples (Rep1 and Rep2) were evaluated for feeding holes (FH) and scarring damage at day 3. Root tissue from non-transformed (null) maize served as the negative control. The data from Tables 25 and 26 show that transgenic expression of a WoodsCRW variant known to have insecticidal activity on CRW provided protection from CRW in WoodsCRW transgenic root tissue when compared to the null sample root tissue (Tables 25 and 26).

TABLE 25

Insecticidal activity of Transgenic WoodsCRW variant C398L Maize against WCR

| Plant ID | root ELISA (ng/mg TSP) | | Root Seg. Bioassay | | |
|---|---|---|---|---|---|
| | Woods | PMI | FH | Scarring | rating |
| 3486 | 9.45 | 458.88 | 11 | m | − |
| 3487 | ND | 133.00 | 15 | m | − |
| 3492 | 4.07 | 205.34 | 8 | lt/m | +/− |
| 3493 | 6.96 | 288.82 | 7 | lt/m | +/− |
| 3496 | 7.72 | 230.38 | 19 | m/h | − |
| 3498 | 3.30 | 185.43 | 2 | lt | + |
| 3500 | ND | 97.30 | 13 | lt/m | − |

TABLE 25-continued

Insecticidal activity of Transgenic WoodsCRW variant C398L Maize against WCR

| Plant ID | root ELISA (ng/mg TSP) | | Root Seg. Bioassay | | |
|---|---|---|---|---|---|
| | Woods | PMI | FH | Scarring | rating |
| 3505 | 1.93 | 225.34 | 8 | lt/m | +/− |
| 3506 | ND | 188.34 | 23 | m | − |
| 3509 | ND | 282.19 | 6 | lt/m | +/− |
| 3510 | ND | 185.11 | 15 | m | − |
| NULL | | | 16 | m | − |
| NULL | | | 19 | m/h | − |
| NULL | | | 12 | m | − |
| NULL | | | 22 | h | − |

ND = none detected;
FH = feeding holes;
L = light scarring;
M = medium scarring;
H = heavy scarring;
+ = excellent performer;
+/− = good performer;
− = poor performer

TABLE 26

Insecticidal activity of Transgenic WoodsCRW variant C398Y Maize against WCR

| Plant ID | leaf ELISA (ng/mg TSP) | | Root Seg. Bioassay | | |
|---|---|---|---|---|---|
| | WoodsCRW | PMI | FH | Scarring | rating |
| 1571 | 30 | 14 | 3 | LT | ++ |
| 1572 | ND | 27 | 8 | LT/M | + |
| 1574 | ND | 441 | 10 | LT/M | + |
| 1576 | 3 | 527 | 8 | M | − |
| 1579 | ND | 584 | 18 | M | − |
| 1580 | 27 | 16 | 7 | LT/M | + |
| 1583 | 27 | 20 | 7 | LT/M | + |
| 1587 | 2 | 13 | 24 | M | − |
| 1589 | 5 | 665 | 6 | LT | + |
| 1592 | 2 | 14 | 11 | LT/M | |
| 1593 | 19 | 266 | 8 | LT/M | + |
| 1595 | 32 | 625 | 6 | LT/M | + |
| 1596 | 3 | 528 | 6 | LT | + |
| 1598 | 29 | 81 | 8 | LT/M | + |
| 1604 | ND | 517 | 21 | M | − |
| 1606 | 12 | 11 | 15 | M | − |
| 1607 | ND | 21 | 19 | M | − |
| 1609 | ND | 30 | 8 | LT/M | + |
| 1610 | 2 | 24 | 10 | LT/M | + |
| 1613 | ND | 298 | 6 | LT/M | + |
| 1615 | 3 | 263 | 5 | LT/M | + |
| 1616 | 21 | 156 | 11 | LT/M | − |
| 1619 | ND | 330 | 5 | LT/M | + |
| 1621 | ND | 17 | 6 | LT/M | + |
| 1622 | ND | 41 | 17 | M | − |
| 1623 | ND | 25 | 8 | LT/M | + |
| NULL | | | 33 | H | − |
| NULL | | | 30 | H | − |
| NULL | | | 25 | H | − |
| NULL | | | 24 | H | − |

ND = none detected;
FH = feeding holes;
L = light scarring;
M = medium scarring;
H = heavy scarring;
+ = excellent performer;
+/− = good performer;
− = poor performer

Example 12: WoodsCRW in Combination with an Interfering RNA have Insecticidal Activity Against WCR WoodsCRW and/or a WoodsCRW variant are purified as in Example 2. dsRNA against an essential target and known to have insecticidal activity was prepared. In non-limiting examples, the dsRNA may target a gene encoding vacuolar ATP synthase, beta-tubulin, 26S proteosome subunit p28 protein, EF1α 48D, troponin I, tetraspanin, gamma-coatomer, beta-coatomer, and/or juvenile hormone epoxide hydrolase (U.S. Provisional Application Nos. 62/371,259, 62/371,261, and 62/371,262; U.S. Pat. No. 7,812,219; each herein incorporated by reference). The dsRNA and purified protein are tested for efficacy against WCR in a diet-incorporation assay, performed essentially as described in Example 1.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. An expression cassette comprising a promoter operably linked to a heterologous nucleic acid molecule comprising:
   (a) a nucleotide sequence of any one of SEO ID NOs: 22, 34, 73, or 75;
   (b) a nucleotide sequence that encodes a polypeptide, wherein the amino acid sequence of the polypeptide comprises any one of SEO ID NOs: 55, 67, 86, 87 or 88;
   (c) a nucleotide sequence that is complementary to the nucleotide sequence of (a) or (b) above.

2. A vector comprising the expression cassette of claim 1.

3. A host cell comprising the expression cassette of claim 1.

4. The host cell of claim 3 that is a bacterial host cell or a plant cell.

5. A method of producing a plant having enhanced insect resistance as compared to a control plant or plant part, comprising crossing a first parent plant with a second parent plant, wherein at least the first parent plant comprises within its genome a nucleic acid molecule that comprises the expression cassette of claim 1 and producing a progeny generation, wherein the progeny generation comprises at least one plant that possesses the nucleic acids within its genome and that exhibits enhanced insect resistance as compared to a control plant.

6. The method of claim 5, wherein the enhanced insect resistance is against a *Diabrotica* species.

7. A transgenic maize plant comprising a nucleic acid molecule which confers enhanced insect resistance, wherein said nucleic acid molecule comprises the expression cassette of claim 1.

8. The transgenic maize plant of claim 7, where the transgenic maize plant comprises a second trait and wherein the second trait is insect resistance conferred by an interfering RNA molecule.

9. A method for controlling a coleopteran pest population comprising contacting said population with an effective insect-controlling amount of a polypeptide with insecticidal activity, wherein the polypeptide comprises the amino acid sequence of any of SEQ ID NOs: 55, 67, 86, 87 or 88.

10. A polypeptide comprising the amino acid sequence of any one of SEQ ID NOs: 55, 67, 86, 87, or 88.

* * * * *

UNITED STATES PATENT AND TRADEMARK OFFICE
CERTIFICATE OF CORRECTION

PATENT NO.         : 11,180,774 B2
APPLICATION NO.    : 16/474127
DATED              : November 23, 2021
INVENTOR(S)        : Clarence Michael Reynolds, Christopher Fleming and Mark Montgomery It is certified that error appears in the above-identified patent and that said Letters Patent is hereby corrected as shown below:

In the Claims

In Claim 1 at Column 261, Lines 4-5, the phrase "(a) a nucleotide sequence of any one of SEO ID NOs: 22, 34, 73, or 75;" should read --(a) a nucleotide sequence of any one of SEQ ID NOs: 22, 34, 73, or 75;--

In Claim 1 at Column 261, Lines 6-9, the phrase "(b) a nucleotide sequence that encodes a polypeptide, wherein the amino acid sequence of the polypeptide comprises any one of SEO ID NOs: 55, 67, 86, 87 or 88;" should read --(b) a nucleotide sequence that encodes a polypeptide, wherein the amino acid sequence of the polypeptide comprises any one of SEQ ID NOs: 55, 67, 86, 87 or 88; or--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*